(12) United States Patent
Pruzanski et al.

(10) Patent No.: US 10,894,054 B2
(45) Date of Patent: Jan. 19, 2021

(54) FXR AGONIST COMPOSITIONS FOR COMBINATION THERAPY

(71) Applicant: Intercept Pharmaceuticals, Inc., New York, NY (US)

(72) Inventors: Mark Pruzanski, New York, NY (US); Luciano Adorini, Milan (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/564,799

(22) PCT Filed: Apr. 6, 2016

(86) PCT No.: PCT/US2016/026146
§ 371 (c)(1),
(2) Date: Oct. 6, 2017

(87) PCT Pub. No.: WO2016/164413
PCT Pub. Date: Oct. 13, 2016

(65) Prior Publication Data
US 2018/0117065 A1    May 3, 2018

Related U.S. Application Data

(60) Provisional application No. 62/144,040, filed on Apr. 7, 2015.

(51) Int. Cl.
| | | |
|---|---|---|
| A61K 38/26 | (2006.01) | |
| A61K 31/575 | (2006.01) | |
| A61P 3/10 | (2006.01) | |
| A61K 9/00 | (2006.01) | |
| A61K 45/06 | (2006.01) | |
| C07J 9/00 | (2006.01) | |
| A61K 31/4985 | (2006.01) | |
| A61K 47/54 | (2017.01) | |
| A61K 31/155 | (2006.01) | |
| A61K 31/7048 | (2006.01) | |
| A61P 1/16 | (2006.01) | |
| A61P 3/04 | (2006.01) | |
| C07J 51/00 | (2006.01) | |

(52) U.S. Cl.
CPC .......... *A61K 31/575* (2013.01); *A61K 31/155* (2013.01); *A61K 31/4985* (2013.01); *A61K 31/7048* (2013.01); *A61K 38/26* (2013.01); *A61K 45/06* (2013.01); *A61K 47/542* (2017.08); *A61P 1/16* (2018.01); *A61P 3/04* (2018.01); *A61P 3/10* (2018.01); *C07J 9/005* (2013.01); *C07J 51/00* (2013.01)

(58) Field of Classification Search
CPC .... A61K 9/0053; A61K 31/575; A61K 38/26; A61P 3/10
See application file for complete search history.

(56) References Cited

U.S. PATENT DOCUMENTS

| | | |
|---|---|---|
| 5,747,445 A | 5/1998 | Baeckstroem |
| 7,138,390 B2 | 11/2006 | Pelllicciari |
| 7,932,244 B2 | 4/2011 | Pelllicciari et al. |
| 8,685,934 B2 | 4/2014 | Strumph et al. |
| 9,655,920 B2 | 5/2017 | Connor et al. |
| 2002/0120137 A1 | 8/2002 | Houze et al. |
| 2002/0132223 A1 | 9/2002 | Forman et al. |
| 2003/0003520 A1 | 1/2003 | Shan et al. |
| 2003/0109467 A1 | 6/2003 | Monia et al. |
| 2003/0130296 A1 | 7/2003 | Bauer et al. |
| 2004/0014734 A1 | 1/2004 | Song et al. |
| 2004/0176426 A1 | 9/2004 | Houze et al. |
| 2005/0080064 A1 | 4/2005 | Pelllicciari |
| 2006/0069070 A1 | 3/2006 | Fiorucci et al. |
| 2006/0252670 A1* | 11/2006 | Fiorucci ............... A61K 31/155 514/369 |
| 2007/0142340 A1 | 6/2007 | Pelllicciari |
| 2008/0039435 A1 | 2/2008 | Pelllicciari |
| 2008/0182832 A1 | 7/2008 | Pelllicciari et al. |
| 2008/0299118 A1 | 12/2008 | Hartman et al. |
| 2008/0300235 A1 | 12/2008 | Harnish et al. |
| 2009/0062526 A1 | 3/2009 | Yu et al. |
| 2009/0093524 A1 | 4/2009 | Bell et al. |
| 2009/0105162 A1 | 4/2009 | Rybczynski et al. |
| 2009/0163474 A1 | 6/2009 | Zhang et al. |
| 2009/0215748 A1 | 8/2009 | Harnish et al. |
| 2009/0270460 A1 | 10/2009 | Bell et al. |
| 2009/0312246 A1 | 12/2009 | Baron et al. |
| 2010/0022498 A1 | 1/2010 | Pelllicciari |
| 2010/0056546 A1 | 3/2010 | Gant et al. |
| 2010/0063018 A1 | 3/2010 | Pelllicciari et al. |
| 2010/0069367 A1 | 3/2010 | Boren et al. |
| 2010/0152166 A1 | 6/2010 | Genin et al. |

(Continued)

FOREIGN PATENT DOCUMENTS

| | | |
|---|---|---|
| WO | WO 2000/037077 A1 | 6/2000 |
| WO | WO 2000/058293 A2 | 10/2000 |

(Continued)

OTHER PUBLICATIONS

Lund et al. (2011) Emerging GLP-1 receptor agonists, Expert Opinion on Emerging Drugs, 16:4, 607-618. (Year: 2011).*

(Continued)

*Primary Examiner* — Theodore R. West
(74) *Attorney, Agent, or Firm* — Cooley LLP; Ivor R. Elrifi; Chen Chen

(57) ABSTRACT

The present application relates to a pharmaceutical composition comprising a combination of an FXR agonist and at least one additional therapeutic agent that lowers the glucose level in the blood, stimulates insulin secretion, and/or increases insulin sensitivity. The present application relates to use of the pharmaceutical composition for the treatment or prevention of a FXR mediated disease or condition, such as NAFLD and NASH, a disease or condition related to an elevated level of glucose in the blood, decreased secretion of insulin, and/or decreased insulin sensitivity such as hyperglycemia, diabetes, obesity, and insulin resistance, or for lowering the glucose level in the blood, stimulating insulin secretion, and/or increasing insulin sensitivity.

8 Claims, 28 Drawing Sheets

(56) References Cited

U.S. PATENT DOCUMENTS

| | | | |
|---|---|---|---|
| 2010/0184809 | A1 | 6/2010 | Kremoser et al. |
| 2010/0172870 | A1 | 7/2010 | Andre et al. |
| 2010/0210660 | A1 | 8/2010 | Kremoser et al. |
| 2011/0105475 | A1 | 5/2011 | Roche et al. |
| 2012/0053163 | A1 | 3/2012 | Pelllicciari |
| 2012/0106581 | A1 | 5/2012 | Kakui |
| 2012/0232116 | A1 | 9/2012 | Kremoser et al. |
| 2012/0283234 | A1 | 11/2012 | Pelllicciari et al. |
| 2013/0345188 | A1 | 12/2013 | Steiner et al. |
| 2014/0186438 | A1 | 7/2014 | Manku et al. |
| 2018/0008616 | A1 | 1/2018 | Pruzanski et al. |

FOREIGN PATENT DOCUMENTS

| | | | |
|---|---|---|---|
| WO | WO 2005/011592 | A3 | 2/2005 |
| WO | WO 2006/122977 | A2 | 11/2006 |
| WO | WO 2007/024700 | A2 | 3/2007 |
| WO | WO 2007/076260 | A2 | 7/2007 |
| WO | WO 2011/150285 | A1 | 12/2011 |
| WO | WO 2011/150286 | A2 | 12/2011 |
| WO | WO 2012/106581 | A1 | 8/2012 |
| WO | WO 2013/192097 | A1 | 12/2013 |
| WO | WO 2014/184271 | A1 | 11/2014 |

OTHER PUBLICATIONS

Mudaliar et al., "Efficacy and Safety of the Farnesoid X Receptor Agonist Obeticholic Acid in Patients With Type 2 Diabetes and Nonalcoholic Fatty Liver Disease," Gastroenterology 2013;145:574-582. (Year: 2013).*

Ryan et al., "Liraglutide: once-daily GLP-1 agonist for the treatment of type 2 diabetes," Journal of Clinical Pharmacy and Therapeutics (2011) 36, 260-274. (Year: 2011).*

"Obeticholic acid," CAS Reg. No. 459789-99-2 (retrieved from STN on Oct. 23, 2018). (Year: 2018).*

Cheong et al., "Two small molecule agonists of glucagon-like peptide-1 receptor modulate the receptor activation response differently," Biochem. Biophys. Res. Commun. Jan. 6, 2012;417(1):558-63. PMID: 22177947. (Year: 2012).*

Edmonds and Price, "Oral GLP-1 Modulators for the Treatment of Diabetes," Chapter 9 (pp. 119-130) in Annu. Rep. Med. Chem., Desai (Ed.), vol. 48, pp. 1-633 (2013). (Year: 2013).*

Broichhagen et al., "Optical control of insulin release using a photoswitchable sulfonylurea", Nature Communications, Article No. 6116, 11 pages, (2014).

Brown et al., "Glucagon, cyclic AMP and adrenaline stimulate the degradation of low-density lipoprotein by cultured rat hepatocytes", Biochem. Journal, vol. 262, p. 425-429 (1989).

Filippi et al., "Testosterone Partially Ameliorates Metabolic Profile and Erectile Responsiveness to PDE5 Inhibitors in an Animal Model of Male Metabolic Syndrome", Journal of Sexual Medicine, vol. 6, p. 3274-3288 (2009).

Folch et al. "A Simple Method for the Isolation and Purification of Total Lipides from Animal Tissues", J. Biol. Chem. vol. 226, p. 497-509 (1957).

Honda, et al, "The Selective SGLT2 Inhibitor Ipragliflozin Has a Therapeutic Effect on Nonalcoholic Steatohepatitis in Mice", PloS, 2016.

Huang et al., "Meclizine Is an Agonist Ligand for Mouse Constitutive Androstane Receptor (CAR) and an Inverse Agonist for Human CAR", Molecular Endocrinol. vol. 18, No. 10, p. 2402-2408 (2004).

Huang et al., "A traditional herbal medicine enhances bilirubin clearance by activating the nuclear receptor CAR", J Clin. Invest. vol. 113, p. 137-143 (2004).

Kleiner et al, "A traditional herbal medicine enhances bilirubin clearance by activating the.nuclear receptor CAR", Hepatology vol. 41, p. 1313-1321 (2005).

Maneschi et al. "Testosterone treatment improves metabolic syndrome-induced adipose tissue derangements", Journal of Endocrinology, vol. 215, p. 347-362 (2012).

Morelli et al., "Testosterone and farnesoid X receptor agonist INT-747 counteract high fat diet-induced bladder alterations in a rabbit model of metabolic syndrome" Journal of Steroid Biochemistry and Molecular Biology , vol. 132, p. 80-92 (2012).

Morelli et al., "Mechanism of Action of PhosphodiesteraseType 5 Inhibition in Metabolic Syndrome-Associated ProstateAlterations: An Experimental Study in the Rabbit", Prostate 73, 428-441 (2013).

Pellicciari et al., "6a-Ethyl-Chenodeoxycholic Acid (6-ECDCA), a Potent and Selective FXR Agonist Endowed with Anticholestatic Activity", J. Med. Chem. vol. 45, No. 17, p. 3569-3572 (2002).

Perdomo et al., "Increased β-Oxidation in Muscle Cells Enhances Insulin-stimulated Glucose Metabolism and Protects against Fatty Acid-induced Insulin Resistance Despite Intramyocellular Lipid Accumulation", Journal of Biological Chemistry vol. 279, No. 25, p. 27177-27186 (2004).

Qiao et al., "Deoxycholic Acid (DCA) Causes Ligand-independent Activation of Epidermal Growth Factor Receptor (EGFR) and FAS Receptor in Primary Hepatocytes: Inhibition of EGFR/Mitogen-activated Protein Kinase-Signaling Module Enhances DCA-induced Apoptosis", Molecular Biology of the Cell, vol. 12, p. 2629-2645 (2001).

Scrocchi et al., "Glucose Intolerance nut normal satiety in mice with a null mutation in the glucagon-like peptide 1 receptor gene", Nature Medicine vol. 2, No. 11, p. 1254-1258 (1996).

Seglen "Preparation of Isolated Rat Liver Cells", Methods in Cell Biol. vol. 13, p. 29-83 (1976).

Shivaprasad et al. "Bromocriptine in type 2 diabetes mellitus", Indian Journal of Endocrinology and Metabolism, vol. 15(suppl 1), p. S17-S24 (2011).

Vignozzi et al., "Farnesoid X Receptor Activation Improves Erectile Function in Animal Models of Metabolic Syndrome and Diabetes", J Sexual Med vol. 8, p. 57-77 (2011).

Vignozzi et al., "Testosterone protects from metabolic syndrome-associated prostate inflammation: an experimental study in rabbit", Journal of Endocrinology vol. 212, p. 71-84 (2012).

Wang et al., "Farnesoid X Receptor Protects Liver Cells from Apoptosis Induced by Serum Deprivation in Vitro and Fasting in Vivo", Molecular Endocrinology. vol. 22, No. 7, p. 1622-1632 (2008).

Yang et al., "Spontaneous Development of Liver Tumors in the Absence of the Bile Acid Receptor Farnesoid X Receptor", Cancer Research, vol. 67, No. 3, p. 863-867 (2007).

Ali A. H. et al. "Recent advances in the development of farnesoid X receptor agonists", Annals of Translational Medicine, (2015), vol. 3, No. 1, p. 5-583906.

Tanaka et al. "Biochemical responses to bezafibrate improve long-term outcome in asymptomatic patients with primary biliary cirrhosis refractory to UDCA", Journal of Gastroenterology, (2015), vol. 50, p. 675-682.

Teramoto et al. "Effects of bezafibrate on lipid and glucose metabolism in dyslipidemic patients with diabetes: the J-BENEFIT study", Cardiovascular Diabetology, (2012), vol. 11, p. 29-39.

Armstrong M. et al. "Effect of liraglutide on adipose insulin resistance and hepatic de-novo lipogenesis in non-alcoholic steatohepatitis: substudy of a phase 2, randomised placebo-controlled trial", Poster Abstracts 2014, 1 page. Retrieved from the Internet: URL:https://www.thelancet.com/pdfs/journals/lancet/PIIS0140-6736(14)60284-1.pdf.

Blonde L. et al. "Comparison of liraglutide versus other incretin-related anti-hyperglycaemic agents", Diabetes, Obesity and Metabolism, vol. 14, 2012, pp. 20-32.

Xiaokun Ding et al. "Exendin-4, a glucagon-like protein-1 (GLP-1) receptor agonist, reverses hepatic steatosis inob/ob mice", Hepatology, vol. 43, No. 1, 2006, pp. 173-181.

Adorini L. et al. "Farnesoid X receptor targeting to treat nonalcoholic steatohepatitis", Drug Discovery Today, 2012, vol. 17, No. 17-18), p. 988-997.

Fiorucci, S. et al. "Targeting farnesoid X receptor for liver and metabolic disorders", Trends in Molecular Medicine, 2007, vol. 13, No. 7, p. 298-309.

(56) References Cited

OTHER PUBLICATIONS

Harder H. et al. "The effect of liraglutide, a long-acting glucagon-like peptide 1 derivative, on glycemic control, body composition, and 24-h energy expenditure in patients with type 2 diabetes", Diabetes Care, 2004, vol. 27, No. 8, p. 1915-1921.
Nielsen L. et al. "Pharmacology of exenatide (synthetic exendin-4): a potential therapeutic for improved glycemic control of type 2 diabetes", Regulatory Peptides, 2004, vol. 117, No. 2, p. 77-88.
Neuschwander-Tetri B. A. et al. "Farnesoid X nuclear receptor ligand obeticholic acid for non-cirrhotic, non-alcoholic steatohepatitis (FLINT): a multicentre, randomised, placebo-controlled trial", The Lancet, 2014, vol. 385, No. 9972, p. 956-965.
Schuppan et al. "Non-alcoholic steatohepatitis: Pathogenesis and novel therapeutic approaches", Journal of Gastroenterology and Hepatology, 2013, vol. 28, Supplement 1, p. 68-76.

\* cited by examiner

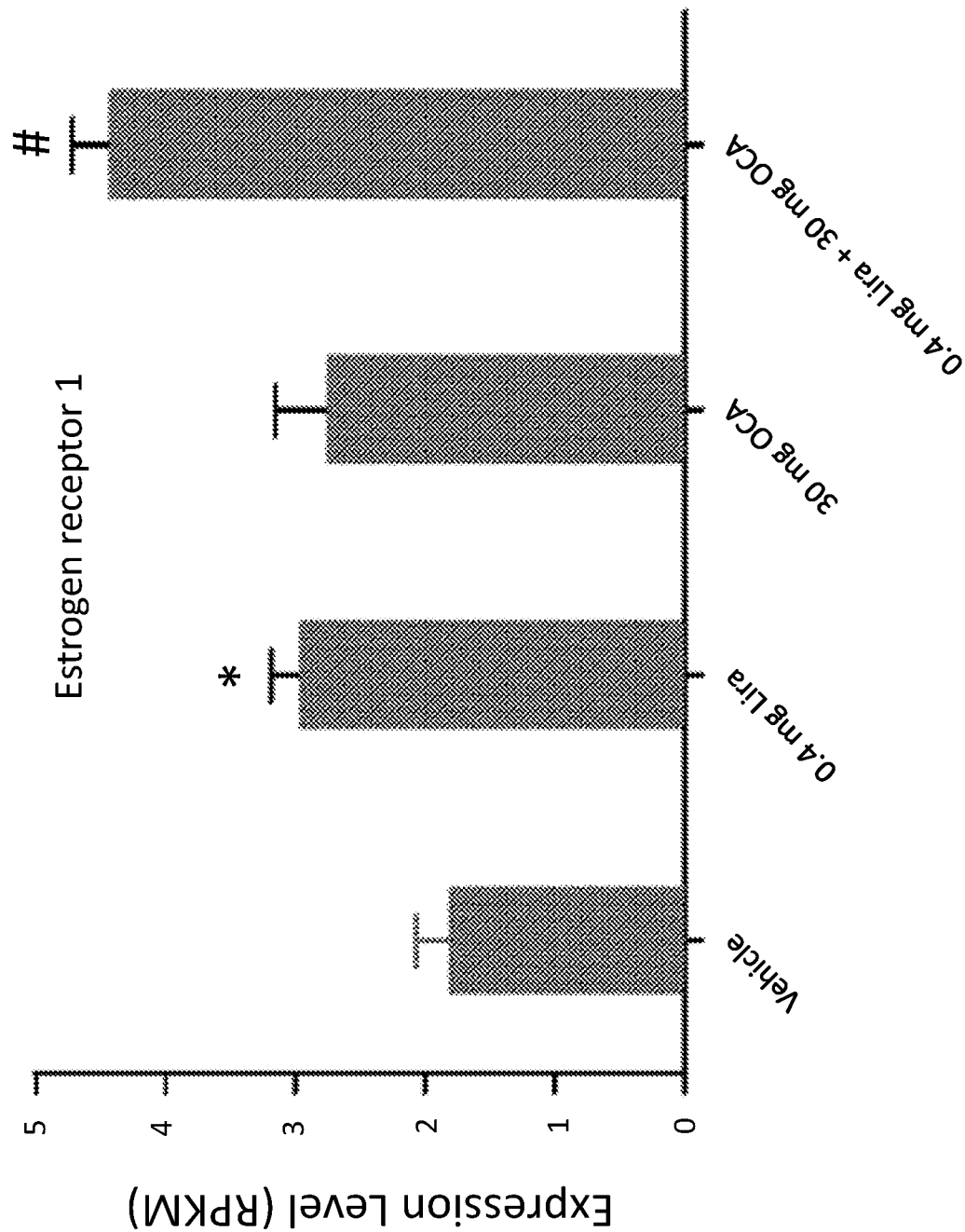

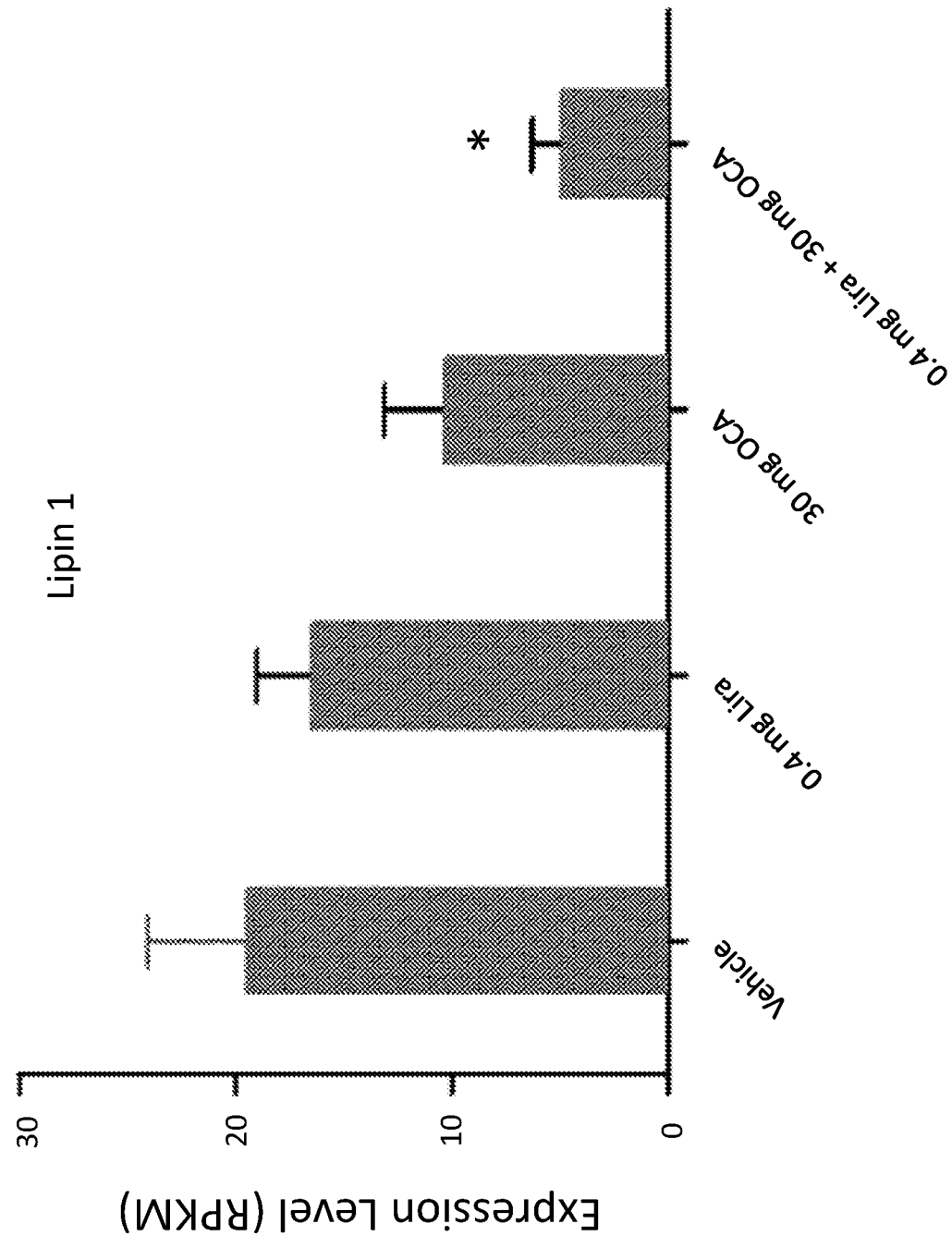

FXR AGONIST COMPOSITIONS FOR COMBINATION THERAPY

BACKGROUND TO THE DISCLOSURE

Metabolic disorders, including diabetes mellitus and insulin resistance syndrome, are characterized by aberrations in a wide variety of metabolic risk markers, such as hyperinsulinemia, impaired glucose metabolism, elevated plasma levels of triglycerides, decreased levels of high-density lipoprotein cholesterol, raised blood pressure, and obesity. Elevated concentrations of glucose in the blood, decreased insulin secretion, and/or increased insulin resistance may be involved in a number of conditions, including primary biliary cirrhosis (PBC), primary sclerosing cholangitis (PSC), various chronic hepatitis states (Hepatitis B and C), nonalcoholic fatty liver disease (NAFLD), and nonalcoholic steatohepatitis (NASH). Current treatments target either insulin resistance (e.g., metformin, thiazolidinediones ("TZDs")) or insulin release from the beta cell (e.g., sulfonylureas, exenatide). However, these treatments suffer from various deficiencies, including side effects, limited efficacy, and undesirable long-term effects.

Bile acids are involved in the regulation of various metabolic processes, and modulate not only their own synthesis and enterohepatic circulation, but also triglyceride, cholesterol, glucose, and energy homeostasis. Bile acids may also play an additional role in modulating incretin release and in metabolic regulation through modulation of energy expenditure. Moreover, bile acid sequestrants (BASs) have shown their role in the treatment of various liver diseases, such as NAFLD and NASH, dysglycemia, and Type II diabetes.

Bile acids bind to the nuclear receptor FXR, which is involved in bile acid homeostasis. It has been suggested that diabetes is associated with a dysregulation of FXR expression. FXR appears to not only play a role in modifying carbohydrate-induced gene expression as well as hepatic glucose production during postprandial and fasting hepatic glucose utilization, but also be involved in the regulation of a complex array of gluconeogenic genes that are necessary for preventing fasting hypoglycemia through maintenance of postprandial hepatic glucose production and glycogen storage. Further, FXR activation inhibits the induction of glucose-responsive genes, such as L-type pyruvate kinase (L-PK), in the postprandial state.

Thus, there are unmet needs for pharmaceutical compositions comprising FXR agonists, and at least one additional therapeutic agent that decreases blood glucose level, stimulates insulin secretion, and/or increases insulin sensitivity, for treating or preventing various diseases or conditions associated with an elevated level of glucose in the blood, decreased secretion of insulin, and/or decreased insulin sensitivity. The present application addresses such needs.

BRIEF DESCRIPTION OF THE DRAWINGS

FIG. 7A is a bar graph showing the effect on the expression level of Cell Death-inducing DFFA-like Effector C. FIG. 7B is a bar graph showing the effect on the expression level of Death Effector Domain-Containing DNS Binding Protein. FIG. 7C is a bar graph showing the effect on the expression level of 2-Hydorxyacyl-CoA-Lyase. FIG. 7D is a bar graph showing the effect on the expression level of Lectin, Galactose Binding Protein. FIG. 7E is a bar graph showing the effect on the expression level of Oxysterol binding protein-like 3 receptor.

FIGS. 8A-8D describe the effect on the expression level of genes uniquely regulated by a high dose OCA and LIRA, alone and in combination. *$p<0.005$ vs. vehicle control and #$p<0.05$ vs. vehicle control. FIG. 8A is a bar graph showing the effect on the expression level of estrogen receptor 1. FIG. 8B is a bar graph showing the effect on the expression level of insulin induced gene 2. FIG. 8C is a bar graph showing the effect on the expression level of lipin 1.

FIG. 8D is a bar graph showing the effect on the expression level of ubiquinol-cytochrome C reductase hinge protein.

FIG. 14A is a bar graph showing the effect of low dose of OCA and MET, alone and in combination, on mRNA expression of decorin. FIG. 14B is a bar graph showing the effect of low dose of OCA and MET, alone and in combination, on mRNA expression of lamanin subunit 1. FIG. 14C is a bar graph showing the effect of low dose of OCA and MET, alone and in combination, on mRNA expression of monocyte to macrophage differentiation factor 2. FIG. 14D is a bar graph showing the effect of low dose of OCA and MET, alone and in combination, on mRNA expression of transforming growth factor B1 transcript. FIG. 14E is a bar graph showing the effect of high dose of OCA and MET, alone and in combination, on mRNA expression of tumor necrosis factor receptor superfamily, member 11b. FIG. 14F is a bar graph showing the effect of low dose of OCA and MET, alone and in combination, on mRNA expression of tumor necrosis factor receptor superfamily, member 19.

FIG. 15A is a bar graph showing the effect of high dose of OCA and MET, alone and in combination, on mRNA expression of collagen type 14a1. FIG. 15B is a bar graph showing the effect of high dose of OCA and MET, alone and in combination, on mRNA expression of collagen type 6a1. FIG. 15C is a bar graph showing the effect of high dose of OCA and MET, alone and in combination, on mRNA expression of collagen type 6a2.

FIG. 16A is a bar graph showing the effect of low dose of OCA and MET, alone and in combination, on mRNA expression of platelet-derived growth factor receptor beta. FIG. 16B is a bar graph showing the effect of low dose of OCA and MET, alone and in combination, on mRNA expression of decorin. FIG. 16C is a bar graph showing the effect of low dose of OCA and MET, alone and in combination, on mRNA expression colectin subfamily member 10. FIG. 16D is a bar graph showing the effect of low dose of OCA and MET, alone and in combination, on mRNA expression of transforming growth factor beta receptor III. FIG. 16E is a bar graph showing the effect of low dose of OCA and MET, alone and in combination, on mRNA expression of transforming growth factor, beta-induced.

SUMMARY OF THE DISCLOSURE

Figure 1A:
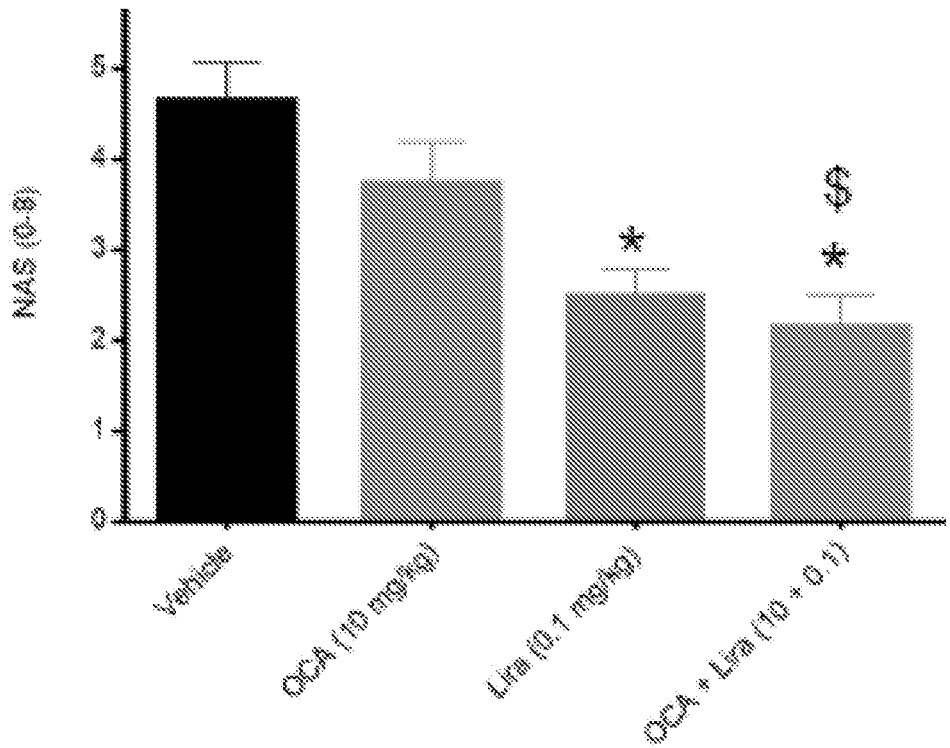
FIG. 1A is a bar graph showing the effect of a low dose of obeticholic acid (OCA) and liraglutide (LIRA), alone and in combination, on total NAS. *$p<0.05$ vs. control and $^\$p<0.05$ vs. OCA.

The present application relates to a pharmaceutical composition comprising (i) a first compound, (ii) at least one additional therapeutic agent, and (iii) optionally one or more pharmaceutically acceptable carriers, wherein the first compound is an FXR agonist and the at least one additional therapeutic agent lowers the glucose level in the blood, stimulates insulin secretion, and/or increases insulin sensitivity.

The present application also relates to the therapeutic use of the pharmaceutical compositions of the present application.

In one embodiment, the first compound is a compound of formula I:

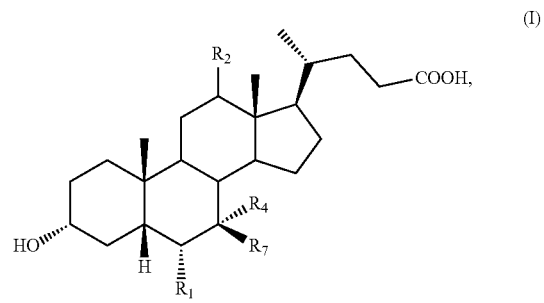

or a pharmaceutically acceptable salt or amino acid conjugate thereof, wherein $R_1$, $R_2$, $R_4$, and $R_7$ are as defined herein.

The present application also relates to methods for treating or preventing an FXR-mediated disease or condition and/or a disease or condition related to an elevated level of glucose in the blood, decreased secretion of insulin, and/or decreased insulin sensitivity, comprising administering a therapeutically effective amount of a pharmaceutical composition of the present application to a subject in need thereof. In one embodiment, the FXR-mediated disease or condition is treated by FXR activation.

The present application also relates to methods for treating or preventing nonalcoholic fatty liver disease (NAFLD) or nonalcoholic steatohepatitis (NASH), comprising administering a therapeutically effective amount of a pharmaceutical composition of the present application to a subject in need thereof.

The present application also relates to methods for lowering the glucose level in the blood, stimulating insulin secretion, and/or increasing insulin sensitivity, comprising administering a therapeutically effective amount of a pharmaceutical composition of the present application to a subject in need thereof.

The present application also relates to methods for treating or preventing hyperglycemia, diabetes mellitus, or obesity, comprising administering a therapeutically effective amount of a pharmaceutical composition of the present application to a subject in need thereof.

The present application also relates to use of a pharmaceutical composition of the present application for lowering the glucose level in the blood, stimulating insulin secretion, increasing insulin sensitivity, treating or preventing an FXR-mediated disease or condition and/or a disease or condition related to an elevated level of glucose in the blood, decreased secretion of insulin, and/or decreased insulin sensitivity, and/or treating or preventing NAFLD, NASH, hyperglycemia, diabetes mellitus, or obesity. In one embodiment, the disease or condition is treated by FXR activation.

The present application also relates to use of a pharmaceutical composition of the present application in the manufacture of a medicament for lowering the glucose level in the blood, stimulating insulin secretion, increasing insulin sensitivity, treating or preventing an FXR-mediated disease or condition and/or a disease or condition related to an elevated level of glucose in the blood, decreased secretion of insulin, and/or decreased insulin sensitivity, and/or treating or preventing NAFLD, NASH, hyperglycemia, diabetes mellitus, or obesity. In one embodiment, the disease or condition is treated by FXR activation.

The compositions and methods of the present application address unmet needs in the treatment or prevention of a disease or disorder in which elevated concentrations of glucose in the blood, decreased secretion of insulin, and/or decreased insulin sensitivity, are involved.

DETAILED DESCRIPTION OF THE DISCLOSURE

The present application is directed to a pharmaceutical composition comprising (i) a first compound, (ii) at least one additional therapeutic agent, and (iii) optionally one or more pharmaceutically acceptable carriers, wherein the first compound is an FXR agonist and the at least one additional therapeutic agent lowers the glucose level in the blood, stimulates insulin secretion, and/or increases insulin sensitivity.

In one example, the at least one additional therapeutic agent is an agent that increases insulin secretion. In another example, the at least one additional therapeutic agent is an agent that increases the sensitivity of target cells, tissues, or organs to insulin. In another example, the at least one additional therapeutic agent is an agent that decreases the level of glucose in the blood.

In one example, the at least one additional therapeutic agent is insulin or an insulin analog. In a further example, the insulin or insulin analog is selected from Humulin® R, insulin lispro (Humalog®), insulin aspart (Novolog®), insulin glulisine (Apidra®), Prompt insulin zinc (Semilente®), insulin glargine (Lantus®), insulin detemir (Levemir®), Isophane insulin, insulin zinc (Lente®), extended insulin zinc (Ultralente®), insulin degludec, Exubera®, and Afrezza®.

In one example, the at least one additional therapeutic agent is an inhibitor of the ATP-sensitive $K^+$ channel in the pancreatic beta cells. In a further example, the at least one additional therapeutic agent is a sulfonylurea. In a further example, the sulfonylurea is selected from tolbutamide (Orinase®), acetohexamide (Dymelor), tolazamide (Tolinase®), chlorpropamide (Diabinese®), carbutamide (Glucidoral®), metahexamide, glipizide (Glucotrol®), glyburide or glibenclamide (Micronase®), glycopyramide, gliquidone (Glurenorm), gliclazide (Uni Diamicron), glibornuride, glisoxepide, glimepiride (Amaryl®), and JB253 (Broichhagen et al., Nature Comm. 5, Article No. 5116 (2014)). In another further example, the at least one additional therapeutic agent is selected from meglitinide, repaglinide (Prandin®), nateglinide (Starlix®), mitiglinide, and linogliride.

In one example, the at least one additional therapeutic agent is an agonist of FFA1/GPR40 (Free Fatty acid Receptor 1). In a further example, the FFA1/GPR40 agonist is fasiglifam.

In one example, the at least one additional therapeutic agent is an incretin mimetic. In a further example, the incretin mimetic is a glucagon-like peptide-1 (GLP-1) or agonist of the GLP-1 receptor thereof. In a further example, the GLP-1 receptor agonist is selected from exenatide/exendin-4, liraglutide, taspoglutide, lixisenatide, albiglutide, dulaglutide, semaglutide, BRX-0585 (Pfizer/Biorexis), and CJC-1134-PC (exendin-4 conjugated to human albumin). In another further example, the incretin mimetic is a gastric inhibitory peptide (GIP) or GIP analog.

In one example, the at least one additional therapeutic agent is an inhibitor of dipeptidyl peptidase-4 (DPP-4, also known in the art as DPP-IV). In a further example, the DPP-4 inhibitor is selected from vildagliptin (Galvus®), sitagliptin (Januvia®), saxagliptin (Onglyza®), linagliptin (Tradjenta), alogliptin, septagliptin, anagliptin, gemigliptin, teneligliptin, carmegliptin, gosogliptin, dutogliptin, berberine, and lupeol.

In one example, the at least one additional therapeutic agent is a human peroxisome proliferator activated receptor (PPAR) gamma agonist. In a further example, the PPAR gamma agonist is selected from thiazolidinediones and glitazones, e.g., rosiglitazone, troglitazone, pioglitazone, englitazone, balaglitazone, rivoglitazone, ciglitazone, lobeglitazone, and netoglitazone.

In one example, the at least one additional therapeutic agent is a biguanide. In a further example, the biguanide is selected from metformin, buformin, and phenformin.

In one example, the at least one additional therapeutic agent is a bile acid sequestrant. In a further example, the bile acid sequestrant is selected from anion exchange resin, quaternary amines (e.g., cholestyramine or colestipol), and an ileal bile acid transporter inhibitor.

In one example, the at least one additional therapeutic agent is an agent that facilitates metabolism of glucose (e.g., phosphorylation of glucose). In one example, the at least one additional therapeutic agent is a glucokinase activator. In a further example, the glucokinase activator is a compound as described in WO 2000/058293.

In one example, the at least one additional therapeutic agent is an agent that blocks renal reabsorption of glucose. In one example, the at least one additional therapeutic agent is a SGLT-2 inhibitor. In a further example, the SGLT-2 inhibitor is selected from canagliflozin, dapagliflozin, empagliflozin, remogliflozin, sergliflozin, tofogliflozin, ipragliflozin, and ertugliflozin.

In one example, the at least one additional therapeutic agent is an agent that reduces glucose absorption in the intestine. In one example, the at least one additional therapeutic agent is an alpha-glucosidase inhibitor. In a further example, the alpha-glucosidase inhibitor is selected from miglitol (Glyset®), acarbose (Precose®), and voglibose.

In one example, the at least one additional therapeutic agent is an agent that slows gastric emptying and/or suppresses glucagon. In one example, the at least one additional therapeutic agent is an amylin or amylin analog. In a further example, the amylin analog is pramlintide.

In one example, the at least one additional therapeutic agent is a microsomal triglyceride transfer protein (MTP)

inhibitor. In a further example, the MTP inhibitor is selected from midaglizole, isaglidole, deriglidole, idazoxan, efaroxan, and fluparoxan.

In one example, the at least one additional therapeutic agent is selected from bromocriptine, benfluorex, and tolrestat.

In one example, the at least one additional therapeutic agent is an agent that lowers the concentration of glucocorticoid. In one example, the at least one additional therapeutic agent is a 11beta-HSD1 inhibitor. In a further example, the 11beta-HSD1 inhibitor is selected from glycyrrhizic acid, glycyrrhetinic acid (enoxolone), carbenoxolone, abietic acid, flavonoid naringenine, anthraquinone emodin, adamantyl[1,2,4]triazolo[4,3-a]azepine, BVT-2733, BVT-116429, BVT-3498/AMG-311, AMG-221, PF-915275, HSD-016, INCB-13739, INCB-20817, MK-0916, MK-0736, AZD-4017, AZD-8329, RG-4929, RG-7234, BMS-816336, and JTT-654,

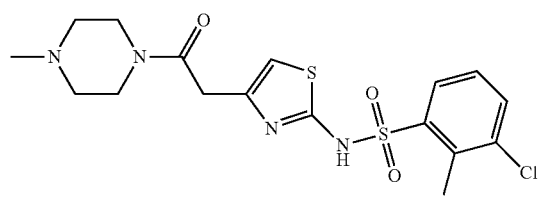
BVT-2733

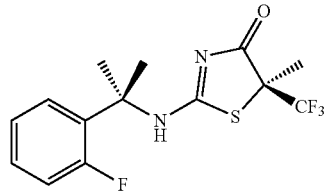
BVT-116429

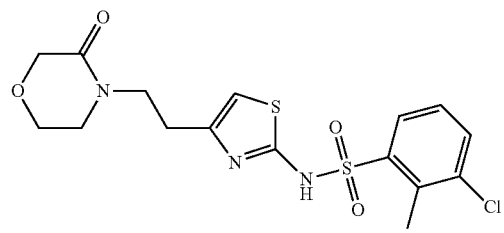
BVT-3498/AMG-311

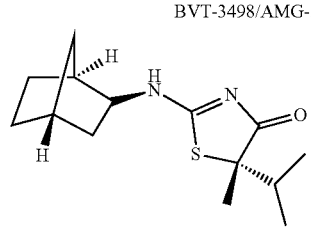
AMG-221

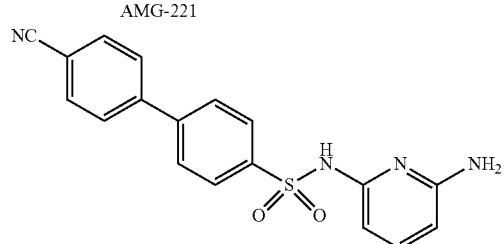
PF-915275

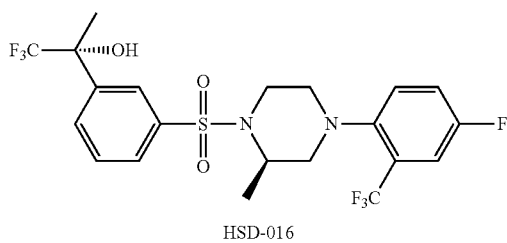
HSD-016

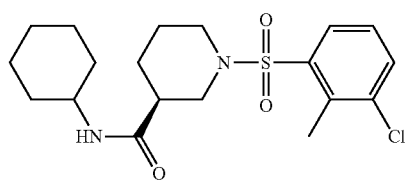
INCB-13739

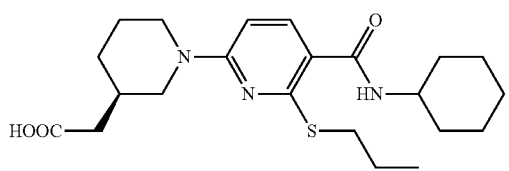
AZD-4017

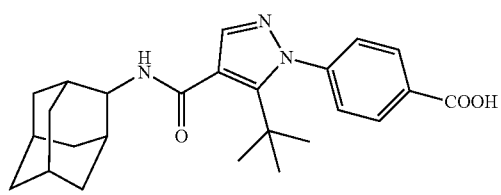
AZD-8329 and a compound selected from the table below:

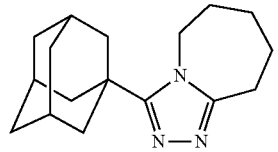 [SMILES: C1CCc2nnc(C34CC5CC(CC(C5)C3)C4)n2CC1]

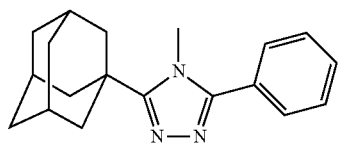 [SMILES: Cn1c(-c2ccccc2)nnc1C12CC3CC(CC(C3)C1)C2]

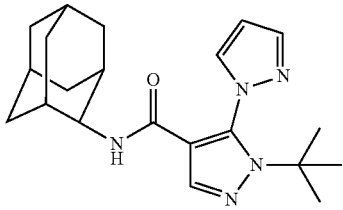 [SMILES: CC(C)(C)n1ncc(C(=O)NC2C3CC4CC(C3)CC2C4)c1-n1cccn1]

-continued
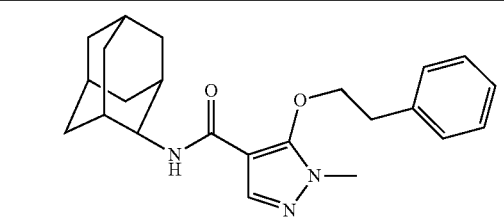
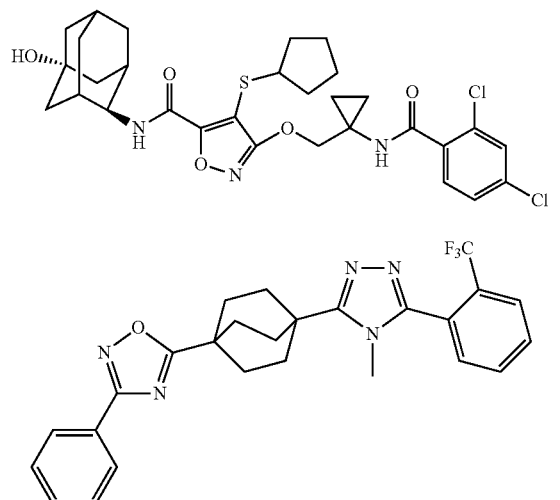
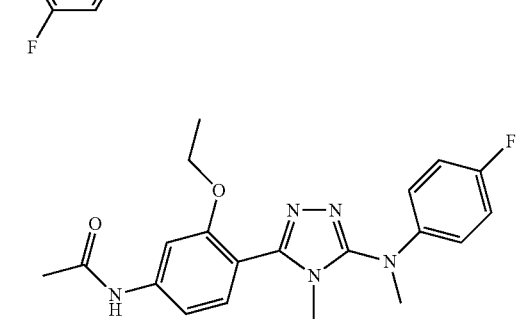
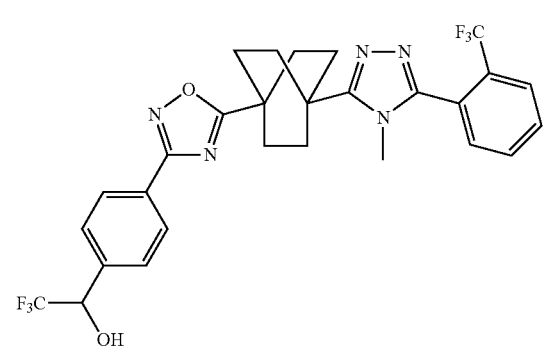 [SMILES: Cn1c(-c2ccccc2C(F)(F)F)nnc1C12CCC(c3nc(-c4ccc(C(O)C(F)(F)F)cc4)no3)(CC1)CC2]
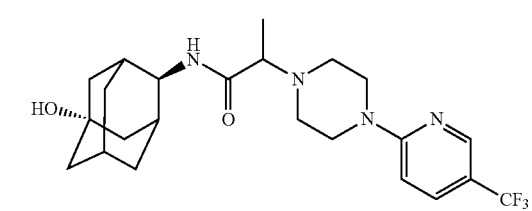 [SMILES: CC(C(=O)N[C@H]1C2CC3CC1C[C@](O)(C3)C2)N1CCN(c2ccc(C(F)(F)F)cn2)CC1]
-continued
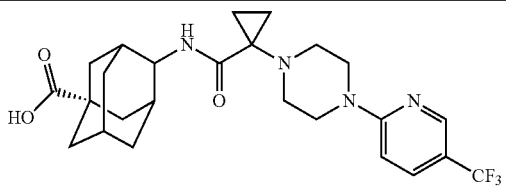
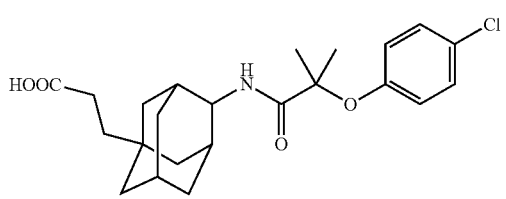 [SMILES: CC(C)(Oc1ccc(Cl)cc1)C(=O)NC1C2CC3CC1CC(CCC(=O)O)(C3)C2]
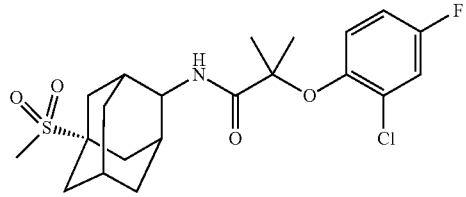
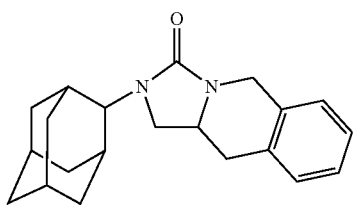 [SMILES: O=C1N2Cc3ccccc3CC2CN1C1C2CC3CC(C2)CC1C3]
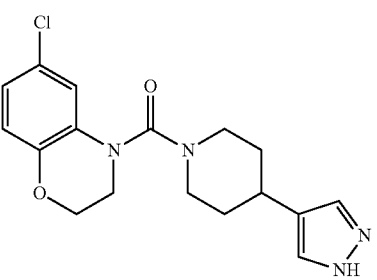 [SMILES: O=C(N1CCC(c2cn[nH]c2)CC1)N1CCOc2ccc(Cl)cc21]
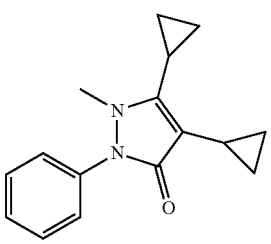 [SMILES: Cn1c(C2CC2)c(C2CC2)c(=O)n1-c1ccccc1]
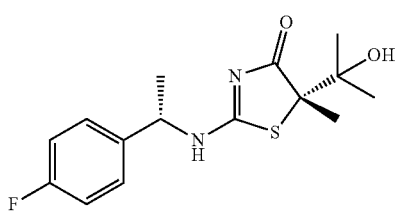 [SMILES: C[C@H](NC1=NC(=O)[C@](C)(C(C)(C)O)S1)c1ccc(F)cc1]

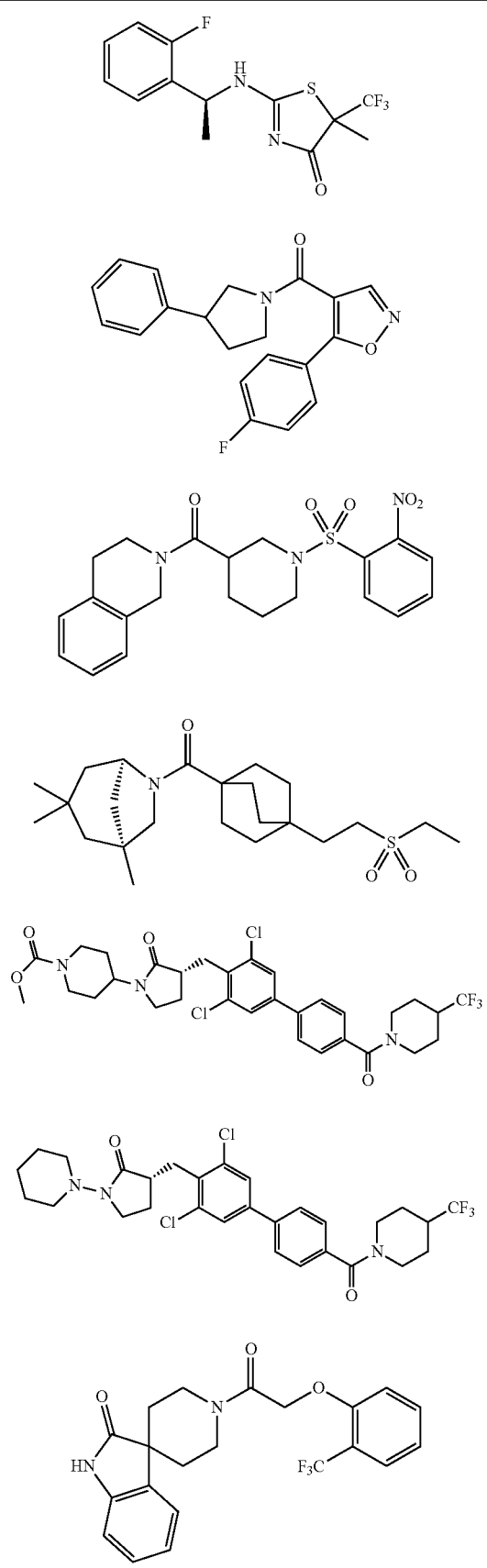

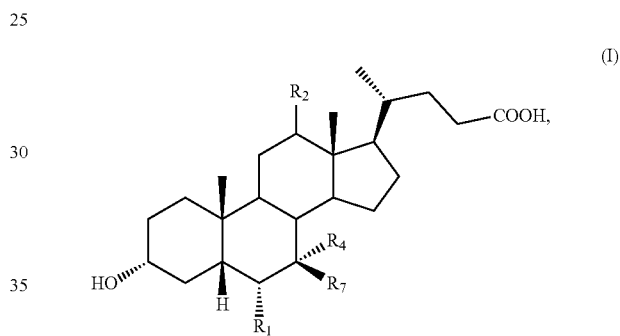

In one example, the first compound of the pharmaceutical composition is a compound of formula I:

(I)

or a pharmaceutically acceptable salt or amino acid conjugate thereof, wherein:
$R_1$ is hydrogen or unsubstituted $C_1$-$C_6$ alkyl;
$R_2$ is hydrogen or α-hydroxyl;
$R_4$ is hydroxyl or hydrogen; and
$R_7$ is hydroxyl or hydrogen.

In one example, $R_1$ is unsubstituted $C_1$-$C_6$ alkyl. In a further example, $R_1$ is unsubstituted $C_1$-$C_3$ alkyl. In a further example, $R_1$ is methyl, ethyl, or propyl. In a further example, R is ethyl.

In one example, $R_2$ is hydrogen. In another example, $R_2$ is α-hydroxyl.

In one example, $R_4$ is hydroxyl and $R_7$ is hydrogen. In another example, $R_4$ is hydrogen and $R_7$ is hydroxyl.

In a further example, $R_1$ is selected from methyl, ethyl and propyl, $R_4$ is hydroxyl, $R_7$ is hydrogen, and $R_2$ is hydrogen. In a further example, $R_1$ is ethyl.

In a further example, $R_1$ is selected from methyl, ethyl and propyl, $R_4$ is hydrogen, $R_7$ is hydroxyl, and $R_2$ is hydrogen. In a further example, $R_1$ is ethyl.

In a further example, $R_1$ is selected from methyl, ethyl and propyl, $R_4$ is hydroxyl, $R_7$ is hydrogen, and $R_2$ is α-hydroxyl. In a further example, $R_1$ is ethyl.

In a further example, $R_1$ is selected from methyl, ethyl and propyl, $R_4$ is hydrogen, $R_7$ is hydroxyl, and $R_2$ is α-hydroxyl. In a further example, $R_1$ is ethyl.

In one example, the amino acid conjugate is a glycine conjugate. In one example, the amino acid conjugate is a taurine conjugate.

In a further example, the compound is

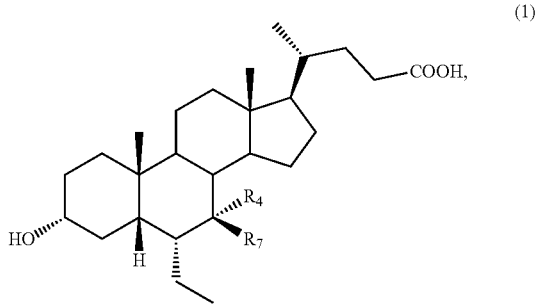

(1)

or a pharmaceutically acceptable salt or amino acid conjugate thereof.

One of the problems to be solved by the present application is the identification of combination therapies for the treatment or prevention of conditions related to elevated concentration of glucose in the blood, such as FXR-mediated diseases (e.g., NAFLD and NASH), hyperglycemia and diabetes, as well as for the reduction of glucose level in the blood, for the increase of insulin secretion, and for the increase of insulin sensitivity. For example, the present application identifies combination therapies for the treatment or prevention of FXR-mediated diseases (e.g., NAFLD and NASH) through reducing glucose level in the blood and/or increasing insulin secretion and/or insulin sensitivity. In one embodiment, the disease or condition is treated by FXR activation. Although drugs for conditions related to elevated glucose level are available, these drugs are often not suitable for many patients for a variety of reasons. For example, many drugs have adverse effects such as nausea, vomiting, diarrhea, dizziness, headache, and weakness. Some drugs may be inadequate for the treatment when administered alone. For example, in some situations one insulin secretion stimulating agent alone is inadequate in controlling the severe level of hyperglycemia that is present in many patients (e.g., patients with NAFLD or NASH). Some drugs may require administration of high doses, or more frequent administration, due to extensive metabolism into inactive or less potent metabolites. Several classes of therapeutic agents including liraglutide are administered via injection. The advantage of orally co-administering a second therapeutic agent may lead to a decreased number and/or frequency of injections. By reducing the number and/or frequency, the therapeutic dosing regimen may allow for greater patient compliance, especially for NASH patients who may not be accustomed to injections. The combination therapies described herein can solve the problems mentioned above and can have one or more advantages of, e.g., synergism, reducing the number of daily doses without the drug losing efficacy, lowering blood glucose in patients, improved potency, selectivity, tissue penetration, half-life, and/or metabolic stability.

In the compositions, packs or kits, methods and uses of the present application, the first compound may be the free acid or it may be a pharmaceutically acceptable salt or amino acid conjugate (e.g., glycine or taurine conjugate). In one example, the first compound is any FXR agonist. In one aspect, the first compound is a compound of formula I. In one aspect, the first compound is obeticholic acid (Compound 1). In one example, the first compound is the free acid of a compound of formula I. In one example, the first compound is the glycine conjugate of a compound of formula I. In one example, the first compound is the taurine conjugate of a compound of formula I.

In the compositions, packs or kits, methods and uses of the present application, the at least one additional therapeutic agent can be any agent described herein. In one example, the at least one additional therapeutic agent is an agent that increases insulin secretion. In another example, the at least one additional therapeutic agent is an agent that increases the sensitivity of target cells, tissues, or organs to insulin. In another example, the at least one additional therapeutic agent is an agent that decreases the level of glucose in the blood.

The compounds of the present application also comprehend an isotopically-labeled first compound or a pharmaceutically acceptable salt or amino acid conjugate thereof, which has a structure that is identical to that of the first compound of the present application (e.g., a compound of formula I), but for the fact that one or more atoms are replaced by an atom having an atomic mass or mass number different from the atomic mass or mass number most commonly found in nature. Examples of isotopes that can be incorporated into the first compound or a pharmaceutically acceptable salt or amino acid conjugate thereof, include isotopes of hydrogen, carbon, nitrogen, fluorine, such as $^3$H, $^{11}$C, $^{14}$C and $^{18}$F.

The first compound or a pharmaceutically acceptable salt or amino acid conjugate thereof that contain the aforementioned isotopes and/or other isotopes of other atoms is within the scope of the present application. Isotopically-labeled first compound or a pharmaceutically acceptable salt or amino acid conjugate thereof, for example, a first compound into which a radioactive isotopes such as $^3$H and/or $^{14}$C are incorporated, is useful in drug and/or substrate tissue distribution assays. Tritiated, i.e., $^3$H, and carbon-14, i.e., $^{14}$C, isotopes are used for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be used in some circumstances. Isotopically labeled first compound or a pharmaceutically acceptable salt or amino acid conjugate thereof can generally be prepared by carrying out the procedures disclosed in the Schemes and/or in the Examples of the application, by substituting a readily available isotopically labeled reagent for a non-isotopically labeled reagent. In one example, obeticholic acid, or pharmaceutically acceptable salts or amino acid conjugates thereof are not isotopically labelled.

The present application also provides a method for treating or preventing a disease or condition, comprising administering a therapeutically effective amount of a pharmaceutical composition of the present application to a subject in need thereof.

In one example, the disease or condition is an FXR mediated disease or condition. Examples of the FXR mediated diseases or conditions include, but are not limited to, liver disease such as a cholestatic or non-cholestatic disease or condition. In one embodiment, the FXR-mediated disease or condition relate to FXR activation. Cholestatic liver diseases include, but are not limited to, primary biliary cirrhosis (PBC), primary sclerosing cholangitis (PSC), portal hypertension, biliary atresia, bile acid diarrhea, liver damage due to progressive fibrosis, liver fibrosis, and chronic liver disease. Non-cholestatic liver diseases or conditions include but are not limited to nonalcoholic fatty liver disease (NAFLD), nonalcoholic steatohepatitis (NASH), hepatitis C infection, alcoholic liver disease, liver damage due to progressive fibrosis, liver, gastrointestinal, and biliary cancers such as hepatocellular carcinoma, cancers of the bile duct, colorectal cancer, gastric cancers, and kidney cancers, liver fibrosis, liver diseases induced by methotrexate, isoniazid, oxyphenistatin, methyldopa, chlorpromazine, tolbutamide, or amiodarone; autoimmune hepatitis; sarcoidosis, Wilson's disease, hemochromatosis, Gaucher's disease, types Ill, IV, VI, IX and X glycogen storage diseases, α1-antitrypsin deficiency, Zellweger syndrome; tyrosinemia, fructosemia, galactosemia, vascular derangement associated with Budd-Chiari syndrome, veno-occlusive disease, or portal vein thrombosis; and congenital hepatic fibrosis. Examples of diseases or conditions treatable by FXR activation also include hyperglycemia, diabetes, obesity, insulin resistance, hyperlipidemia, high LDL-cholesterol, high HDL-cholesterol, high triglycerides, and cardiovascular disease.

NAFLD is a medical condition that is characterized by the build-up of fat (called fatty infiltration) in the liver. NAFLD is one of the most common causes of chronic liver disease, and encompasses a spectrum of conditions associated with lipid deposition in hepatocytes. It ranges from steatosis (simple fatty liver), to nonalcoholic steatohepatitis (NASH), to advanced fibrosis and cirrhosis. The disease is mostly silent and is often discovered through incidentally elevated liver enzyme levels. NAFLD is strongly associated with obesity and insulin resistance and is currently considered by many as the hepatic component of the metabolic syndrome.

Nonalcoholic steatohepatitis (NASH) is a condition that causes inflammation and accumulation of fat and fibrous (scar) tissue in the liver. Liver enzyme levels in the blood may be more elevated than the mild elevations seen with nonalcoholic fatty liver (NAFL). Although similar conditions can occur in people who abuse alcohol, NASH occurs in those who drink little to no alcohol. NASH affects 2 to 5 percent of Americans, and is most frequently seen in people with one of more of the following conditions: obesity, diabetes, hyperlipidemia, insulin resistance, uses of certain medications, and exposure to toxins. NASH is an increasingly common cause of chronic liver disease worldwide and is associated with increased liver-related mortality and hepatocellular carcinoma, even in the absence of cirrhosis. NASH progresses to cirrhosis in 15-20% of affected individuals and is now one of the leading indications for liver transplantation in the United States. At present there are no approved therapies for NASH.

The present application also provides a method for treating or preventing NAFLD or NASH. In one example, the present application provides a method for treating or preventing NAFLD or NASH that is associated with an elevated level of glucose in the blood, decreased secretion of insulin, and/or decreased insulin sensitivity. In one example, the present application provides a method for treating or preventing NAFLD or NASH, at least in part through reducing glucose level in the blood and/or increasing insulin secretion and/or insulin sensitivity. In one example, the present application provides a method for treating or preventing NASH. In one example, the present application provides a method for treating or preventing NASH that is associated with an elevated level of glucose in the blood, decreased secretion of insulin, and/or decreased insulin sensitivity. In one example, the present application provides a method for treating or preventing NASH, at least in part through reducing glucose level in the blood and/or increasing insulin secretion and/or insulin sensitivity.

In one example, the disease or condition is related to an elevated level of glucose in the blood, decreased secretion of insulin, and/or decreased insulin sensitivity. Examples of the disease or condition include, but are not limited to, FXR-mediated diseases (e.g., NAFLD and NASH), hyperglycemia, diabetes, obesity, and insulin resistance.

In one example, the disease or condition is an FXR-mediated disease. In one example, the disease or condition is NAFLD or NASH. In one example, the disease or condition is NASH.

In one example, the disease or condition is hyperglycemia, diabetes, obesity, or insulin resistance. In one example, the disease or condition is hyperglycemia. In one example, the disease or condition is diabetes. In a further example, the diabetes is Type I diabetes. In another further example, the diabetes is Type II diabetes. In one example, the disease or condition is obesity. In one example, the disease or condition is insulin resistance.

The present application also provides a method for treating or preventing hyperglycemia, diabetes, obesity, or insulin resistance, comprising administering a therapeutically effective amount of a pharmaceutical composition of the present application to a subject in need thereof. In one example, the subject is not suffering from a cholestatic condition. In another example, the subject is suffering from a cholestatic condition. In one example, the subject is not suffering from a liver disease. In another example, the subject is suffering from a liver disease. In a further example, the liver disease is selected from a cholestatic liver disease such as PBC, PSC, portal hypertension, bile acid diarrhea, liver damage due to progressive fibrosis, liver fibrosis, and chronic liver disease. In a further example, the subject is suffering from PBC, NAFLD, or NASH. In further example, the subject is suffering from fibrosis. In another further example, the subject is suffering from a non-cholestatic liver disease or condition such as nonalcoholic fatty liver disease (NAFLD), nonalcoholic steatohepatitis (NASH), hepatitis C infection, alcoholic liver disease, liver damage due to progressive fibrosis, liver, gastrointestinal, and biliary cancers such as hepatocellular carcinoma, cancers of the bile duct, colorectal cancer, gastric cancers, and kidney cancers, liver fibrosis, liver diseases induced by methotrexate, isoniazid, oxyphenistatin, methyldopa, chlorpromazine, tolbutamide, or amiodarone; autoimmune hepatitis; sarcoidosis, Wilson's disease, hemochromatosis, Gaucher's disease, types III, IV, VI, IX and X glycogen storage diseases, α1-antitrypsin deficiency, Zellweger syndrome; tyrosinemia, fructosemia, galactosemia, vascular derangement associated with Budd-Chiari syndrome, veno-occlusive disease, or portal vein thrombosis; and congenital hepatic fibrosis.

The present application also provides a method for lowering the glucose level in the blood, stimulating insulin secretion, and/or increasing insulin sensitivity, comprising administering a therapeutically effective amount of a pharmaceutical composition of the present application to a subject in need thereof. In one example, the subject is not suffering from a cholestatic condition. In another example, the subject is suffering from a cholestatic condition. In one example, the subject is not suffering from a liver disease. In another example, the subject is suffering from a liver disease. In a further example, the liver disease is selected from a cholestatic liver disease such as PBC, PSC, portal hypertension, bile acid diarrhea, chronic liver disease, NAFLD, NASH, hepatitis C infection, alcoholic liver disease, liver damage due to progressive fibrosis, liver fibrosis, and chronic liver disease. In a further example, the subject is suffering from PBC, NAFLD, or NASH. In another further example, the subject is suffering from fibrosis. In another example, the subject is suffering from a non-cholestatic liver disease or condition such as nonalcoholic fatty liver disease (NAFLD), nonalcoholic steatohepatitis (NASH), hepatitis C infection, alcoholic liver disease, liver damage due to progressive fibrosis, liver, gastrointestinal, and biliary cancers such as hepatocellular carcinoma, cancers of the bile duct, colorectal cancer, gastric cancers, and kidney cancers, liver fibrosis, liver diseases induced by methotrexate, isoniazid, oxyphenistatin, methyldopa, chlorpromazine, tolbutamide, or amiodarone; autoimmune hepatitis; sarcoidosis, Wilson's disease, hemochromatosis, Gaucher's disease, types III, IV, VI, IX and X glycogen storage diseases, α1-antitrypsin deficiency, Zellweger syndrome; tyrosinemia, fructosemia, galactosemia, vascular derangement associated with Budd-Chiari syndrome, veno-occlusive disease, or portal vein thrombosis; and congenial hepatic fibrosis.

The present application also provides a method for inhibiting or reversing fibrosis, comprising administering a therapeutically effective amount of a pharmaceutical composition of the present application to a subject in need thereof. In one example, the subject is not suffering from a cholestatic condition. In another example, the subject is suffering from a cholestatic condition.

In one example, the subject to which a therapeutically effective amount of a pharmaceutical composition of the present application is administered is not suffering from a cholestatic condition associated with a disease or condition selected from the group consisting of primary liver and biliary cancers, such as hepatocellular carcinoma, colorectal cancer, and cancers of the bile duct, metastatic cancer, sepsis, chronic total parenteral nutrition, cystic fibrosis, and granulomatous liver disease. In one example, the fibrosis to be inhibited or reversed occurs in an organ where FXR is expressed.

In one example, a cholestatic condition is defined as having an abnormally elevated serum level of alkaline phosphatase, γ-glutamyl transpeptidase (GGT), and/or 5' nucleotidase. In another example, a cholestatic condition is further defined as presenting with at least one clinical symptom. In one example, the symptom is itching (pruritus). In another example, a cholestatic condition is selected from the group consisting of primary biliary cirrhosis (PBC), primary sclerosing cholangitis (PBS), drug-induced cholestasis, hereditary cholestasis, and intrahepatic cholestasis of pregnancy.

In one example, the fibrosis is selected from the group consisting of liver fibrosis, kidney fibrosis, and intestinal fibrosis.

In one example, the subject to which a therapeutically effective amount of a pharmaceutical composition of the present application is administered has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease;

hemochromatosis; Gaucher's disease; types III, IV, VI, IX and X glycogen storage diseases; $α_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In another example, the subject has intestinal fibrosis associated with a disease selected from the group consisting of Crohn's disease, ulcerative colitis, post-radiation colitis, and microscopic colitis.

In another example, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

In another example, the subject to which a therapeutically effective amount of a pharmaceutical composition of the present application is administered has intestinal fibrosis associated with a disease selected from the group consisting of Crohn's disease, ulcerative colitis, post-radiation colitis, and microscopic colitis.

In another example, the subject to which a therapeutically effective amount of a pharmaceutical composition of the present application is administered has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

The present application also provides a method for reducing the amount of serum bilirubin, and/or one or more liver enzymes, comprising administering a therapeutically effective amount of a pharmaceutical composition of the present application to a subject in need thereof.

In one example, the method of the present application reduces the amount of serum bilirubin by at least 10%, 20%, 30%, 40%, 50%, 60%, 70%, 80%, or 90%, as compared to a control subject (e.g., a subject not administered with the composition of the present application). In one example, the subject has an elevated level of bilirubin, as compared to a healthy subject (e.g., an individual without a disease or condition, such as those described herein). In one example, the method of the present application reduces the level of bilirubin to a normal level (e.g., similar to the level of bilirubin in an individual without a disease or condition, such as those described herein). In a further example, the method of the present application reduces the level of bilirubin below 10 mg/L, 9 mg/L, 8 mg/L, 7 mg/L, 6 mg/L, 5 mg/L, 4 mg/L, 3 mg/L, 2 mg/L, 1.5 mg/L, 1.2 mg/L, or 1 mg/L. In a further example, the method of the present application reduces the level of bilirubin below 2 mg/L, 1.5 mg/L, 1.2 mg/L, or 1 mg/L.

In one example, the liver enzyme is selected from the group consisting of alkaline phosphatase (ALP, AP, or Alk Phos), alanine aminotransferase (ALT), aspartate aminotransferase (AST), gamma-glutamyl transpeptidase (GGT), lactate dehydrogenase (LDH), and 5' nucleotidase. In one example, the method of the present application reduces the amount of one or more liver enzymes by at least 10%, 20%, 30%, 40%, 50%, 60%, 70%, 80%, or 90%, as compared to a control subject (e.g., a subject not administered with the composition of the present application). In one example, the subject has elevated levels of one or more liver enzymes, as compared to a healthy subject (e.g., an individual without a disease or condition, such as those described herein). In one example, the method of the present application reduces the levels of one or more liver enzymes (e.g., ALP, ALT, AST, GGT, LDH, and 5' nucleotidase) to normal levels (e.g., similar to the levels of liver enzymes in an individual without a disease or condition, such as those described herein).

In a further example, the method of the present application reduces the serum level of ALP below 500 IU/L (international units per liter), 400 IU/L, 300 IU/L, 200 IU/L, 180 IU/L, 160 IU/L, or 150 IU/L. In a further example, the method of the present application reduces the level of ALP to from about 40 IU/L to about 150 IU/L.

In a further example, the method of the present application reduces the level of ALT below 200 IU/L (international units per liter), 150 IU/L, 100 IU/L, 80 IU/L, 60 IU/L, or 50 IU/L.

In a further example, the method of the present application reduces the level of ALT to from about 5 IU/L to about 50 IU/L.

In a further example, the method of the present application reduces the level of AST below 200 IU/L (international units per liter), 150 IU/L, 100 IU/L, 80 IU/L, 60 IU/L, 50 IU/L, or 40 IU/L. In a further example, the method of the present application reduces the level of AST to from about 10 IU/L to about 50 IU/L.

In a further example, the method of the present application reduces the level of GGT below 200 IU/L (international units per liter), 150 IU/L, 100 U/L, 90 IU/L, 80 IU/L, 70 IU/L, or 60 IU/L. In a further example, the method of the present application reduces the level of GGT to from about 15 IU/L to about 50 IU/L or from about 5 IU/L to about 30 IU/L.

In a further example, the method of the present application reduces the level of LDH below 500 IU/L (international units per liter), 400 IU/L, 300 IU/L, 200 IU/L, 180 IU/L, 160 IU/L, 150 IU/L, 140 IU/L, or 130 IU/L. In a further example, the method of the present application reduces the level of LDH to from about 120 IU/L to about 220 IU/L.

In a further example, the method of the present application reduces the level of 5' nucleotidase below 50 IU/L (international units per liter), 40 IU/L, 30 IU/L, 20 IU/L, 18 IU/L, 17 IU/L, 16 LU/L, 15 IU/L, 14 IU/L, 13 IU/L, 12 IU/L, 11 IU/L, 10 IU/L, 9 IU/L, 8 IU/L, 7 IU/L, 6 IU/L, or 5 IU/L. In a further example, the method of the present application reduces the level of 5' nucleotidase to from about 2 IU/L to about 15 IU/L.

The present application also provides a method for reducing glucose levels (i.e., amount of glucose), such as in the blood, comprising administering a therapeutically effective amount of a pharmaceutical composition of the present application to a subject in need thereof. In one example, the method reduces the post-meal glucose levels by at least 10%, 20%, 30%, 40%, 50%, 60%, 70%, 80%, or 90%, as compared to a control subject (e.g., a subject not administered with the composition of the present application). In one example, the subject has elevated levels of post-meal glucose, as compared to a healthy subject (e.g., an individual without a disease or condition, such as those described herein). In one example, the method of the present application reduces the post-meal levels of glucose to normal levels (e.g., similar to the glucose levels in an individual without a disease or condition, such as those described herein). In one example, the method reduces the fasting glucose levels by at least 10%, 20%, 30%, 40%, 50%, 60%, 70%, 80%, or 90%, as compared to a control subject (e.g., a subject not administered with the composition of the present application). In one example, the subject has elevated levels of fasting glucose, as compared to a healthy subject (e.g., an individual without a disease or condition, such as those described herein). In one example, the method of the present application reduces the fasting levels of glucose to normal levels (e.g., similar to the glucose levels in an individual without a disease or condition, such as those described herein).

In one example, the subject has elevated levels of glucose, as compared to a healthy subject (e.g., an individual without a disease or condition, such as those described herein). In one example, the method of the present application reduces post-meal glucose levels below 800 mg/L, 700 mg/L, 600 mg/L, 500 mg/L, 400 mg/L, 350 mg/L, 300 mg/L, 250 mg/L, 240 mg/L, 230 mg/L, 220 mg/L, 210 mg/L, 200 mg/L, 190 mg/L, 180 mg/L, 170 mg/L, 160 mg/L, or 150 mg/L. In one example, the method of the present application reduces post-meal glucose levels below 200 mg/L, 190 mg/L, 180 mg/L, 170 mg/L, 160 mg/L, or 150 mg/L. In one example, the method of the present application reduces fasting glucose levels to 70-800 mg/L, 70-700 mg/L, 70-600 mg/L, 70-500 mg/L, 70-400 mg/L, 70-350 mg/L, 70-300 mg/L, 70-250 mg/L, 70-240 mg/L, 70-230 mg/L, 70-220 mg/L, 70-210 mg/L, 70-200 mg/L, 70-190 mg/L, 70-180 mg/L, 70-170 mg/L, 70-160 mg/L, 70-150 mg/L, 70-140 mg/L, 70-130 mg/L, 70-120 mg/L, 70-110 mg/L, 70-100 mg/L, 90-130 mg/L, 90-120 mg/L, 90-110 mg/L, or 90-100 mg/L. In one example, the method of the present application reduces post-meal glucose levels to 70-200 mg/L, 70-190 mg/L, 70-180 mg/L, 70-170 mg/L, 70-160 mg/L, 70-150 mg/L, 70-140 mg/L, 70-130 mg/L, 70-120 mg/L, 70-110 mg/L, 70-100 mg/L, 90-130 mg/L, 90-120 mg/L, 90-110 mg/L, or 90-100 mg/L.

The present application also provides a method for reducing hemoglobin A1c (HbA1c) levels (i.e., amount of HbA1c), such as in the blood, comprising administering a therapeutically effective amount of a pharmaceutical composition of the present application to a subject in need thereof. In one example, the method reduces the HbA1c levels by at least 10%, 20%, 30%, 40%, 50%, 60%, 70%, 80%, or 90%, as compared to a control subject (e.g., a subject not administered with the composition of the present application). In one example, the subject has elevated levels of HbA1c, as compared to a healthy subject (e.g., an individual without a disease or condition, such as those described herein). In one example, the method of the present application reduces the HbA1c levels to normal levels (e.g., similar to the HbA1c levels in an individual without a disease or condition, such as those described herein).

In one example, the subject has elevated levels of HbA1c, as compared to a healthy subject (e.g., an individual without a disease or condition, such as those described herein). In one example, the method of the present application reduces HbA1c levels below 10%, 9.5%, 9.0%, 8.5%, 8.0%, 7.5%, 7.0%, 6.5%, 6.4%, 6.3%, 6.2%, 6.1%, 6.0%, 5.9%, 5.8%, or 5.7%. In one example, the method of the present application reduces HbA1c levels below 8.0%, 7.9%, 7.8%, 7.7%, 7.6%, 7.5%, 7.4%, 7.3%, 7.2%, 7.1%, 7.0%, 6.9%, 6.8%, 6.7%, 6.6%, 6.5%, 6.4%, 6.3%, 6.2%, 6.1%, 6.0%, 5.9%, 5.8%, or 5.7%. In one example, the method of the present application reduces HbA1c levels below 6.5%, 6.4%, 6.3%, 6.2%, 6.1%, 6.0%, 5.9%, 5.8%, or 5.7%.

The present application also provides a method for increasing insulin secretion (i.e., amount of insulin), comprising administering a therapeutically effective amount of a pharmaceutical composition of the present application to a subject in need thereof. In one example, the method of the present application increases insulin secretion by at least 10%, 20%, 30%, 40%, 50%, 60%, 70%, 80%, or 90%, as compared to a control subject (e.g., a subject not administered with the composition of the present application). In one example, the subject has decreased secretion of insulin, as compared to a healthy subject (e.g., an individual without a disease or condition, such as those described herein). In one example, the method of the present application increases insulin secretion such that the insulin level is of 2-9.0 mIU/mL, 2-8.9 mIU/mL, 2-8.8 mIU/mL, 2-8.7 mIU/mL, 2-8.6 mIU/mL, 2-8.5 mIU/mL, 2-8.4 mIU/mL, 2-8.3 mIU/mL, 2-8.2 mIU/mL, 2-8.1 mIU/mL, 2-8.0 mIU/mL, 2-7.9 mIU/mL, 2-7.8 mIU/mL, 2-7.7 mIU/mL, 2-7.6 mIU/mL, 2-7.5 mIU/mL, 2-7.4 mIU/mL, 2-7.3 mIU/mL, 2-7.2 mIU/mL, 2-7.1 mIU/mL, 2-7.0 mIU/mL, 2-6.9 mIU/mL, 2-6.8 mIU/mL, 2-6.7 mIU/mL, 2-6.6 mIU/mL, 2-6.5 mIU/mL, 2-6.4 mIU/mL, 2-6.3 mIU/mL, 2-6.2 mIU/mL, 2-6.1 mIU/mL, 2-6.0 mIU/mL, 3-9.0 mIU/mL, 3-8.9 mIU/mL, 3-8.8 mIU/mL, 3-8.7 mIU/mL, 3-8.6 mIU/mL, 3-8.5 mIU/mL, 3-8.4 mIU/mL, 3-8.3 mIU/mL, 3-8.2 mIU/mL, 3-8.1 mIU/mL, 3-8.0 mIU/mL, 3-7.9 mIU/mL, 3-7.8 mIU/mL, 3-7.7 mIU/mL, 3-7.6 mIU/mL, 3-7.5 mIU/mL, 3-7.4 mIU/mL, 3-7.3 mIU/mL, 3-7.2 mIU/mL, 3-7.1 mIU/mL, 3-7.0 mIU/mL, 3-6.9 mIU/mL, 3-6.8 mIU/mL, 3-6.7 mIU/mL, 3-6.6 mIU/mL, 3-6.5 mIU/mL, 3-6.4 mIU/mL, 3-6.3 mIU/mL, 3-6.2 mIU/mL, 3-6.1 mIU/mL, 3-6.0 mIU/mL, 4-9.0 mIU/mL, 4-8.9 mIU/mL, 4-8.8 mIU/mL, 4-8.7 mIU/mL, 4-8.6 mIU/mL, 4-8.5 mIU/mL, 4-8.4 mIU/mL, 4-8.3 mIU/mL, 4-8.2 mIU/mL, 4-8.1 mIU/mL, 4-8.0 mIU/mL, 4-7.9 mIU/mL, 4-7.8 mIU/mL, 4-7.7 mIU/mL, 4-7.6 mIU/mL, 4-7.5 mIU/mL, 4-7.4 mIU/mL, 4-7.3 mIU/mL, 4-7.2 mIU/mL, 4-7.1 mIU/mL, 4-7.0 mIU/mL, 4-6.9 mIU/mL, 4-6.8 mIU/mL, 4-6.7 mIU/mL, 4-6.6 mIU/mL, 4-6.5 mIU/mL, 4-6.4 mIU/mL, 4-6.3 mIU/mL, 4-6.2 mIU/mL, 4-6.1 mIU/mL, 4-6.0 mIU/mL, 5-9.0 mIU/mL, 5-8.9 mIU/mL, 5-8.8 mIU/mL, 5-8.7 mIU/mL, 5-8.6 mIU/mL, 5-8.5 mIU/mL, 5-8.4 mIU/mL, 5-8.3 mIU/mL, 5-8.2 mIU/mL, 5-8.1 mIU/mL, 5-8.0 mIU/mL, 5-7.9 mIU/mL, 5-7.8 mIU/mL, 5-7.7 mIU/mL, 5-7.6 mIU/mL, 5-7.5 mIU/mL, 5-7.4 mIU/mL, 5-7.3 mIU/mL, 5-7.2 mIU/mL, 5-7.1 mIU/mL, 5-7.0 mIU/mL, 5-6.9 mIU/mL, 5-6.8 mIU/mL, 5-6.7 mIU/mL, 5-6.6 mIU/mL, 5-6.5 mIU/mL, 5-6.4 mIU/mL, 5-6.3 mIU/mL, 5-6.2 mIU/mL, 5-6.1 mIU/mL, or 5-6.0 mIU/mL.

The present application also provides a method for increasing insulin sensitivity (i.e., decreasing insulin resistance), comprising administering a therapeutically effective amount of a pharmaceutical composition of the present application to a subject in need thereof. In one example, the method of the present application increases insulin sensitivity (i.e., decreases insulin resistance) by at least 10%, 20%, 30%, 40%, 50%, 60%, 70%, 80%, or 90%, as compared to a control subject (e.g., a subject not administered with the composition of the present application). In one example, the subject has decreased insulin sensitivity (i.e., increased insulin resistance), as compared to a healthy subject (e.g., an individual without a disease or condition, such as those described herein).

Insulin sensitivity refers to how sensitive the body is to the effects of insulin. A person said to be insulin sensitive will require smaller amounts of insulin to lower blood glucose levels than someone who has low sensitivity.

Insulin resistance (IR) is a physiological condition in which cells, tissues, or organs fail to respond to the normal actions of the insulin. Accordingly, the cells tissues, or organs in the body become resistant to insulin and are unable to use insulin as effectively as the normal cells, tissues, or organs (e.g., cells, tissues, or organs in a healthy subject).

In one example, the subject is a mammal. In one example, the mammal is human.

In one example, the first compound and one additional therapeutic agent (e.g., additional therapeutic agents described herein) are administered in a two-way combination. In another example, the first compound and two or more additional therapeutic agents (e.g., additional therapeutic agents described herein) are administered in a two-way combination.

The first compound, together with the at least one additional therapeutic agent (e.g., additional therapeutic agents described herein) can achieve synergistic effects, such as synergistic reductions in glucose levels, HbA1c levels, and/or insulin resistance, which may be resistant to individual therapies. Hence, a combination of the first compound and the at least one additional therapeutic agent (e.g., additional therapeutic agents described herein) is advantageous. It can be particularly advantageous for such a combination of the first compound and the at least one additional therapeutic agent (e.g., additional therapeutic agents described herein) to be provided in a single pharmaceutical composition with a pharmaceutical acceptable carrier (such as in a single capsule form) designed to increase compliance and hence effectiveness. Accordingly, the present application further provides a pharmaceutical composition comprising an effective amount of the first compound and an effective amount of the at least one additional therapeutic agent (e.g., additional therapeutic agents described herein), together with one or more pharmaceutically acceptable carriers, diluents, adjuvants or excipients.

In one example, the first compound and the at least one additional therapeutic agent (e.g., additional therapeutic agents described herein) are administered concurrently. For example, the first compound and the at least one additional therapeutic agent (e.g., additional therapeutic agents described herein) are administered together in a single pharmaceutical composition with a pharmaceutical acceptable carrier. In another example, the first compound and the at least one additional therapeutic agent (e.g., additional therapeutic agents described herein) are administered sequentially. For example, the first compound is administered prior or subsequent to the at least one additional therapeutic agent (e.g., additional therapeutic agents described herein).

In one example, the first compound is administered at a first dose for a first time period, followed by administration of the first compound at a second dose for a second time period. In one example, a first compound or a pharmaceutically acceptable salt or amino acid conjugate thereof is administered at a daily total amount from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg for a first time period, followed by administration of the second compound at a daily total amount from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg. In one example, the total amount is orally administered once a day. In one example, the first dose is different from the second dose. In a further example, the first dose is lower than the second dose. In another example, the first dose is higher than the second dose. In one example, the first dose is about 5 mg (e.g., from 4.8 mg to 5.2 mg), and the second dose is about 10 mg (e.g., from 9.8 mg to 10.2 mg). In one example, the first time period is about 6 months. In one example, the second time period is about 6 months.

In one example, the pharmaceutical composition is administered orally, parenterally, or topically. In another example, the pharmaceutical composition is administered orally.

A composition in accordance with the present application will typically contain sufficient first compound or a pharmaceutically acceptable salt or amino acid conjugate thereof, at least one additional therapeutic agent (e.g., additional therapeutic agents described herein) to permit the desired daily dose of each to be administered to a subject in need thereof in a single unit dosage form, such as a tablet or capsule, or in two or more unit dosage forms to be administered simultaneously or at intervals during a day.

In the methods of the present application the active substances may be administered in single daily doses, or in two, three, four or more identical or different divided doses per day, and they may be administered simultaneously or at different times during the day. Usually, the active substances will be administered simultaneously, more usually in a single combined dosage form.

In one aspect, the first compound and the at least one additional therapeutic agent (e.g., additional therapeutic agents described herein) are administered at dosages substantially the same as the dosages at which they are administered in the respective monotherapies. In one aspect, the first compound is administered at a dosage which is less than (e.g., less than 90%, less than 80%, less than 70%, less than 60%, less than 50, less than 40%, less than 30%, less than 20%, or less than 10%) its monotherapy dosage. In one aspect, the at least one additional therapeutic agent (e.g., additional therapeutic agents described herein) is administered at a dosage which is less than (e.g., less than 90%, less than 80%, less than 70%, less than 60%, less than 50, less than 40%, less than 30%, less than 20%, or less than 10%) its monotherapy dosage. In one aspect, both the first compound and the at least one additional therapeutic agent (e.g., additional therapeutic agents described herein) are administered at a dosage which is less than (e.g., less than 90%, less than 80%, less than 70%, less than 60%, less than 50, less than 40%, less than 30%, less than 20%, or less than 10%) their respective monotherapy dosages.

A pharmaceutical composition of the present application may be in any convenient form for oral administration, such as a tablet, capsule, powder, lozenge, pill, troche, elixir, lyophilized powder, solution, granule, suspension, emulsion, syrup or tincture. Slow-release or delayed-release forms may also be prepared, for example in the form of coated particles, multi-layer tablets, capsules within capsules, tablets within capsules, or microgranules.

Solid forms for oral administration may contain pharmaceutically acceptable binders, sweeteners, disintegrating agents, diluents, flavoring agents, coating agents, preservatives, lubricants and/or time delay agents. Suitable binders include gum acacia, gelatin, cornstarch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange or raspberry flavoring. Suitable coating agents include polymers or copolymers or acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropyl methylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further include one or more emulsifying agents. Suitable emulsifying agents include dispersing agents as exemplified above or natural gums such as gum acacia or gum tragacanth.

Pharmaceutical compositions of the present application may be prepared by blending, grinding, homogenizing, suspending, dissolving, emulsifying, dispersing and/or mixing the first compound or its pharmaceutically acceptable salt or amino acid conjugate and at least one additional therapeutic agent, together with the selected excipient(s), carrier(s), adjuvant(s) and/or diluent(s). One type of pharmaceutical composition of the present application in the form of a tablet or capsule may be prepared by (a) preparing a first tablet comprising at least one of the active substances selected from the first compound or a pharmaceutically acceptable salt or amino acid conjugate thereof and at least one additional therapeutic agent together with any desired excipient(s), carrier(s), adjuvant(s) and/or diluent(s), and (b) preparing a second tablet or a capsule, wherein the second tablet or the capsule includes the remaining active substance(s) and the first tablet. Another type of pharmaceutical composition of the present application in the form of a capsule may be prepared by (a) preparing a first capsule comprising at least one of the active substances selected from the first compound or a pharmaceutically acceptable salt or amino acid conjugate thereof and the additional therapeutic agent(s), together with any desired excipient(s), carrier(s), adjuvant(s) and/or diluent(s), and (b) preparing a second capsule, wherein the second capsule includes the remaining active substance(s) and the first capsule. A further type of pharmaceutical composition of the present application in the form of a tablet may be prepared by (a) preparing a capsule comprising at least one of the active substances selected from a first compound or a pharmaceutically acceptable salt or amino acid conjugate thereof and at least one additional therapeutic agent, together with any desired excipient(s), carrier(s), adjuvant(s) and/or diluent(s), and (b) preparing a tablet, wherein the tablet includes the remaining active substance(s) and the capsule.

In example s, the at least one additional therapeutic agent (e.g., additional therapeutic agents described herein) is used either as an immediate release tablet or as a sustained release tablet. It is particularly effective when provided in a sustained release tablet. Sustained release tablets of the various additional therapeutic agents are commercially available. It is preferable for prolonged action that the tablet is in a sustained release format.

In another example, the pharmaceutical composition of the present application comprises a capsule containing at least one additional therapeutic agent (e.g., additional therapeutic agents described herein) within a capsule containing a first compound or a pharmaceutically acceptable salt or amino acid conjugate thereof. Typically in this form the at least one additional therapeutic agent (e.g., additional therapeutic agents described herein) is presented in an immediate release form. In that event it is usual to administer the composition three times daily. Another mode of administration is to provide a composition containing at least one additional therapeutic agent (e.g., additional therapeutic agents described herein) in either a sustained release or a non-sustained release form as described above, twice daily, wherein the daily amount of the composition administered contains sufficient amount of the active substances to provide the desired daily dosage to the patient.

In one example, the pharmaceutical compositions of the application is a dosage form which comprises a first compound or a pharmaceutically acceptable salt or amino acid conjugate thereof in a daily total amount of from 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, or 5-25 mg.

The pharmaceutical composition of the present application can be used lifelong by the patient and prolonging survival. The reduction of glucose in the blood, increase in insulin secretion, and/or decrease in insulin resistance ensures reduction in the development of associated diseases, such as diabetes and obesity. The combination of the first compound and the at least one additional therapeutic agent (e.g., additional therapeutic agents described herein) is likely to be the therapy of choice for primary biliary cirrhosis (PBC) with hyperglycemia and for resistant primary biliary cirrhosis (PBC). Because of the simplified dosing provided by the present application, a combined therapy of the present application can be used in increasing doses, depending on a patient's weight and clinical response.

The first compounds disclosed herein can be prepared by the conventional methods (e.g., those described in U.S. Publication No. 2009/0062526, U.S. Pat. No. 7,138,390, and WO 2006/122977), such as by a 6-step synthesis followed by one purification step to produce highly pure Compound 1 (obeticholic acid, or OCA) as shown in Scheme 1 below.

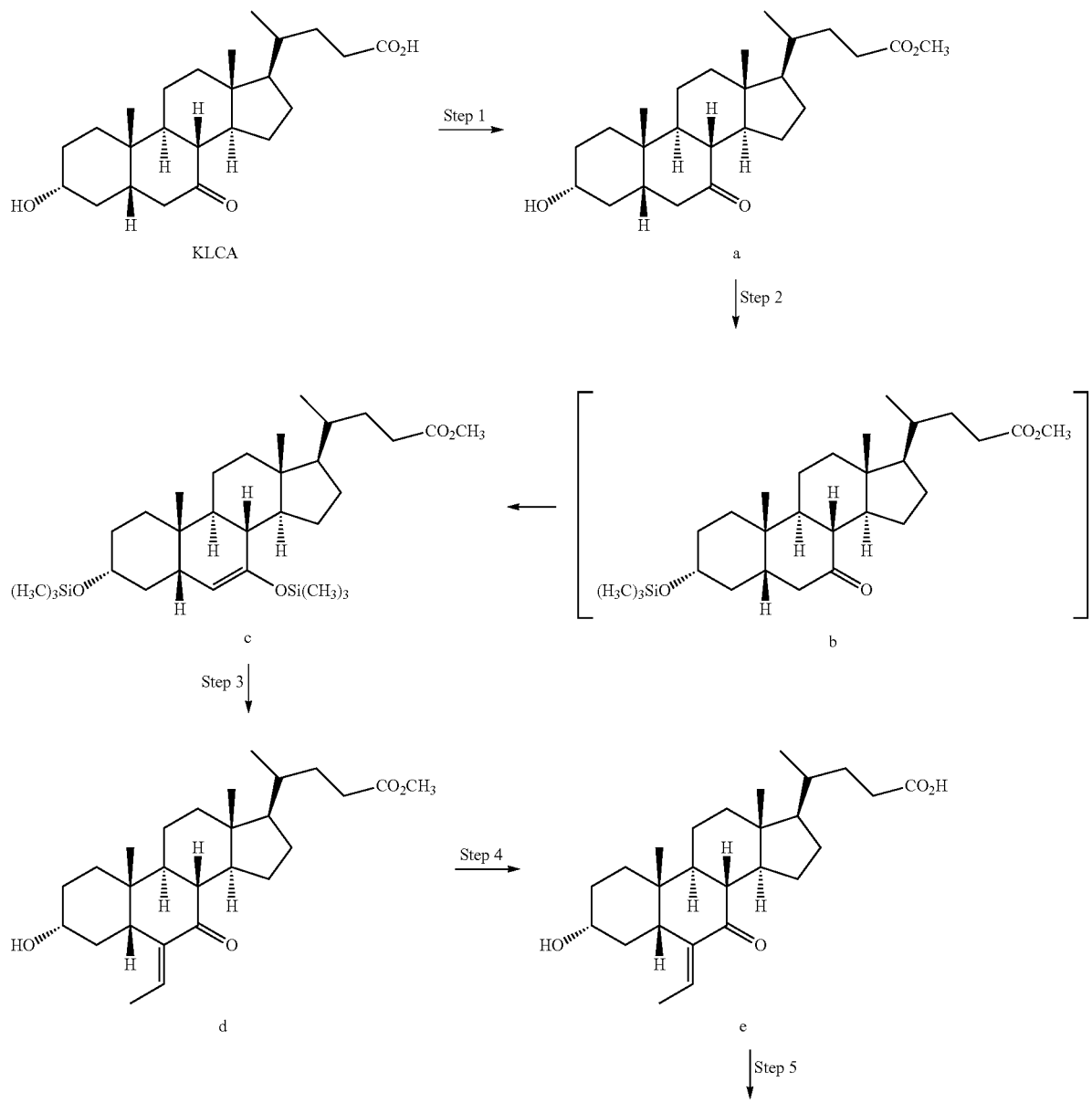

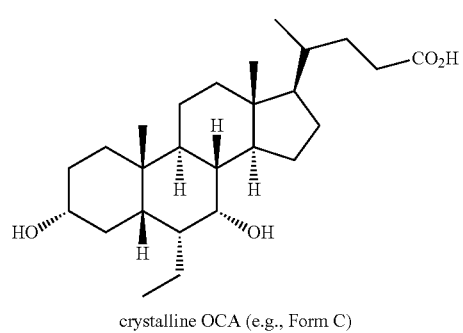

crystalline OCA (e.g., Form C)

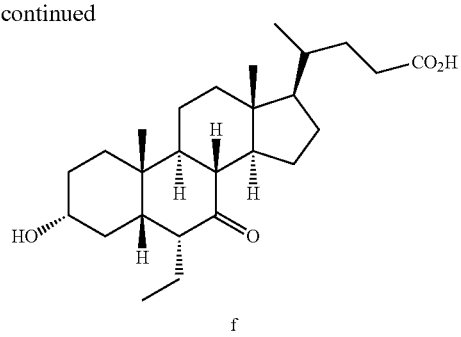

f

Step 6

Step 7

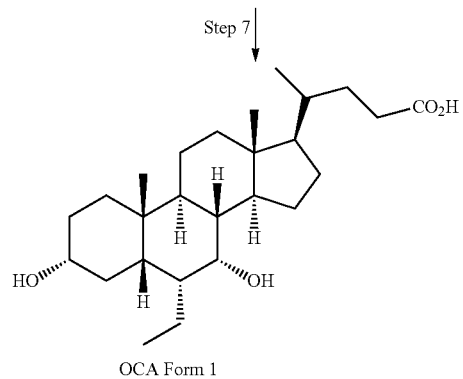

OCA Form 1

The process above was described in WO 2013/192097, the contents of which are incorporated herein by reference in their entirety. The process is a 6-step synthesis followed by one purification step. Step 1 is the esterification of the C-24 carboxylic acid of 7-keto lithocholic acid (KLCA) using methanol in the presence of acidic catalysis and heat to produce the methyl ester compound a. Step 2 is silylenol ether formation from compound 1 using a strong base followed by treatment with chlorosilane to produce compound c. Step 3 is an aldol condensation reaction of the silylenol ether compound c and acetaldehyde to produce compound d. Step 4 is saponification of the C-24 methyl ester of compound d to produce compound e. Step 5 is the hydrogenation of the 6-ethylidene moiety of compound e to produce compound f. Step 6 is the selective reduction of the 7-keto group of compound f to a 7α-hydroxy group to produce crystalline Compound 1. Step 7 is the conversion of crystalline compound to Compound 1 (obeticholic acid Form 1, or OCA Form 1).

The biological and/or therapeutic activities of the pharmaceutical composition of the present application can be measured by the conventional methods known in the art. Without limiting the disclosure of the present application, some suitable methods are provided herein.

Isolation of Hepatocytes

A two-step in sim collagenase perfusion method can be utilized to isolate hepatocytes. Hepatocytes are isolated from a suitable animal (e.g., mouse, rat, rabbit, pig). After proper perfusion, the liver is dissected and transferred to perfusion buffer. The resulting cell suspension is filtered and collected. Hepatocytes are separated (e.g., by using a Percoll density centrifugation technique)

Sandwich Culture of Hepatocytes

Isolated hepatocytes are cultured on collagen-coated tissue culture plates and maintained in culture medium supplemented with serum, penicillin, streptomycin, epidermal growth factor, insulin, glucagon and hydrocortisone. For the sandwich system, an additional collagen gel solution is distributed over the cells. The culture plates are incubated at 37° C. to allow gelation and attachment of the second gel layer. The culture medium is changed daily and stored at −20° C. for further analysis. The pharmaceutical composition of the present application is applied to the hepatocytes, and the effects on the cells are subsequently measured.

Hepatocyte Suspension Cultures

Immediately after the isolation, hepatocytes are washed and resuspended. The suspended cells are cultured in the absence or presence of the pharmaceutical composition of the present application. Positive controls (e.g., cells cultured in the presence of glucacon) can be included.

After the incubation period, glucose released into the medium will be determined (e.g., with the glucose-oxidase method using a Trinder assay kit (Sigma)).

In addition, glucose utilization can be determined as the production of tritiated water (as for fatty acid oxidation experiments) after incubation of hepatocytes in the presence of [5-$^3$H]-glucose. Uptake of 2-[$^3$H]-deoxyglucose is determined with or without insulin (Perdomo et al., *J. Biol. Chem.* 279, 27177 (2004)). Incorporation of D-[$^{14}$C]-glucose into glycogen can be measured in the absence or presence of insulin (Perdomo et al. 2004).

HepG2 Cell Culture

Human hepatoblastoma cells (HepG2) are grown in culture medium as described (Wang et al., *Mol. Endocrinol.* 22, 1622 (2008)). The following day, cells are treated with the pharmaceutical composition of the present application. After treatment, the cells are treated with TPA, LPS, or TNF-α and then collected for RNA isolation.

Transient transfection of HepG2 cells will be performed (e.g., by using Lipofectamine 2000 (Invitrogen, Carlsbad, Calif.)). Twenty-four hours after transfection, cells are pretreated with the pharmaceutical composition of the present application. Cells are subsequently treated with or without LPS or TPA. Cells are then harvested and the luciferase activity will be determined using a dual-luciferase reporter assay system.

Vice Model

Mice (e.g., wild-type or FXWV) are maintained in a pathogen-free animal facility under a standard 12:12-hour light/dark cycle. Mice are fed standard rodent chow and water ad libitum. Mice are fasted overnight and then injected intraperitoneally with a single dose of LPS, or phosphate-buffered saline (PBS), or the pharmaceutical composition of the present application, followed by feeding water ad libitum. After the injection, mice are killed, and blood and livers are removed for further analysis. All procedures followed National Institutes of Health guidelines for the care and use of laboratory animals.

MetS Rabbit Model

The HFD-induced rabbit model of MetS are obtained as described previously (Filippi et al., J. Sexual Med. 6, 3274 (2009)). Male New Zealand White rabbits are randomly numbered and assigned to two different groups: untreated group, fed a control diet (CON), or treated group, fed a HFD (e.g., 0.5% cholesterol and 4% peanut oil), for 12 weeks. A subgroup of HFD rabbits are treated with the pharmaceutical composition of the present application.

Blood samples are obtained at baseline and at week 12. After 12 weeks of treatment, the rabbits are killed, and the specimens of the liver, VAT (accumulated between the intestinal loops and mesentery), and gallbladder are excised, weighed, collected, and processed for the subsequent analyses. VAT samples from all the rabbit groups are also processed for the isolation of preadipocytes. Biochemical and hormonal serum analyses are performed as described previously (Filippi et al. 2009, Morelli et al., J. Steroid Biochem. Mol. Biol. 132, 80 (2012), Vignozzi et al., J. Endocrinology 212, 71 (2012)).

To evaluate the effects of MetS, an algorithm taking into account the presence, as a dummy variable, of one or more of the following factors: hyperglycemia, high triglyceride levels, high cholesterol levels, increased blood pressure, and visceral fat accumulation, is designed. Cut-offs for each factor are derived by the mean±2 S.D. of the analyzed parameter, as measured in the CON rabbits. Positivity for three or more factors indicates MetS.

Histomorphometric Analysis of VAT

VAT specimens are analyzed by hematoxylin and eosin staining to measure adipocyte diameter, as described previously (Maneschi et al. 2012).

Hypoxia Detection and Immunohistochemistry

VAT oxygenation is analyzed using the bio-reductive drug pimonidazole hydrochloride, injected i.p. before killing, as described previously (Maneschi et al. 2012, Morelli et al. 2012, 2013, Vignozzi et al. 2012).

Preparation of Total and Membrane/Cytosolic Fractions

For protein extraction from the VAT samples, the frozen tissues are ground in liquid nitrogen and divided into two aliquots: one for total protein extraction and the other for membrane/cytosolic preparations. Membrane and cytosolic fractions are prepared. Protein extracts are quantified with the BCA reagent (Pierce, Rockford, Ill., USA), and resolved by SDS-PAGE. Western blot analysis is performed as described previously (Maneschi et al. 2012).

Liver Histology

Liver steatosis is assessed by Oil Red O staining of the liver sections. Frozen sections are cut in a cryostat and fixed and stained with Oil Red O. After Oil Red O staining, the sections are washed and stained with hematoxylin and eosin to highlight the hepatocyte nuclei. Finally, the sections are photographed, and computer-assisted quantification of Oil Red O positivity is done after background subtraction using the Adobe Photoshop Software.

Immunohistochemistry for Inflammatory Markers in the Liver Sections

Liver sections are incubated with primary antibodies against various inflammatory markers (e.g., TNFα, Cd68, Il-6, Il-1b, and Il-12). The sections are rinsed and incubated with a biotinylated secondary antibody and then with a streptavidin-biotin-peroxidase complex. The reaction product is developed with 3',3'-diaminobenzidine tetrahydrochloride as the chromogen (Sigma-Aldrich). Control experiments are performed by omitting the primary antibody. Computer-assisted quantification of the staining against inflammatory markers is done after background subtraction using the Adobe Photoshop Software.

Isolation, Characterization, and Differentiation of Rabbit Visceral Fat Preadipocytes The isolation of rabbit preadipocytes (rPADs) from VAT is carried out as described previously (Maneschi et al. 2012). The cells are cultured in a complete culture medium. P1 cultures are used. rPADs are characterized by flow cytometry with various monoclonal antibodies (e.g., CD34-PE, CD45-FITC, CD31-FITC, CD14-PE, CD90-PE, CD106-FITC, and CD105-PE, as described previously (Maneschi et al. 2012). The differentiation of rPADs, 2 days after confluence, is induced by exposing them to a differentiation mixture (DIM) (e.g., a mixture containing 5 mg/ml insulin, 1 mM dexamethasone, and 0.5 mM 3-isobutyl-1-methylxanthine (IBMX) in 5% stripped FBS-supplemented DMEM).

Glucose Uptake

Glucose uptake by rPADs is measured as described previously (Maneschi et al. 2012). DIM-exposed rPADs are cultured for 24 h in a serum-free medium, followed by incubation in increasing concentrations of insulin to evaluate insulin-dependent stimulation. At the end of the incubation period, rPADs are further incubated with $^3$H-2-deoxy-D-glucose. Incorporated radioactivity is measured by scintillation spectrometry using.

Experimental Animals and Diets

Animals are housed individually in standard cages at 22° C. in a 12:12-h light-dark cycle. Mice can be purchased (e.g., from The Jackson Laboratory (Bar Harbour, Me.)). Male GLP-1 receptor-deficient (GLP-IRKO) mice are derived from heterozygous mating pairs (Scrocchi et al., Nat. Med. 2, 1254 (1996)). To induce NASH, two diets comprised of high fat, high fructose, and high cholesterol, are tested, where the source of fat will be either trans-fat or lard. A low-fat diet with no fructose or cholesterol is used as a control diet.

Studies and Drug Administration

To characterize the development of NASH, $Lep^{ob}/Lep^{ob}$ or B6 mice either a low-fat diet (LFD), the high trans-fat, high fructose, high cholesterol (HTF) diet, or the high lard fat, high fructose, high cholesterol diet (HLF) diet are maintained (e.g., for 8 or 12 weeks). Mice are implanted subcutaneously with a single osmotic minipump delivering either vehicle (e.g., 50% DMSO in sterile water) or a pharmaceutical composition of the present application. In addition or alternatively, mice may have either vehicle or a pharmaceutical composition of the present application administered once daily via oral gavage.

To assess the impact of body weight loss on hepatic endpoints the initial study in $Lep^{ob}/Lep^{ob}$ mice exposed to LFD or HTF diet as described above can be repeated. After 8 weeks on LFD or HTF diet, all mice are implanted with an osmotic minipump delivering either vehicle or a pharmaceutical composition of the present application. In addition or alternatively, mice may have either vehicle or a pharmaceutical composition of the present application administered once daily via other routes of administration, such as oral gavage. A subset of the HTF group are implanted with a vehicle containing minipump and are calorie restricted to elicit a similar degree of weight loss as that observed in drug-treated mice.

Histological and Biochemical Analyses of Liver Tissue

At termination, liver tissue is excised and fixed (e.g., in 10% neutral-buffered formalin). Liver tissue is paraffin-embedded, sectioned, and mounted and stained with hematoxylin and eosin. To visualize fibrosis, another set of sections are stained with Masson trichrome stain. Sections are first stained with Weigert's iron hematoxylin, followed by Biebrich scarlet, phosphotungstic/phosphomolybdic acid, and aniline blue treatment. A second set of sections are immunostained using an antibody targeted to the macrophage marker Mac-2. All histological analyses are conducted by a pathologist blinded to the treatment conditions.

Plasma Hormone and Metabolite Analyses

Plasma glucose, triglyceride, total cholesterol, ALT, and aspartate aminotransferase (AST) levels are measured (e.g., by using an Olympus AU400e Bioanalyzer (Olympus America Diagnostics, Center Valley, Pa.)). Plasma samples are diluted 1:10 with PBS for detection of ALT and AST within the range of the standard curve. Total plasma adiponectin is measured (e.g., by using a commercially available ELISA according to manufacturer's instructions (Millipore, Billerica, Mass.)).

Definitions

For convenience, certain terms used in the specification, examples and appended claims are collected here.

As used herein, the term "FXR agonist" refers to any compound which activates FXR. In one aspect, an FXR agonist achieves at least 50% activation of FXR relative to CDCA, the appropriate positive control in the assay methods described in WO 2000/037077. In another aspect, an FXR agonist achieves 100% activation of FXR in the scintillation proximity assay or the HTRF assay as described in WO2000/037077. Examples of FXR agonists include but are not limited to those described in U.S. Pat. Nos. 7,138,390; 7,932,244; 20120283234; 20120232116; 20120053163; 20110105475; 20100210660; 20100184809; 20100172870; 20100152166; 20100069367; 20100063018; 20100022498; 20090270460; 20090215748; 20090163474; 20090093524; 20080300235; 20080299118; 20080182832; 20080039435; 20070142340; 20060069070; 20050080064; 20040176426; 20030130296; 20030109467; 20030003520; 20020132223; and 20020120137.

As used herein, the term "obeticholic acid" or "OCA" refers to a compound having the chemical structure:

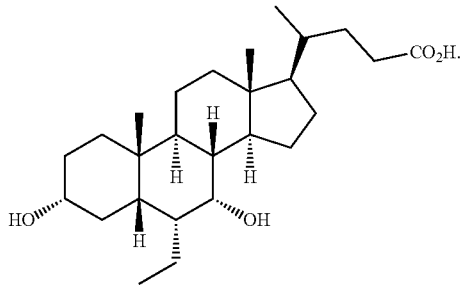

Obeticholic acid is also referred to as obeticholic acid Form 1, INT-747, 3α,7α-dihydroxy-6α-ethyl-5β-cholan-24-oic acid, 6α-ethyl-chenodeoxycholic acid, 6-ethyl-CDCA, 6ECDCA, cholan-24-oic acid,6-ethyl-3,7-dihydroxy-,(3α, 5β, 6α,7α), and can be prepared by the methods described in U.S. Publication No. 2009/0062526 A1, U.S. Pat. No. 7,138,390, and WO2006/122977. The CAS registry number for obeticholic acid is 459789-99-2.

As used herein, the term "crystalline obeticholic acid" refers to any crystalline form of a compound having the chemical structure:

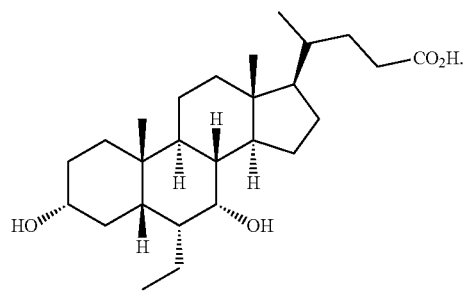

Crystalline obeticholic acid means that the compound is crystallized into a specific crystal packing arrangement in three spatial dimensions or the compound having external face planes. The solid form of obeticholic acid can crystallize into different crystal packing arrangements, all of which have the same elemental composition of obeticholic acid. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystals of obeticholic acid can be prepared by crystallization under different conditions, e.g., different solvents, temperatures, etc. Examples of crystalline forms of OCA are described in co-pending U.S. Pub. No. 20130345188.

The term "first compound" means a compound of formula I or Compound 1, or a pharmaceutically acceptable salt or amino acid conjugate thereof. Whenever the term is used in the context of the present application it is to be understood that the reference is being made to the free base, an isotopically-labeled compound, a crystalline compound, or a corresponding pharmaceutically acceptable salt or amino acid conjugate thereof, provided that such is possible and/or appropriate under the circumstances.

As used herein, the term "amino acid conjugates" refers to conjugates of a first compound of the present application (e.g., a compound of Formula I) with any suitable amino acid. For example, such a suitable amino acid conjugate of a compound of Formula I will have the added advantage of enhanced integrity in bile or intestinal fluids. Suitable amino acids include but are not limited to glycine, sarcosine, and taurine. Thus, the present application encompasses the glycine, sarcosine, and taurine conjugates of a first compound of the present application (e.g., Compound 1).

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms, or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

"Disease state" means any disease, disorder, condition, symptom, or indication.

The term "effective amount" or "therapeutically effective amount" as used herein refers to an amount of a first compound (e.g., an FXR-activating ligand), or at least one additional therapeutic agent (e.g., additional therapeutic agents described herein), that produces an acute or chronic therapeutic effect upon appropriate dose administration, alone or in combination. In one example, an effective amount or therapeutically effective amount of a first compound (e.g., an FXR-activating ligand) produces an acute or chronic therapeutic effect upon appropriate dose administration in combination with at least one additional therapeutic agent (e.g., additional therapeutic agents described herein). The effect includes the prevention, correction, inhibition, or reversal of the symptoms, signs and underlying pathology of a disease/condition (e.g., fibrosis of the liver, kidney, or intestine) and related complications to any detectable extent. An "effective amount" or "therapeutically effective amount" will vary depending on the first compound, the additional therapeutic agent (e.g., additional therapeutic agents described herein), the disease and its severity, and the age, weight, etc., of the subject to be treated.

A therapeutically effective amount of a first compound can be formulated together with one or more additional therapeutic agents (e.g., additional therapeutic agents described herein), and optionally one or more pharmaceutically acceptable carriers for administration to a human or a non-human animal. Accordingly, the pharmaceutical composition of the application can be administered, for example, via oral, parenteral, or topical routes, to provide an effective amount of the first compound and the additional therapeutic agents (e.g., additional therapeutic agents described herein). In alternative examples, the compositions of the application can be used to coat or impregnate a medical device, e.g., a stent.

"Pharmacological effect" as used herein encompasses effects produced in the subject that achieve the intended purpose of a therapy. In one example, a pharmacological effect means that primary indications of the subject being treated are prevented, alleviated, or reduced. For example, a pharmacological effect would be one that results in the prevention, alleviation or reduction of primary indications in a treated subject. In another example, a pharmacological effect means that disorders or symptoms of the primary indications of the subject being treated are prevented, alleviated, or reduced. For example, a pharmacological effect would be one that results in the prevention, alleviation or reduction of the disorders or symptoms in a treated subject.

It is to be understood that the isomers arising from asymmetric carbon atoms (e.g., all enantiomers and diastereomers) are included within the scope of the application, unless indicated otherwise. Such isomers can be obtained in substantially pure form by classical separation techniques and by stereochemically controlled synthesis.

A "pharmaceutical composition" is a formulation containing therapeutic agents such as a first compound and at least one additional therapeutic agent (e.g., additional therapeutic agents described herein), in a form suitable for administration to a subject. In one example, the pharmaceutical composition is in bulk or in unit dosage form. It can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the application are dictated by and directly dependent on the unique characteristics of the active agents and the particular therapeutic effect to be achieved, and the limitations inherent in the art of compounding such an active agent for the treatment of individuals.

The term "unit dosage form" refers to physically discrete units suitable as unitary dosages for humans and other mammals, each unit containing a predetermined quantity of active material calculated to produce the desired therapeutic effect, in association with a suitable pharmaceutical excipient as described herein.

The unit dosage form is any of a variety of forms, including, for example, a capsule, an IV bag, a tablet, a single pump on an aerosol inhaler, or a vial. The quantity of first compound or a pharmaceutically acceptable salt or amino acid conjugate thereof in a unit dose of composition is an effective amount and is varied according to the particular treatment involved and/or the additional therapeutic agent(s) used for the treatment. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one example, the first compound and/or the at least one additional therapeutic agent is mixed under sterile conditions with a pharmaceutically acceptable carrier, and with any preservatives, buffers, or propellants that are required.

As used herein, "PO" or "per os" refers to oral administration; "SQ" refers to subcutaneous administration; and "QD" refers to once daily administration.

The term "flash dose" refers to formulations that are rapidly dispersing dosage forms.

The term "immediate release" is defined as a release of a therapeutic agent (such as a first compound or at least one additional therapeutic agent) from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a therapeutic agent from a dosage form over a prolonged period.

A "subject" includes mammals, e.g., humans, companion animals (e.g., dogs, cats, birds, and the like), farm animals (e.g., cows, sheep, pigs, horses, fowl, and the like), and laboratory animals (e.g., rats, mice, guinea pigs, birds, and the like). In one example, the subject is human. In one aspect, the subject is female. In one aspect, the subject is male.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier or excipient" means a carrier or excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

While it is possible to administer the first compound directly without any formulation, the first compound may be administered in the form of a pharmaceutical formulation comprising a pharmaceutically acceptable excipient. This formulation can be administered by a variety of routes including oral, buccal, rectal, intranasal, transdermal, subcutaneous, intravenous, intramuscular, and intranasal.

In one example, the first compound and/or the at least one additional therapeutic agent (e.g., additional therapeutic agents described herein) can be administered transdermally. In order to administer transdermally, a transdermal delivery device ("patch") is needed. Such transdermal patches may be used to provide continuous or discontinuous infusion of a compound of the present application in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

In one example, the pharmaceutical composition of the present application is adapted for buccal and/or sublingual, or nasal administration. This example provides administration of the first compound in a manner that avoids gastric complications, such as first pass metabolism by the gastric system and/or through the liver. This administration route may also reduce adsorption times, providing more rapid onset of therapeutic benefits.

The first compound may be administered over a wide dosage range. For example, dosages per day normally fall within the range of about 0.0001 to about 30 mg/kg of body weight. In the treatment of adult humans, the range of about 0.1 to about 15 mg/kg/day, in single or divided dose, is used. In one example, the formulation comprises about 0.1 mg to about 1500 mg of a first compound. In another example, the formulation comprises about 1 mg to about 100 mg of a first compound. In another example, the formulation comprises about 1 mg to about 50 mg of a first compound. In another example, the formulation comprises about 1 mg to about 30 mg of a first compound. In another example, the formulation comprises about 4 mg to about 26 mg of a first compound. In another example, the formulation comprises about 5 mg to about 25 mg of a first compound. In another example, the formulation comprises about 5 mg, about 10 mg, about 15 mg, about 20 mg, about 25 mg, about 30 mg, about 35 mg, about 40 mg, about 45 mg, or about 50 mg of a first compound. However, it will be understood that the amount of the first compound actually administered will be determined by a physician, in the light of the relevant circumstances, including the condition to be treated, the chosen route of administration, the form of the first compound administered, the additional therapeutic agent(s) administered, the age, weight, and response of the individual patient, and the severity of the patient's symptoms. Therefore, the above dosage ranges are not intended to limit the scope of the application in any way. In some instances dosage levels below the lower limit of the aforesaid range may be more than adequate, while in other cases still larger doses may be employed without causing any harmful side effect, provided that such larger doses are first divided into several smaller doses for administration throughout the day.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what an abnormally elevated blood level is for each of the markers. For example, a patient suffering from a cholestatic condition generally has greater than about 125 IU/L alkaline phosphatase, greater than about 65 IU/L GGT, and greater than about 17 NIL 5"nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "primary biliary cirrhosis", is used interchangeably with the term "primary biliary cholangitis", and is often abbreviated PBC. PBC is an autoimmune disease of the liver marked by the slow progressive destruction of the small bile ducts of the liver, with the intralobular ducts (Canals of Hering) affected early in the disease. When these ducts are damaged, bile builds up in the liver (cholestasis) and over time damages the tissue. This can lead to scarring, fibrosis and cirrhosis. Primary biliary cirrhosis is characterized by interlobular bile duct destruction. Histopathologic findings of primary biliary cirrhosis include: inflammation of the bile ducts, characterized by intraepithelial lymphocytes, and periductal epithelioid granulomata. There are 4 stage of PBC.

Stage 1—Portal Stage: Normal sized triads; portal inflammation, subtle bile duct damage. Granulomas are often detected in this stage.

Stage 2—Periportal Stage: Enlarged triads; periportal fibrosis and/or inflammation. Typically this stage is characterized by the finding of a proliferation of small bile ducts.

Stage 3—Septal Stage: Active and/or passive fibrous septa.

Stage 4—Biliary Cirrhosis: Nodules present; garland

The term "primary sclerosing cholangitis" (PSC) is a disease of the bile ducts that causes inflammation and subsequent obstruction of bile ducts both at a intrahepatic (inside the liver) and extrahepatic (outside the liver) level. The inflammation impedes the flow of bile to the gut, which can ultimately lead to cirrhosis of the liver, liver failure and liver cancer.

The term "nonalcoholic steatohepatitis" (NASH) is liver inflammation caused by a buildup of fat in the liver. In some people, the buildup of fat causes inflammation of the liver. Because of the inflammation, the liver doesn't work as well as it should. NASH can get worse and cause scarring of the liver, which leads to cirrhosis. NASH is similar to the kind of liver disease that is caused by long-term, heavy drinking. But NASH occurs in people who do not abuse alcohol.

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the compositions and methods of the present application can be practiced in a variety of example s and that the description and examples provided herein are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art. In the case of conflict, the present specification will control. All percentages and ratios used herein, unless otherwise indicated, are by weight.

EXAMPLES

Example 1: Diet-Induced Obese NASH in C57BL/6j Mice

Figure 17:
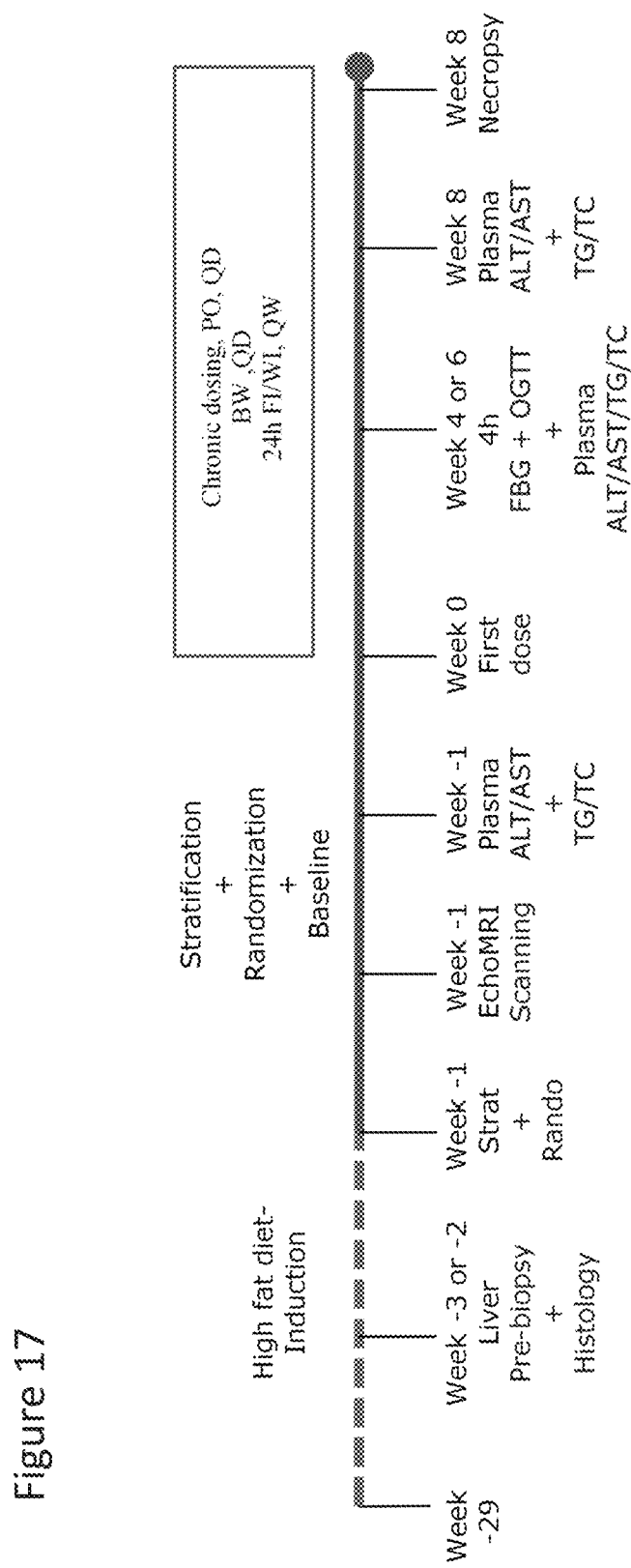
FIG. 17 is the outline of a study of Diet-Induced Obese NASH in C57BL/6j mice.

The studies were conducted to evaluate the effects of obeticholic acid (OCA) and a therapeutic agent that decreases blood glucose level, stimulates insulin secretion, and/or increases insulin sensitivity, alone or in combination, on metabolic parameters, hepatic pathology, and NAS activity score in diet induced obese NASH mice. The therapeutic agents used in Examples 2, 3, and 4 were liraglutide (LIRA), metformin (MET), or sitagliptin (SIT), respectively. In one study, the anti-glycemic agent is empagliflozin (EMP). Additionally, hepatic gene expression profiling and subsequent pathway analysis were performed to determine whether the combination regulates novel genes not regulated by either monotherapy treatment, and/or more strongly regulates genes also impacted by the monotherapy. The study outline is shown in FIG. 17.

Animals, Housing and Diet

At 5 weeks of age, male C57BL/6 mice were purchased from JanVier, France, and transferred to the test stables. During the acclimatization and high fat diet-induction period, the mice were group housed five per cage in custom-made cabinets under a 12:12 hour light-dark cycle (lights on from 3 AM-3 PM) at controlled temperature conditions (22±1° C.; 50±10% relative humidity). Throughout the diet-induction and study period, the mice had ad libium access to the high fat diet (n=110, DIO-NASH) (D09100301, Research Diet, USA) (40% fat (18% trans-fat), 40% carbohydrates (20% fructose) and 2% cholesterol) or regular rodent chow (n=10, LEAN-CHOW) (Altromin 1324, Brogaarden, Denmark), and tap water. The animals were kept on the diet for 28 weeks before experimentation and maintained on the diet throughout the study period. During post-operative recovery and throughout the study period, all animals were single-housed.

Allocation into Studies, Stratified Randomization and Baseline Monitoring

After 27 weeks of diet-induction, a liver biopsy was obtained for hepatic progression of steatosis by histological assessment. At week −2 (SIT combination) or −1 (LIRA and MET combination) prior to dosing, a stratified randomization into treatment groups was performed according to steatosis score and body weight. Animals were scanned using EchoMRI (EchoMRI, USA) to determine body composition analysis. The EchoMRI scan measures fat and fat-free tissue mass. Blood samples were collected from the cheek (submandibular) in a non-fasting and conscious state for baseline plasma analysis of ALT, AST, TG and TC levels.

Pre-Biopsy Procedure

On the day of operating procedure, mice were anesthetized with isoflurane (2-3%) in 100% oxygen. A small abdominal incision in the midline was made and the left lateral lobe of the liver was exposed. A cone shaped wedge of liver tissue (~100 mg) was excised from the distal portion of the lobe, weighed, and fixated in 4% paraformaldehyde (PFA) for histology. The cut surface of the liver was instantly electrocoagulated using bipolar coagulation (ERBE VIO 100 electrosurgical unit). The liver was returned to the abdominal cavity and the abdominal wall was sutured and the skin is closed with staplers. For post-operative recovery mice were given carprofen (5 mg/ml- 0.01 ml/10 g) and enrofloxazin (5 mg/ml-1 ml/kg) administered subcutaneously on the day of the operation procedure and post-operation day 1 and 2. Liver biopsy preparation for histological assessment: After overnight storage in 4% PFA, liver biopsies were infiltrated overnight in paraffin in an automated Miles Scientific Tissue-TEK VIP Tissue Processor and subsequently embedded in paraffin blocks. Biopsies from five different animals were embedded on one block. The blocks were then trimmed and two 3 µm sections were cut (for H&E staining) on a Microm HM340E Microtome (Thermo Scientific). Two blocks were placed on one slide giving a total of 10 biopsies per slide representing 10 different animals. Sections were left to dry overnight. Evaluation of steatosis degree for stratification and randomization into treatment groups was performed as outlined by Kleiner et al. (2005) by a histologist blinded to the treatment conditions.

Blood and Plasma Analyses

Blood samples were collected into 10 µL heparinized glass capillary tubes. The sample was immediately suspended in buffer (0.5 ml of glucose/lactate system solution (EKF-diagnostics, Germany) and analyzed for glucose on the test day using a BIOSEN c-Line glucose meter (EKF-diagnostics, Germany). For triglyceride and cholesterol content, 100 µl blood was collected into Lithium-Heparin tubes. Plasma was separated and samples were stored at 4° C. for one day prior to analysis.

Oral Glucose Tolerance Test (OGTT)

In week 4 (LIRA and MET combinations) or week 6 (SIT combination) of treatment, an OGTT was performed in conscious free-moving animals. Latest drug dose was administered about 18 hours before OGTT and animals did not receive drug dosing prior to test. Animals were fasted for 4 h prior to test start (food removal from 6 AM to 10 AM). At t=0, mice received an oral bolus of glucose (2 g/kg) (200 mg/ml; Fresenius Kabi, Sweden) by oral gavage (10 ml/kg). Blood samples were collected from the tail vein (by snipping) and blood glucose was measured at time point 0, 15, 30, 60 and 120 minutes after the oral glucose administration. Mice were re-fed after the blood sampling and drug dosed as per usual.

Termination and Necropsy

Animals were terminated in week 8 (treatment day 56) in a non-fasting state. Latest drug dose was administered about 18 hours before termination and animals did not receive drug dosing prior to termination. Animals were induced by $CO_2/O_2$ and during anesthesia (isoflurane), the abdominal cavity was opened and cardiac blood obtained for collection of terminal plasma. Upon necropsy, whole liver was collected and weighed. The left lateral lobe was divided into pieces and snap frozen in liquid nitrogen for gene expression analysis and in 4% PFA for histology and biochemical analysis. A piece of liver was snap frozen in liquid nitrogen for biochemical analysis.

Liver Tissue Processing

Terminal liver tissue: Following 8 weeks of treatment, the whole liver was collected, weighed and liver biopsies from the left lateral lobe were excised and immediately placed in 4% PFA (~150-200 mg) and snap frozen (~50 mg). A liver piece (~100 mg) was collected in FastPrep tube and snap-frozen in liquid nitrogen.

Fixation, embedment and sections for histology: Following an over-night fixation in 4% PFA, liver biopsies were infiltrated over-night in paraffin in an automated Miles Scientific Tissue-TEK VIP Tissue Processor and subsequently embedded in paraffin blocks. Biopsies from five different animals were embedded in one block. The blocks were trimmed and two 3 µm sections per block were cut on a Microm HM340E Microtome (Thermo Scientific).

Tissue homogenation for liver triglyceride and cholesterol analyses: 1 mL 5% NH-40/ddH2O solution (ab142227, Abcam) was added to the fast FastPrep tube. The tubes were placed in a FastPrep homogenizer and shaken for 2×60 seconds. After homogenization the samples were slowly heated to 80-100° C. in a heating block for 3 minutes. After being cooled to room temperature, the heating step was repeated. The samples were centrifuged for two minutes at top speed using a microcentrifuge to remove any insoluble material. The supernatant was stored at −80° C. until usage. Triglyceride and cholesterol content in liver homogenates were measured in single determinations using autoanalyzer Cobas C-111 with a commercial kit (Roche Diagnostics, Germany) according to manufacturer's instructions.

RNA purification for RNAseq: Lysis of tissue was performed using a MP FastPrep system. Briefly, 30-50 mg liver biopsy is homogenized and used for RNA extraction on NucleoSpin Plus RNA columns (Macherey-Nagel) as recommended by the supplier. The quantity of the RNA was assessed using a NanoDrop 2000 spectrophotometer (ThermoScientific).

Hepatic Steatosis Assessment

To assess hepatic steatosis, liver sections were stained with H&E followed by analysis with Visiomorph software (Visiopharm, Copenhagen, Denmark). Terminal hepatic quantitative assessment of steatosis was described as percentage of total area using a protocol designed for the specific purpose. HE staining: Paraffin embedded sections were de-paraffinated in xylene and rehydrated in series of graded ethanol. Sections were then incubated for 5 min in Mayer's Hematoxylin (Cat no. S3309, Dako), washed for 5 min in running tap water and then stained for 15 sec in Eosin Y solution (Cat. No. HT110280 2.5L, Sigma-Aldrich). Slides were hydrated, mounted with Pertex and allowed to dry before scanning.

Total NAFLD (NAS) Activity Score

The NAFLD Activity Score (NAS) provides a numerical value for patients who most likely have NASH and is the sum of the separate scores for steatosis (0-3), lobular inflammation (0-3), and hepatocellular ballooning (0-3). The majority of patients with NASH present with a NAS score of ≥5. In these experiments, the terminal liver tissue from the left lateral lobe was collected for NAS by use of clinical criteria outlined by Kleiner and colleagues (Design and validation of a histological scoring system for nonalcoholic fatty liver disease, Kleiner et al, Hepatology 41; 2005). The criteria used to determine NAS are provided in Table 1 below.

TABLE 1

| Feature | Degree | Score |
| --- | --- | --- |
| Steatosis | <5% | 0 |
|  | 5-33% | 1 |
|  | >33-66% | 2 |
|  | >66% | 3 |
| Lobular inflammation | No foci | 0 |
|  | <2 foci/200x | 1 |
|  | 2-4 foci/200x | 2 |
|  | >4 foci/200x | 3 |
| Ballooning degeneration | None | 0 |
|  | Few | 1 |
|  | Many cells/prominent ballooning | 2 |

RNA-Seq: Hepatic Terminal Gene Expression and Bioinformatic Analyses

The sequencing data were aligned to the *Mus musculus* genome obtained from the Ensembl database using the Spliced Transcripts Alignment to a Reference (STAR) software. The python script HTSeq-count available in the HTSeq package was used to count the number of reads mapping to annotated regions. All downstream analysis steps were implemented as scripts for R. For the bioinformatics analysis the quality of the data were evaluated using the standard RNA-seq quality control parameters. To evaluate the inter and intra group variability, principal component analysis and hierarchical clustering were performed. To identify differentially expressed genes the R-package edgeR was used. The list off differentially expressed genes was cross-referenced with information about established NASH biomarkers. Pathway analyses were performed to identify pathways differentially perturbed between the groups.

Example 2. Diet-Induced Obese NASH in C57BL/6j Mice: Obeticholic Acid (OCA)±Liraglutide (LIRA)

The protocols and analyses for this study are provided in Example 1.
Treatment Groups
Group 1: Vehicle (PO)+Vehicle (SQ)
  Mice (n=12) were administered vehicle from week 0 to 8.
Group 2: OCA (PO)+Vehicle (SQ)
  Mice (n=12) were administered OCA at a dose of 10 mg/kg from week 0 to 8.
Group 3: LIRA (SQ)+Vehicle (PO)
  Mice (n=12) were administered LIRA at a dose of 0.1 mg/kg from week 0 to 8.
Group 4: OCA (PO)+Vehicle (SQ)
  Mice (n=12) were administered OCA at a dose of 30 mg/kg from week 0 to 8.
Group 5: LIRA (SQ)+Vehicle (PO)
  Mice (n=12) were administered LIRA at a dose of 0.4 mg/kg from week 0 to 8.
Group 6: OCA (PO)+LIRA (SQ)
  Mice (n=12) were administered OCA at a dose of 10 mg/kg and LIRA at a dose of 0.1 mg/kg from week 0 to 8.
Group 7: OCA (PO)+LIRA (PO)
  Mice (n=12) were administered OCA at a dose of 30 mg/kg and LIRA at a dose of 0.4 mg/kg from week 0 to 8.
Group 8: Lean Chow control group
  Mice (n=9) were feed lean chow from week 0 to 8.
Compounds and Dosing All mice received PO (OCA) or SQ (LIRA) dosing once daily. Day 0 was the first day of dosing while day 55 was the last day. Hence, mice were dosed once daily from day 0 up to and including day 55. The mice received 112 doses in total of either the therapeutic agent or vehicle alone. Animals were treated between 2:00-4:00 PM. OCA was dissolved in final stock concentrations of 1 mg/ml and 3 mg/ml for final dose concentrations of 10 mg/kg and 30 mg/kg, respectively. The vehicle used for OCA was 0.5% carboxymethyl-cellulose sodium (CMC).
Results and Discussion
NAS Scores The diagnosis of nonalcoholic steatohepatitis (NASH) is established by the presence of a characteristic pattern of steatosis, inflammation, and hepatocellular ballooning on liver biopsies. The NAFLD Activity Score (NAS) provides a numerical value for patients who most likely have NASH with the majority of patients with NASH having a NAS value of ≥5. The effects of OCA (10 and 30 mg/kg, PO) and LIRA (0.1 and 0.4 mg/kg, SQ) were evaluated, alone and in combination, on the total and individual component NAS values in the DIO-NASH mice. As used in example 1A, a low dose combination refers to OCA (10 mg/kg)/LIRA (0.1 mg/kg) while the high dose refers to OCA (30 mg/kg)/LIRA (0.4 mg/kg).

Figure 1B:
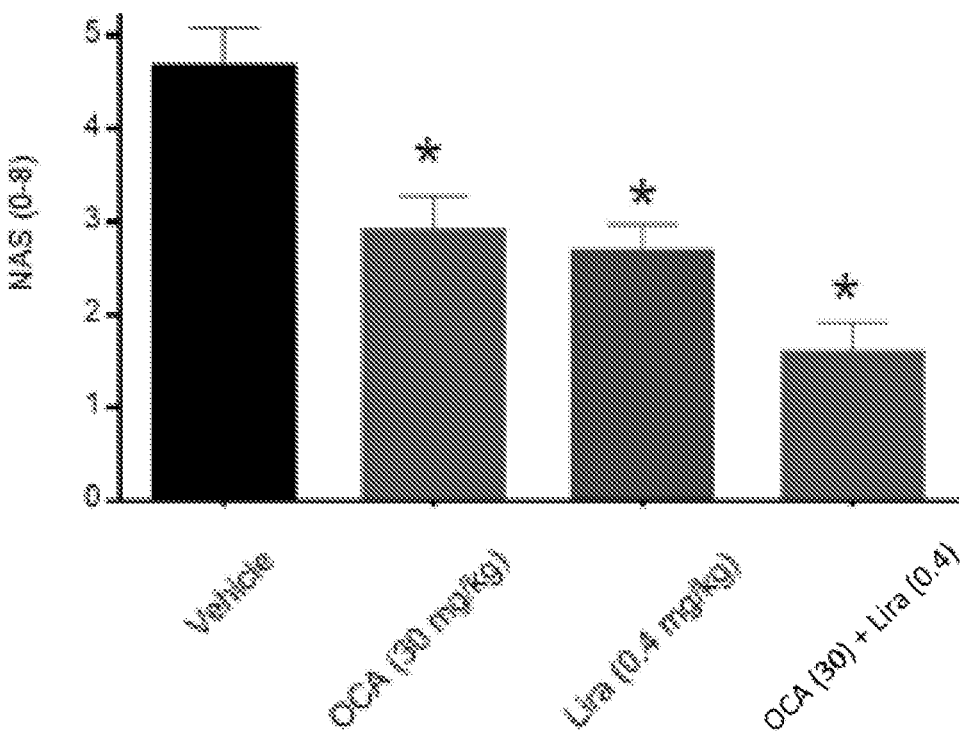
FIG. 1B is a bar graph showing the effect of a high dose of OCA and LIRA, alone and in combination, on total NAS. *$p<0.05$ vs. control.
Figure 2A:
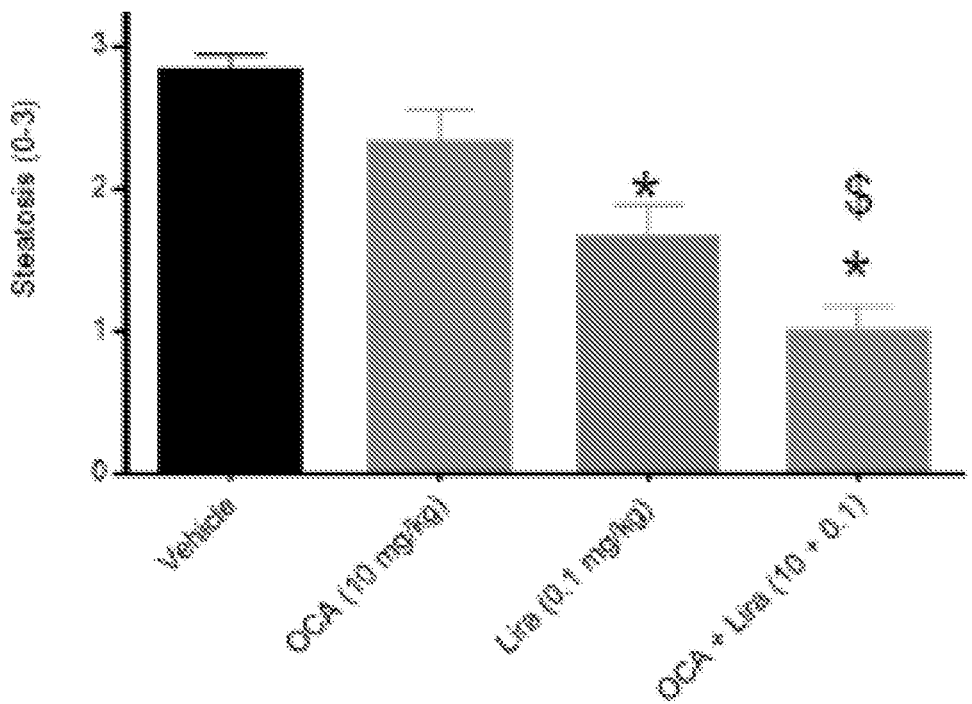
FIG. 2A is a bar graph showing the effect of a low dose of OCA and LIRA, alone and in combination, on the steatosis component of NAS. *$p<0.05$ vs. control and $^\$p<0.05$ vs. OCA.
Figure 2B:
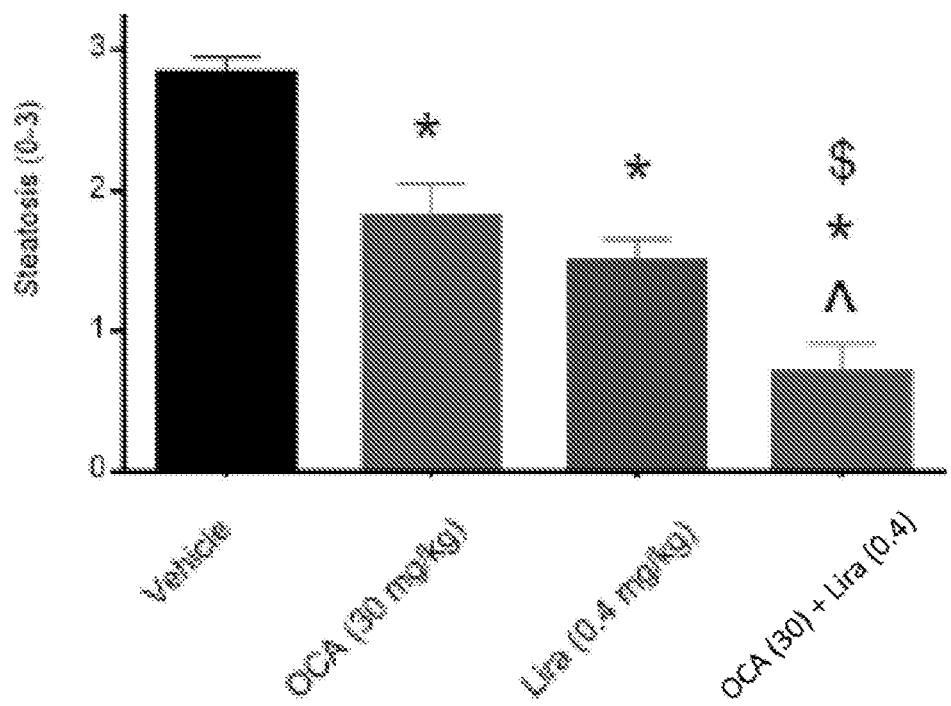
FIG. 2B is a bar graph showing the effect of a high dose of OCA and LIRA, alone and in combination, on the steatosis component of NAS. *$p<0.05$ vs. control, $^\$p<0.05$ vs. OCA, and $^\wedge p<0.05$ vs. LIRA.
Figure 3A:
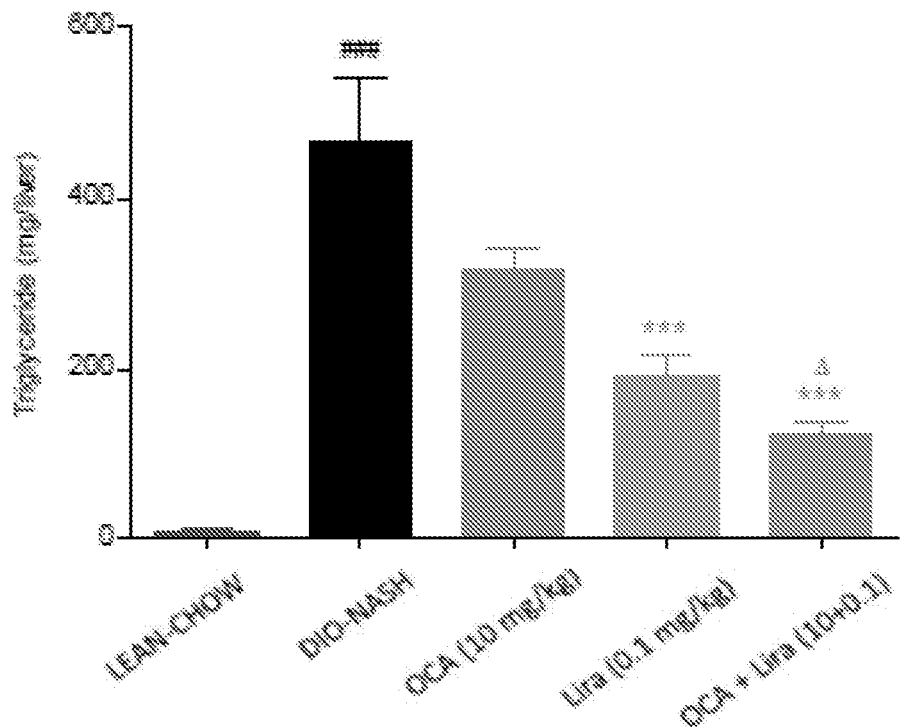
FIG. 3A is a bar graph showing the effect of a low dose of OCA and LIRA, alone and in combination, on total liver triglyceride content. $^{\#\#\#\#}p<0.001$ vs. LEAN-CHOW vehicle, *$p<0.001$ vs. DIO-NASH vehicle; and $^\Delta p<0.05$ vs. DIO-NASH OCA (10 mg/kg).
Figure 3B:
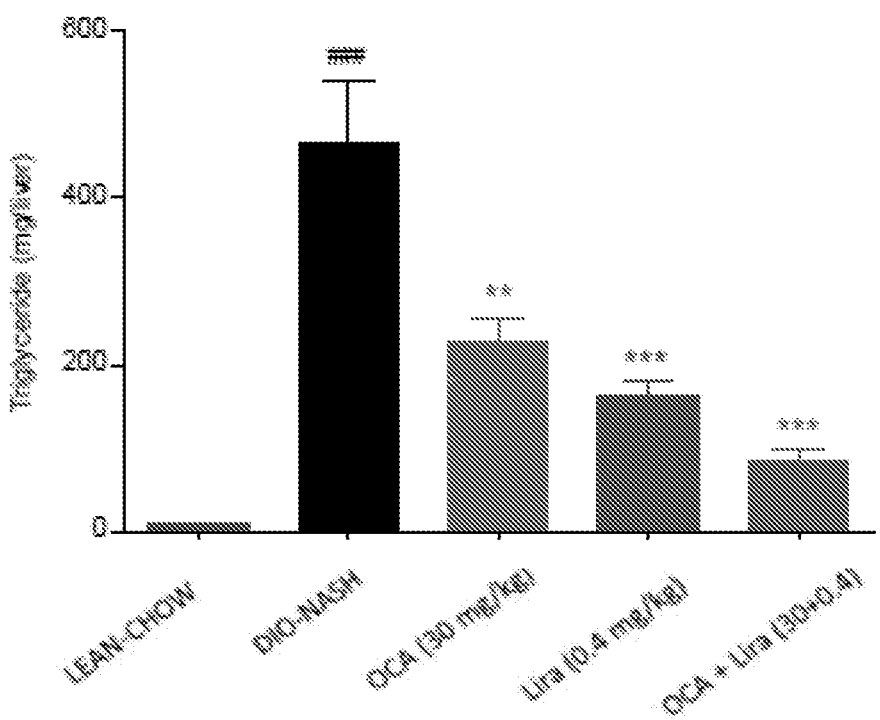
FIG. 3B is a bar graph showing the effect of a high dose of OCA and LIRA, alone and in combination, on total liver triglyceride content. $^{\#\#\#\#}P<0.001$ vs. LEAN-CHOW vehicle, $p<0.05$ and ***$p<0.001$ vs. DIO-NASH vehicle.
Figure 4A:
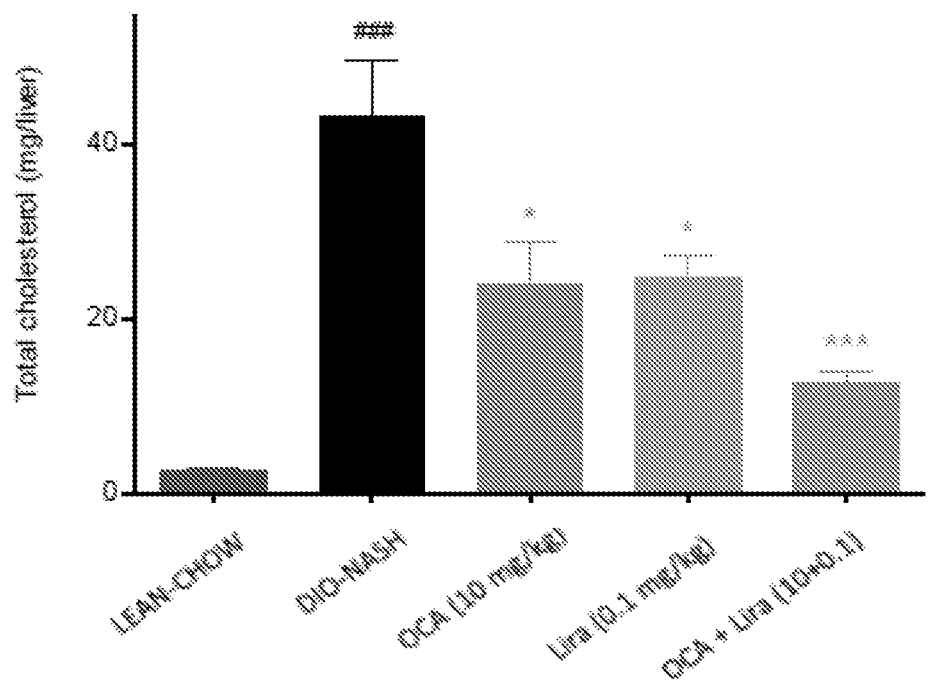
FIG. 4A is a bar graph showing the effect of a low dose of OCA and LIRA, alone and in combination, on total liver cholesterol content. $^{\#\#\#\#}p<0.001$ vs. LEAN-CHOW vehicle; *$p<0.05$ and *$p<0.001$ vs. DIO-NASH vehicle.
Figure 4B:
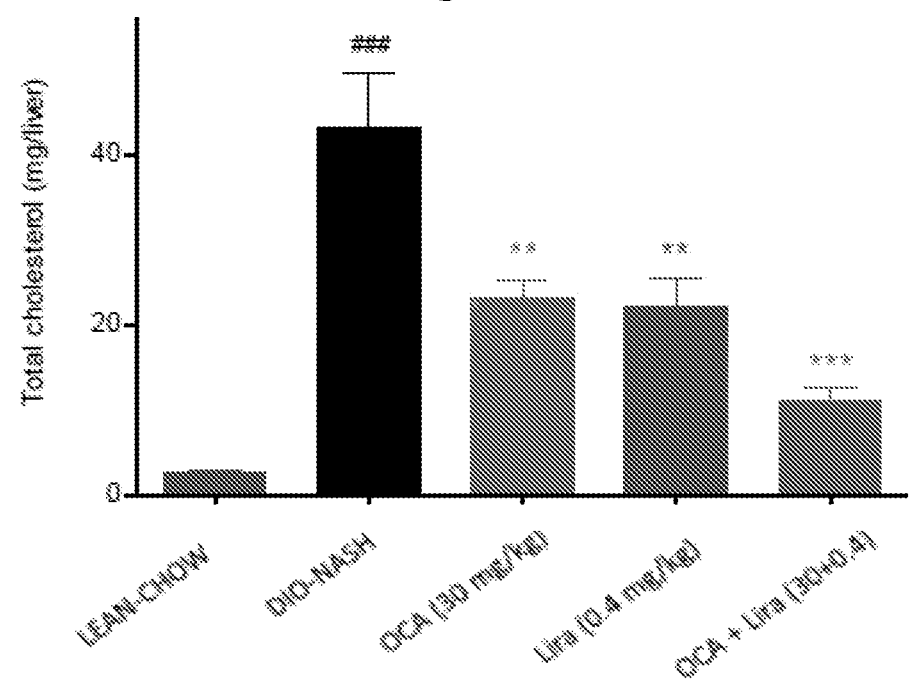
FIG. 4B is a bar graph showing the effect of a high dose of OCA and LIRA, alone and in combination, on total liver cholesterol content. $^{\#\#\#\#}p<0.001$ vs. LEAN-CHOW vehicle; $p<0.01$ and ***$p<0.001$ vs. DIO-NASH vehicle.
Figure 5:
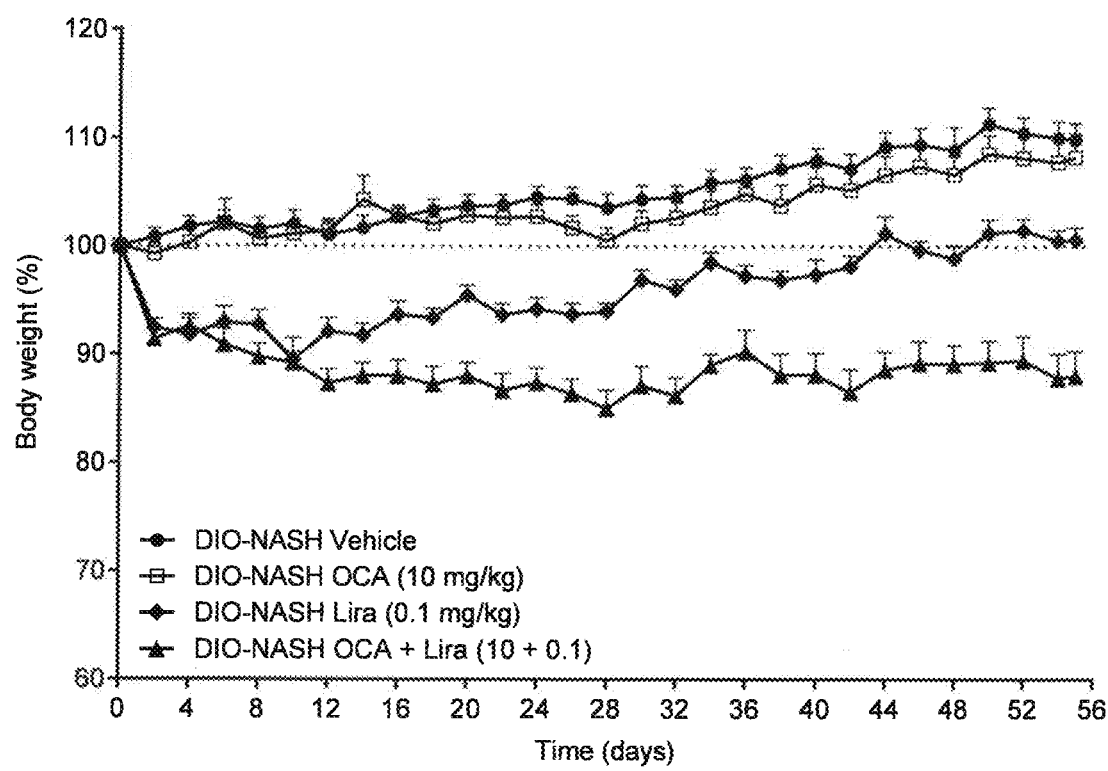
FIG. 5 is a graph showing the effect of a low dose of OCA and LIRA, alone and in combination, on body weight during the study period.
Figure 6A:
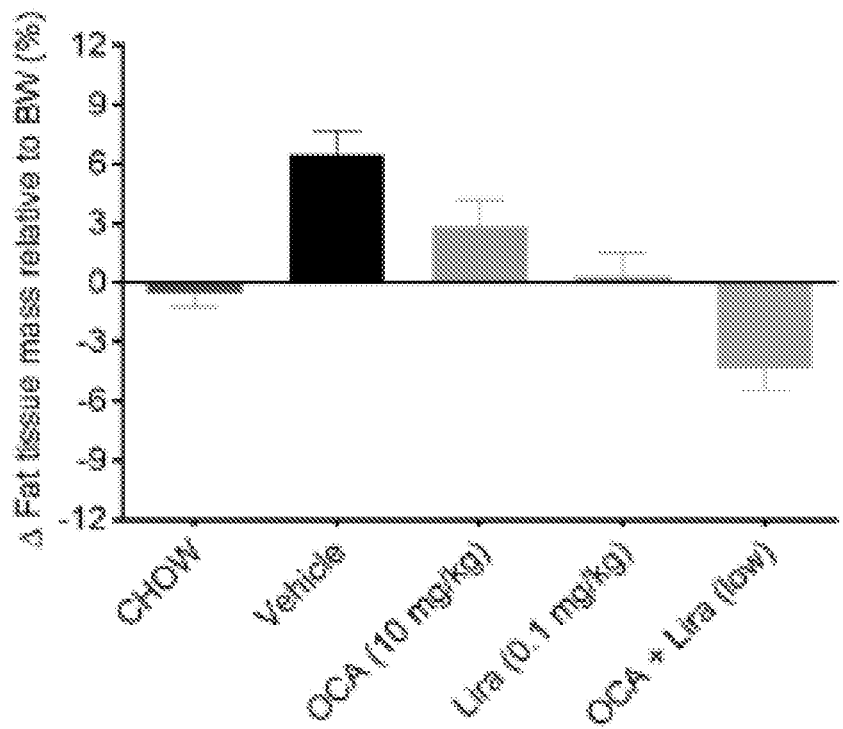
FIG. 6A is a bar graph showing the effect of a low dose of OCA and LIRA, alone and in combination, on change in fat tissue mass relative to body weight.
Figure 6B:
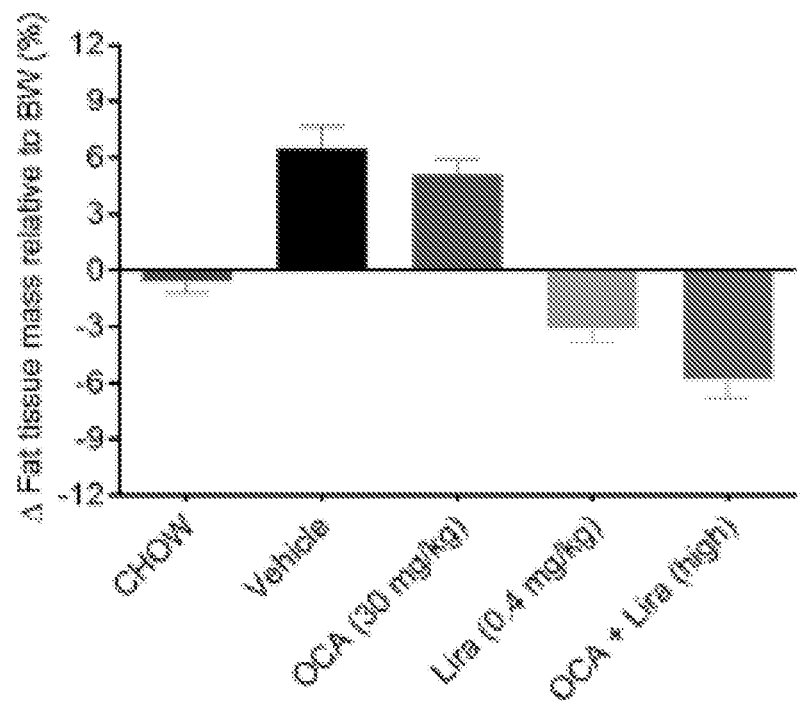
FIG. 6B is a bar graph showing the effect of a high dose of OCA and LIRA, alone and in combination, on the change in the tissue mass relative to body weight.
Figure 7A:
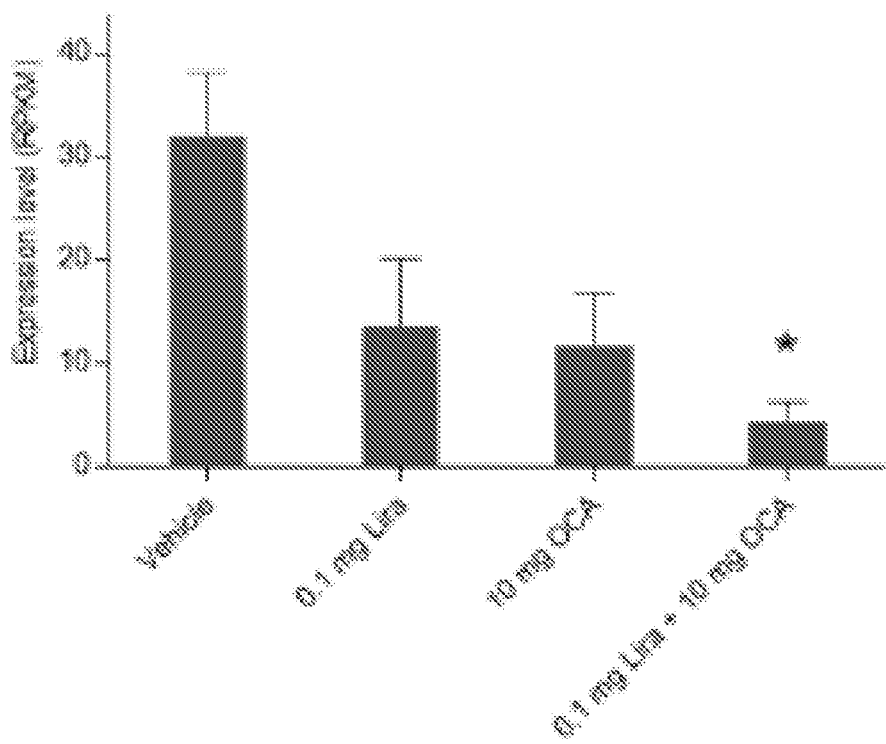
FIGS. 7A-7E describe the effect on genes uniquely regulated by a low dose OCA and LIRA, alone and in combination. *$p<0.005$ vs. vehicle control.
Figure 7B:
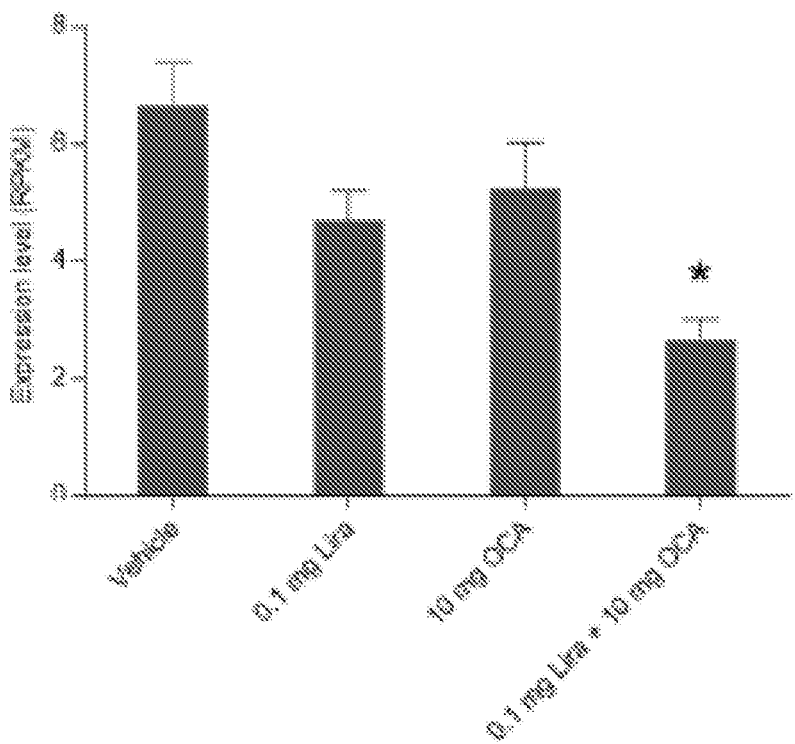
Figure 7C:
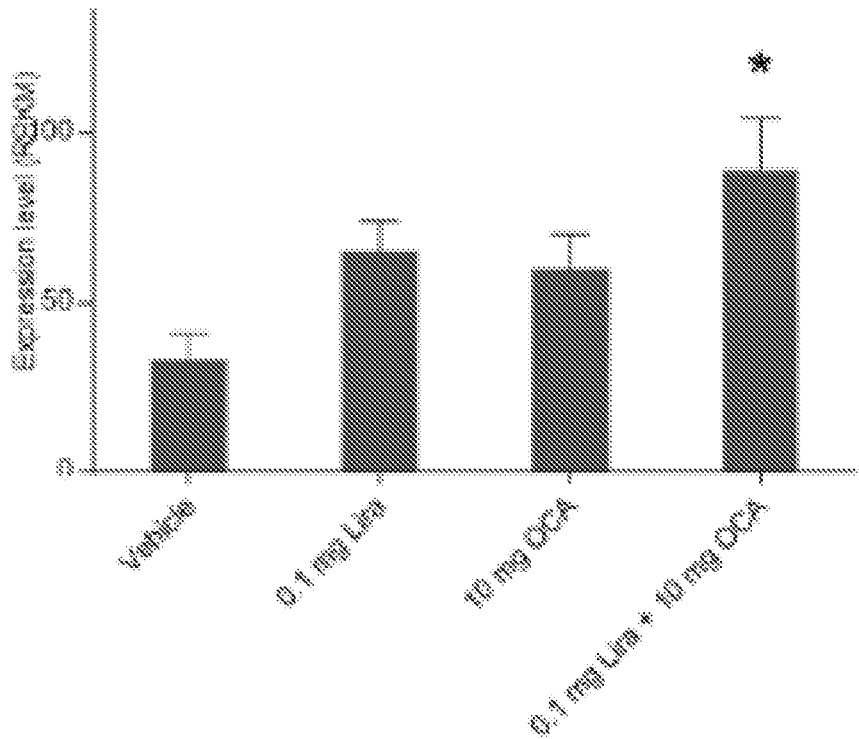
Figure 7D:
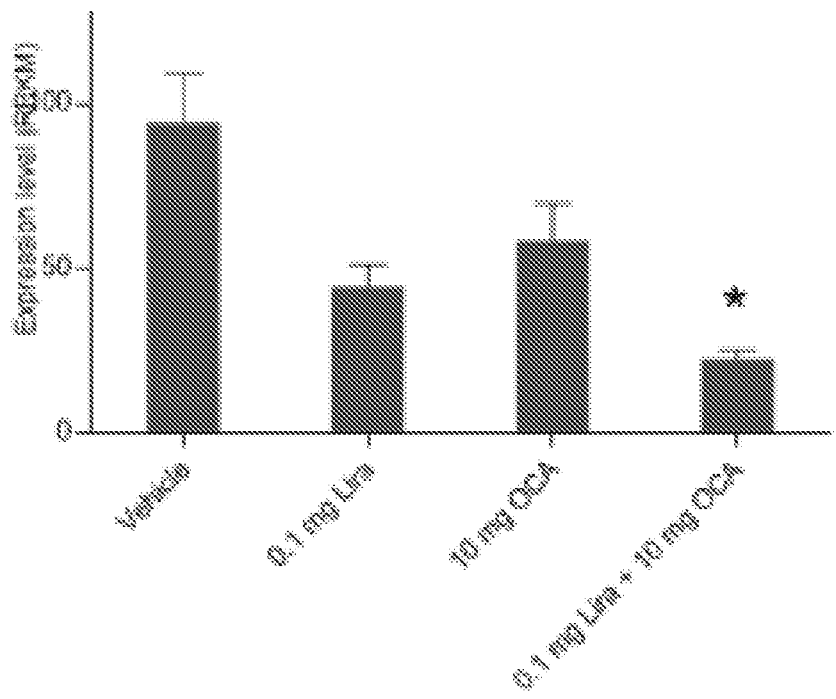
Figure 7E:
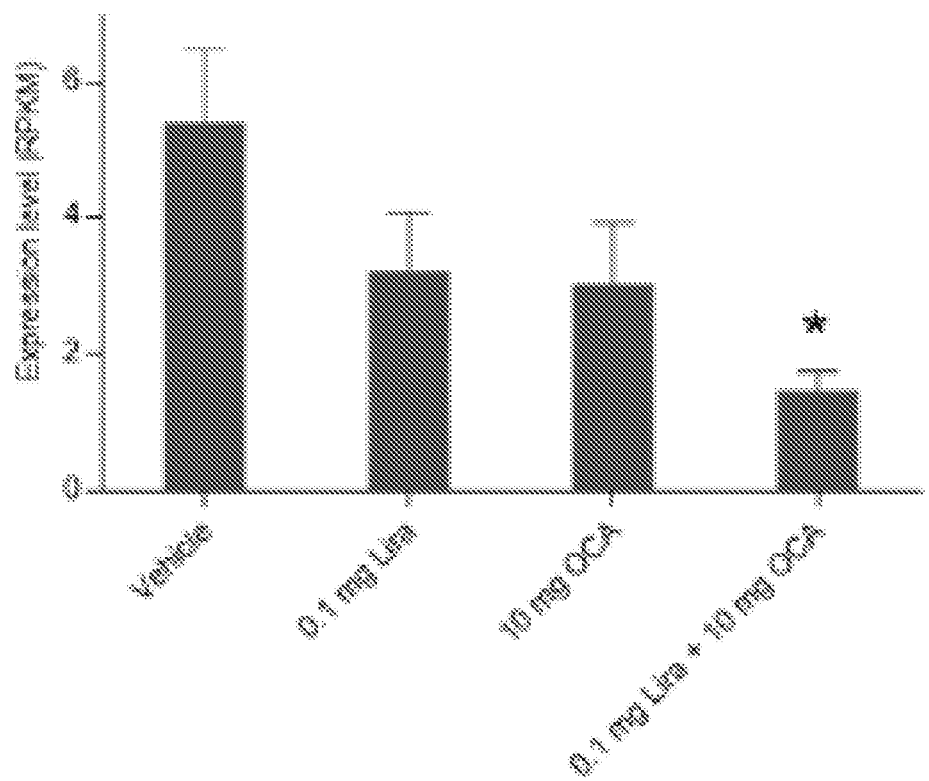
Figure 8B:
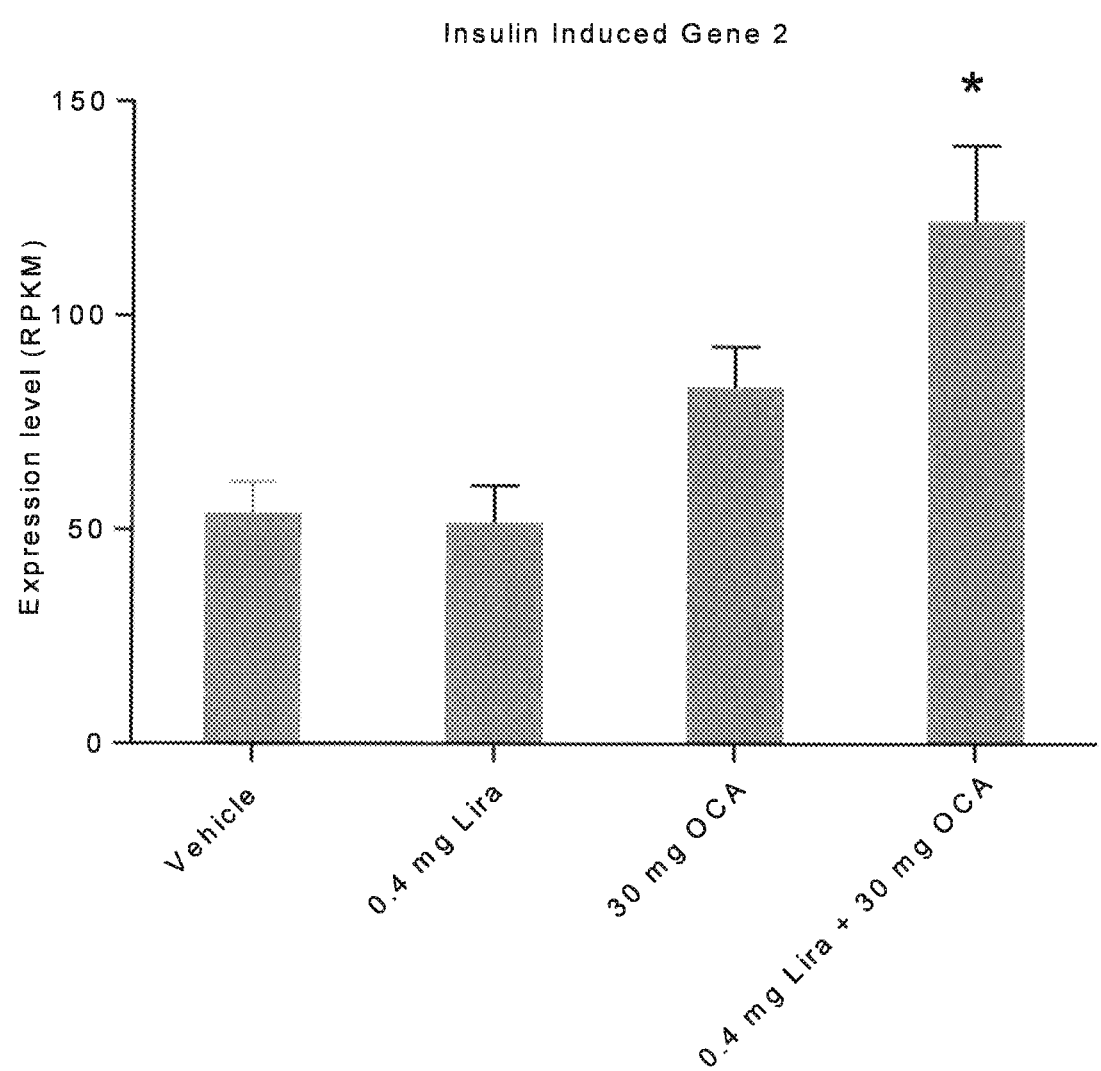
Figure 8D:
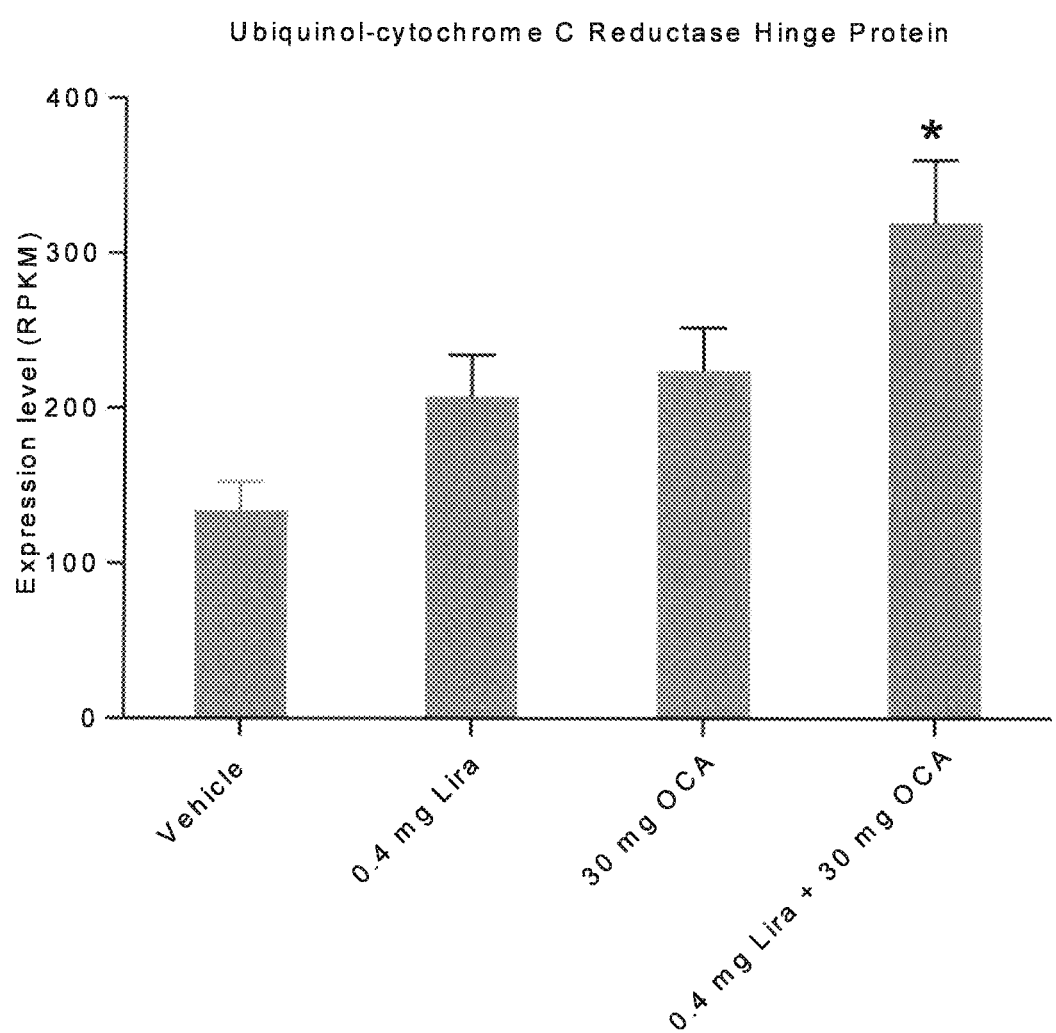

FIGS. 1A and 1B depict the reduction of NAS scores of low and high dose combinations of OCA and LIRA after eight weeks of treatment, respectively. The data indicate that both low and high dose combinations reduce total NAS relative to control. In particular, the effect of low dose combination of OCA and LIRA was statistically significant against the vehicle groups as well as the low dose of OCA alone. The largest improvement in NAS was about three points. The improvement by the high dose combination lowered the NAS value from 4.6 to 1.6 ($p<0.05$ vs. OCA monotherapy). Approximately two of the points were due to reducing the steatosis component. The effect of low and high doses of the combination of OCA and LIRA on the steatosis component are displayed in FIGS. 2A and 2B, respectively. Both dose combinations improved steatosis in a statistically significant manner ($p<0.05$ vs. OCA or LIRA monotherapy).
Liver Triglycerides and Cholesterol As fatty liver is characterized by an accumulation of lipids including triglycerides and cholesterol, the effect of the low and high dose combinations of OCA and LRA were examined. After eight weeks of treatment, the combination reduced liver triglycerides in a significantly statistically manner as shown in FIGS. 3A and 3B. Both dose combinations reduced the levels of liver triglycerides and cholesterol while the low dose combination gave a synergistic effect. With respect to cholesterol, the high dose combination reduced the level of cholesterol in the liver in a significantly statistically manner as shown in FIGS. 4A and 4B.
Body Weight and Composition LIRA is indicated in the U.S. as an adjunct to lifestyle for chronic weight management in obese individuals. However, a REMS (Risk Evaluation and Mitigation Strategy) was required by the FDA due to potential risks associated with LIRA include medullary thyroid carcinoma and the risk of acute pancreatitis, including necrotizing pancreatitis. Thus, using a lower dose of LIRA while maintaining its maximum weight loss effect is highly desired. The effect of the low dose combination on body weight are provided in FIG. 5. As shown in FIG. 5, the low dose combination of OCA and LIRA synergistically decreased body weight by about 13% relative to monotherapy alone. With respect to body composition, FIGS. 6A and 6B reveal that the low and high dose combinations reduced adiposity (or fat tissue mass) relative to body weight. In particular, the high dose combination of OCA and LIRA synergistic reduced adiposity in mice.
Transcriptomics Analysis RNA sequencing was performed on liver mRNA samples from the study mice to gain insight into the underlying mechanisms and pathways on the improvement of the total NAS by the combination therapies. The following genes were examined: cell death-inducing DFFA-like effector C; death effector domain-containing DNA binding protein 2; 2-hydroxyacyl-CoA lyase 1, lectin glactose binding; oxysterol binding protein-like 3; estrogen receptor; insulin induced gene, lipin1; and ubiquinol-cytochrome C reductase hinge protein. The genes differentially regulated between the low and high dose combinations, control, and each respective monotherapy were compared. The effect of maintaining mice on a high-fat diet from the study illustrates these processes in which significantly upregulated and down-regulated genes were changed as a function of mono- or combination-therapy treatment. Quantitative values of the expression levels affected by the low dose combination relative to the monotherapy are provided in FIGS. 7A-7E. Table 2 describes the predicted function and the qualitative regulation of genes involved in the development of fibrosis. The combination regulated gene expression in a statistically significant manner relative to the vehicle group.

TABLE 2

| Gene | Full Name/s | Predicted Function | Combination vs. low dose LIRA Monotherapy | Combination vs. low dose OCA Monotherapy |
|---|---|---|---|---|
| CIDEC | Cell Death-Inducing DFFA-Like Effector C | Upregulated in NASH, promotes lipid droplets in adipocytes | ↓ | ↓ |
| Dedd2 | Death effector domain-containing DNA binding protein 2 | Receptor for chemotactic activity for lymphocytes | ↓ | ↓ |
| Hacl1 | 2-Hydroxyacyl-CoA lyase 1 | Peroxisomal biology, breaks down long chain 2-hydroxyfatty acids | ↑ | ↑ |
| Lgls1 | Lectin glactose binding | Modulates cell-cell, cell-matrix adhesion | ↓ | ↓ |
| osbpl3 | Oxysterol binding protein-like 3 | Regulates cell adhesion and organization | ↓ | ↓ |

The comparison of the levels of expression affected by the high dose combination are provided in FIGS. 8A-8D. Table 3 describes the predicted role or function of each gene in the development of NASH.

TABLE 3

| Gene | Full Name/s | Predicted Role or Function | Combination vs. Liraglutide Monotherapy | Combination vs. OCA Monotherapy |
|---|---|---|---|---|
| ER | Estrogen Receptor | Estrogen is protective against fibrosis | ↑ | ↑ |
| INSIG1 | Insulin induced gene | Decrease leads to increased CHOL synthesis. Down-regulation is consistent with the decreases in hepatic CHOL and ultimately NASH progression | ↑ | ↑ |
| LPIN1 | Lipin1 | Coordinates hepatic mitochondrial and glycerolipid metabolism | ↓ | ↓ |
| UQCRH | Ubiquinol-cytochrome C Reductase Hinge Protein | Interactions with SIRT1 and SIRT3 - increases in SIRT consistent with improved metabolic status. | ↑ | ↑ |

Example 3. Diet-Induced Obese NASH in C57BL/6j Mice: Obeticholic Acid (OCA)±Metformin (MET)

The protocols and analyses for this study are provided in Example 1.
Treatment Groups
Group 1: Vehicle (PO)
  Mice (n=11) were administered vehicle (0.5% CMC) from week 0 to 8.
Group 2: OCA (PO)+Vehicle (PO)
  Mice (n=11) were administered OCA at a dose of 10 mg/kg from week 0 to 8.
Group 3: MET (PO)+Vehicle (PO)
  Mice (n=12) were administered MET at a dose of 50 mg/kg from week 0 to 8.
Group 4: OCA (PO)+Vehicle (PO)
  Mice (n=11) were administered OCA at a dose of 30 mg/kg from week 0 to 8.
Group 5: MET (PO)+Vehicle (PO)
  Mice (n=12) were administered MET at a dose of 150 mg/kg from week 0 to 8.
Group 6: OCA (PO)+MET (PO)
  Mice (n=12) were administered OCA at a dose of 10 mg/kg and MET at a dose of 50 mg/kg from week 0 to 8.
Group 7: OCA (PO)+MET (PO)
  Mice (n=10) were administered OCA at a dose of 30 mg/kg and MET at a dose of 150 mg/kg from week 0 to 8.
Group 8: Lean Chow control group
  Mice (n=10) were feed lean chow from week 0 to 8.
Compounds and Dosing
  All mice received PO dosing once daily. Day 0 was the first day of dosing while day 55 was the last day. Hence, mice were dosed once daily from day 0 up to and including day 55. The mice received 56 doses in total. Animals were subjected to treatment between 2:00-4:00 PM. OCA was dissolved in final stock concentrations of 1 mg/ml and 3 mg/ml for final dose concentrations of 10 mg/kg and 30 mg/kg, respectively. The dosing volume was 10 mL/kg. MET was prepared in final stock concentrations of 5 mg/ml and 15 mg/ml for final dose concentrations of 50 mg/kg and 150 mg/kg, respectively. The dosing volume was 10 mL/kg. Vehicle used for OCA and MET was 0.5% carboxymethyl-cellulose sodium (CMC).

Results

NAS Scores

The diagnosis of nonalcoholic steatohepatitis (NASH) is established by the presence of a characteristic pattern of steatosis, inflammation, and hepatocellular ballooning on liver biopsies. The NAFLD Activity Score (NAS) provides a numerical value for patients who most likely have NASH with the majority of patients with NASH having a NAS score of ≥5. The effects of OCA (10 and 30 mg/kg, PO) and MET (50 and 150 mg/kg, PO), alone and in combination, were on the total and individual component NAS in the DIO-NASH mice were examined. As in example 1B, a low dose combination refers to OCA (10 mg/kg)/MET (50 mg/kg) while the high dose combination refers to OCA (30 mg/kg)/MET (150 mg/kg).

Figure 9A:
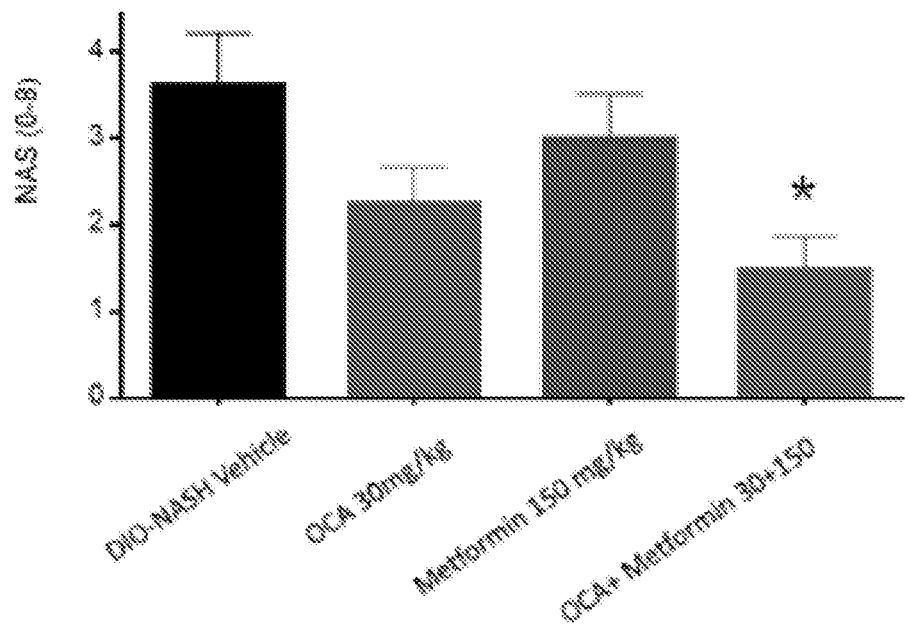
FIG. 9A is a bar graph showing the effect of a high dose of OCA and metformin (MET), alone and in combination, on total NAS. *$p<0.005$ vs. vehicle control.
Figure 9B:
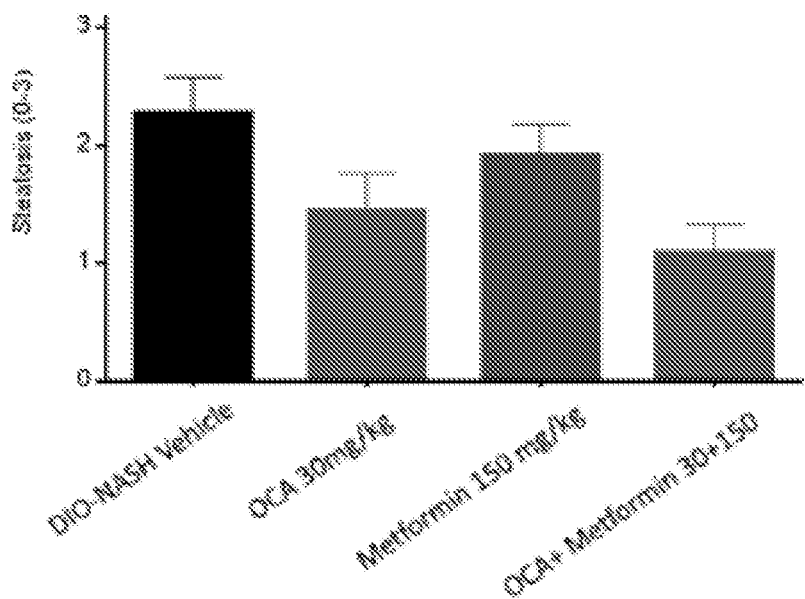
FIG. 9B is a bar graph showing the effect of a high dose of OCA and MET, alone and in combination, on the steatosis component of NAS.

FIG. 9A depicts the effect of the high dose of combination of OCA and MET on total NAS. The high dose combination of OCA and MET reduced NAS (p<0.05 vs. OCA control) in a statistically significant manner at the study end. With respect to individual components, the effect of high dose of the combination of OCA and MET on the steatosis component is displayed in FIG. 9B.

Blood Glucose Levels

Figure 10A:
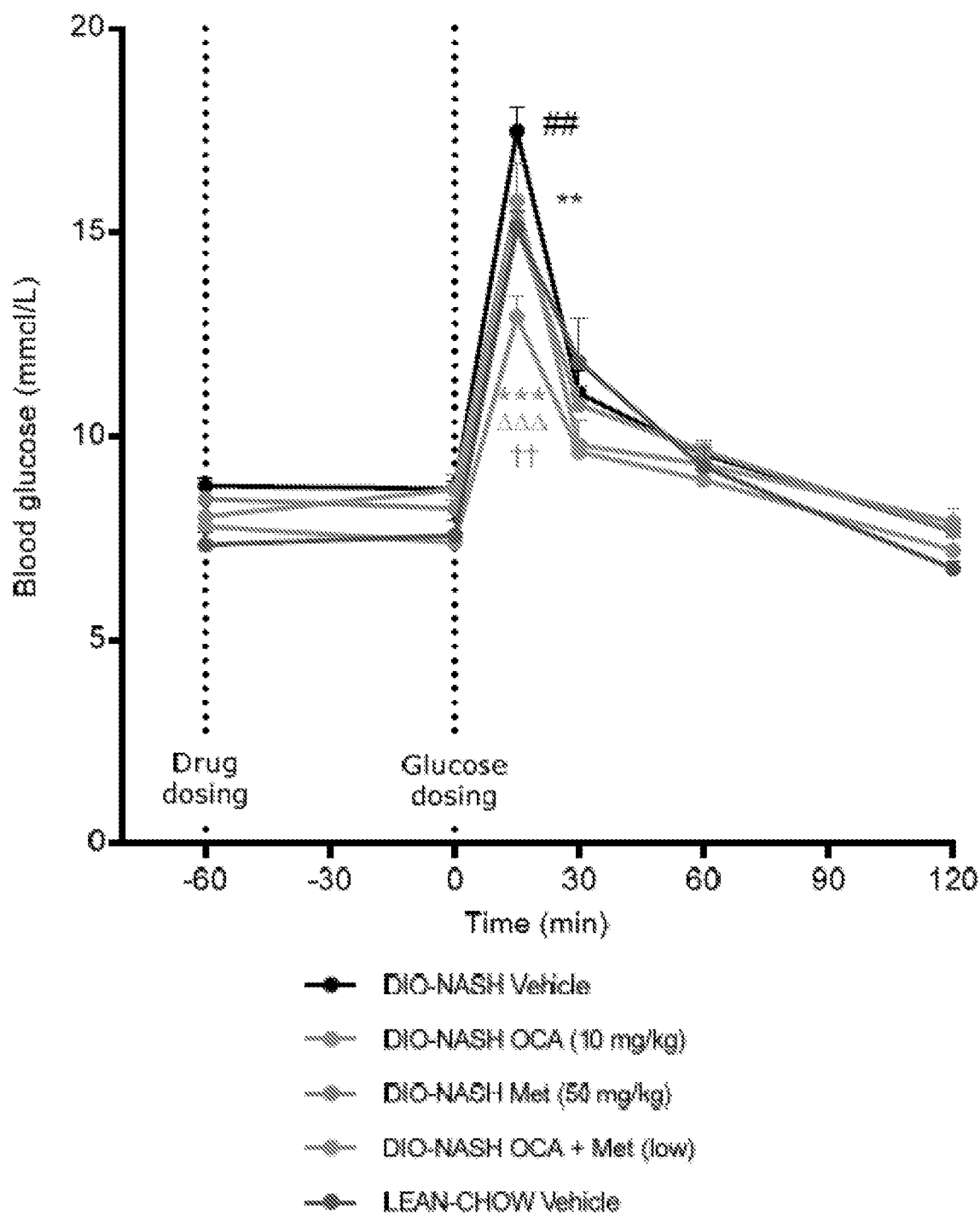
FIG. 10A is a graph showing the effect of a low dose of OCA and MET, alone and in combination, on reducing blood glucose using OGTT at week 4. $^{\#\#}p<0.001$ vs. LEAN-CHOW vehicle, $p<0.01$ and *$p<0.001$ vs. DIO-NASH vehicle, $^{\Delta\Delta\Delta}p<0.05$ vs. DIO-NASH OCA (10 mg/kg), and $^{\dagger\dagger}p<0.05$ vs. DIO-NASH MET (50 mg/kg).
Figure 10B:
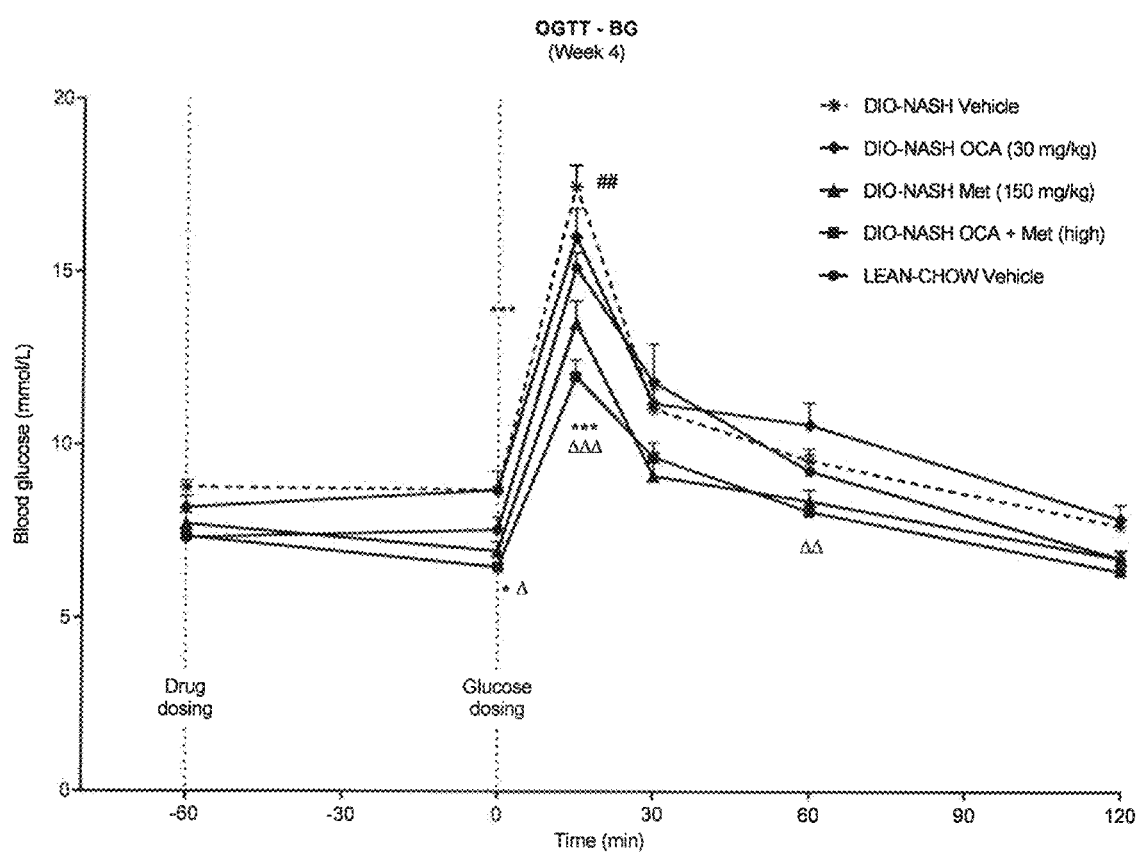
FIG. 10B is a graph showing the effect of a low dose of OCA and MET, alone and in combination, on reducing blood glucose using OGTT at week 4. ###p<0.001 vs. LEAN-CHOW vehicle, *p<0.05, ***p<0.001 vs. DIO-NASH vehicle; and Δp<0.005, ΔΔp<0.0, 1 ΔΔΔp<0.001 vs. DIO-NASH OCA (30 mg/kg).
Figure 12A:
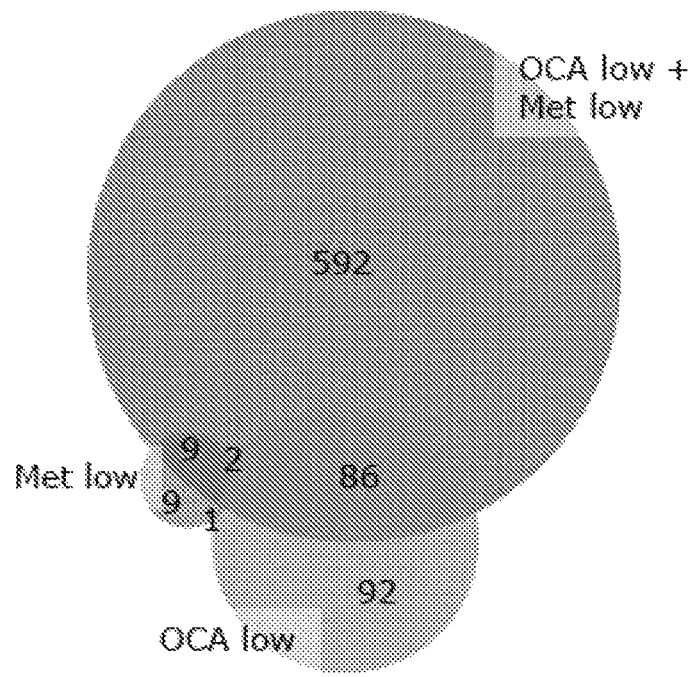
FIG. 12A is a venn diagram showing the effect of a low dose of OCA and metformin, alone and in combination, on gene expression.
Figure 12B:
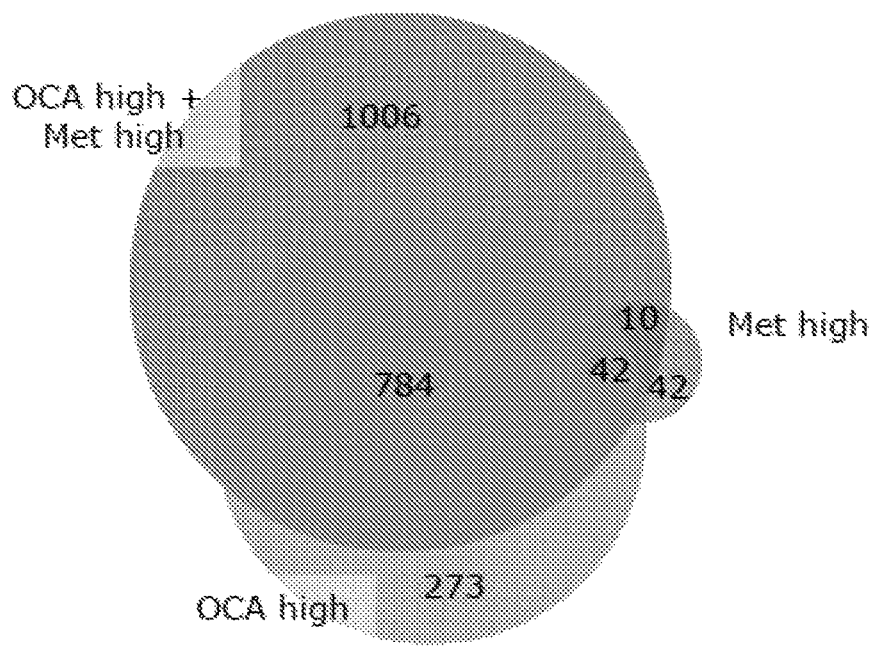
FIG. 12B is a venn diagram showing the effect of a high dose of OCA and MET, alone and in combination, on gene expression.
Figure 12C:
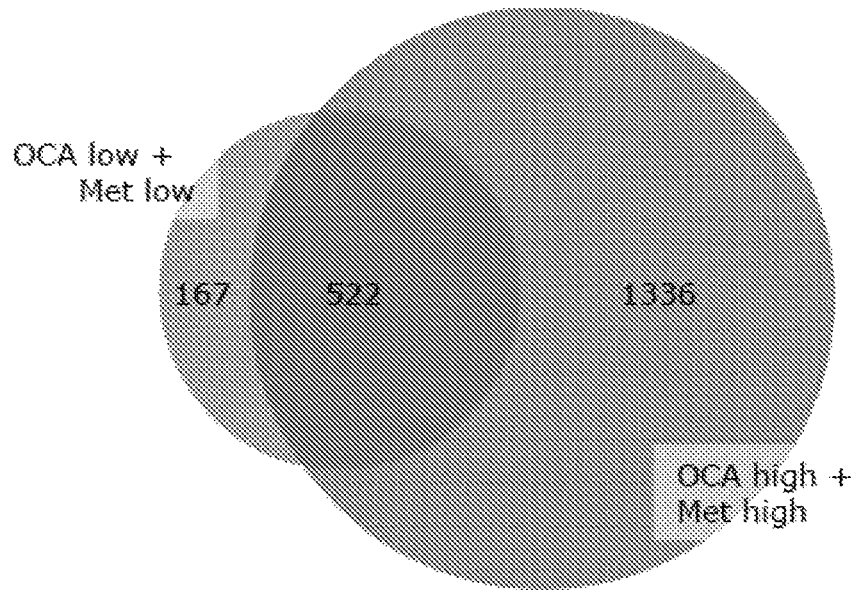
FIG. 12C is a venn diagram comparing the number of genes regulated by low and high doses of OCA and MET.

The oral glucose tolerance test (OGTT) is a medical test in which glucose is orally administered and blood samples taken afterwards to determine the time that glucose is cleared from the blood. The assay is performed to test for diabetes, insulin resistance, and impaired beta cell function. At week four of the study, a dose of glucose was orally administered and blood levels were analyzed four hours later. FIGS. 10A and 10B show that the low and high dose combinations of OCA and MET decreased blood glucose at week 4 of treatment compared to DIO-NASH Vehicle group. Table 4 provides the blood glucose levels (AUC) of the low and high dose combinations as measured in the OGTT.

treatments did not alter genes relative to the vehicle group, a number of genes were uniquely regulated in the combination relative to the vehicle group consistent with synergistic effects to improve NASH. The Venn diagrams of FIGS. 12A-12C provide a facile comparison of number of regulated genes. The results demonstrate that unique fibrosis related genes were regulated in the combination relative to the monotherapy groups consistent with synergistic effects to improve NASH.

TABLE 5

| | Treatment Group | | | | |
|---|---|---|---|---|---|
| | Group 2 | Group 3 | Group 4 | Group 5 | Group 6 | Group 7 |
| Number of Regulated Genes | 21 | 181 | 689 | 120 | 1109 | 1858 |

Figure 13A:
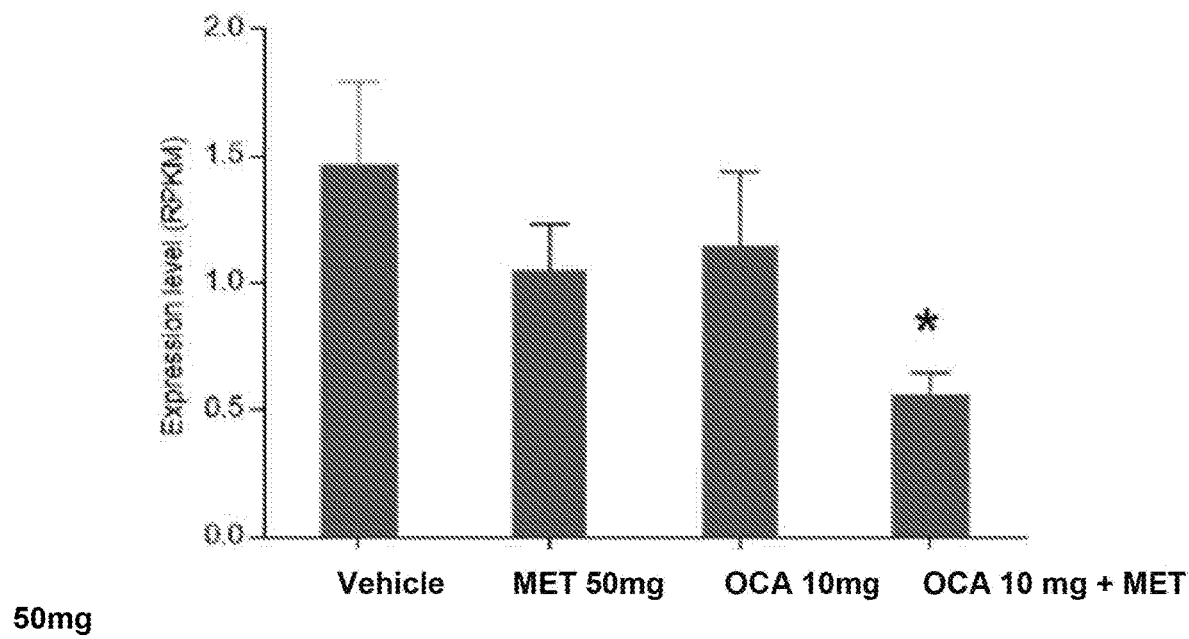
FIG. 13A is a bar graph showing the effect of low dose of OCA and MET, alone and in combination, on mRNA expression of collagen type 6a2.
Figure 13B:
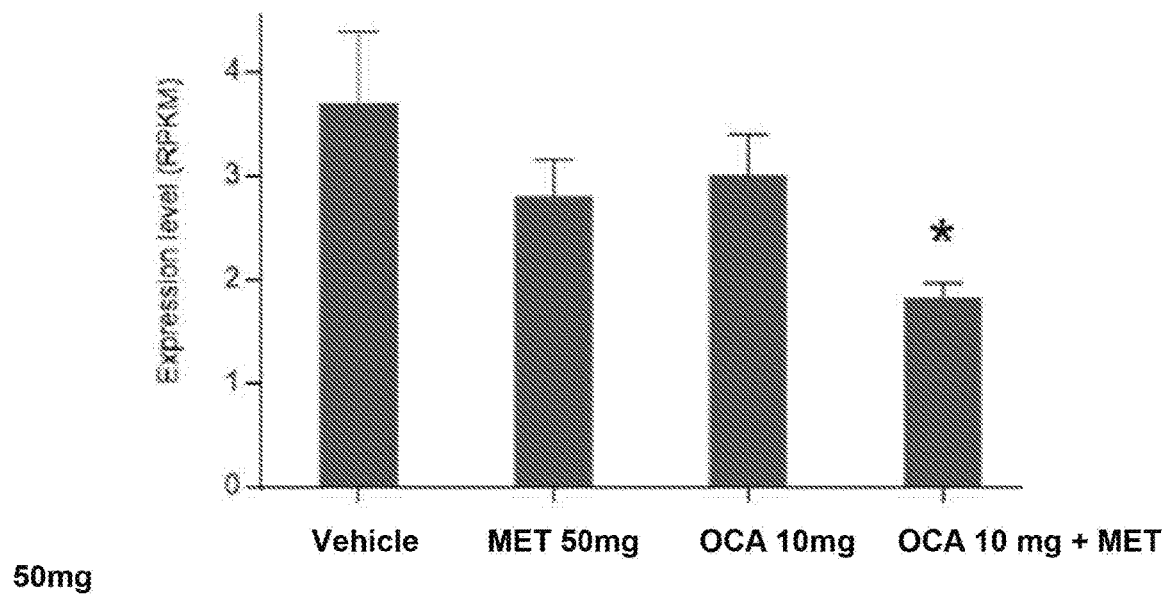
FIG. 13B is a bar graph showing the effect of low dose of OCA and MET, alone and in combination, on mRNA expression of collagen type 4a2.
Figure 13C:
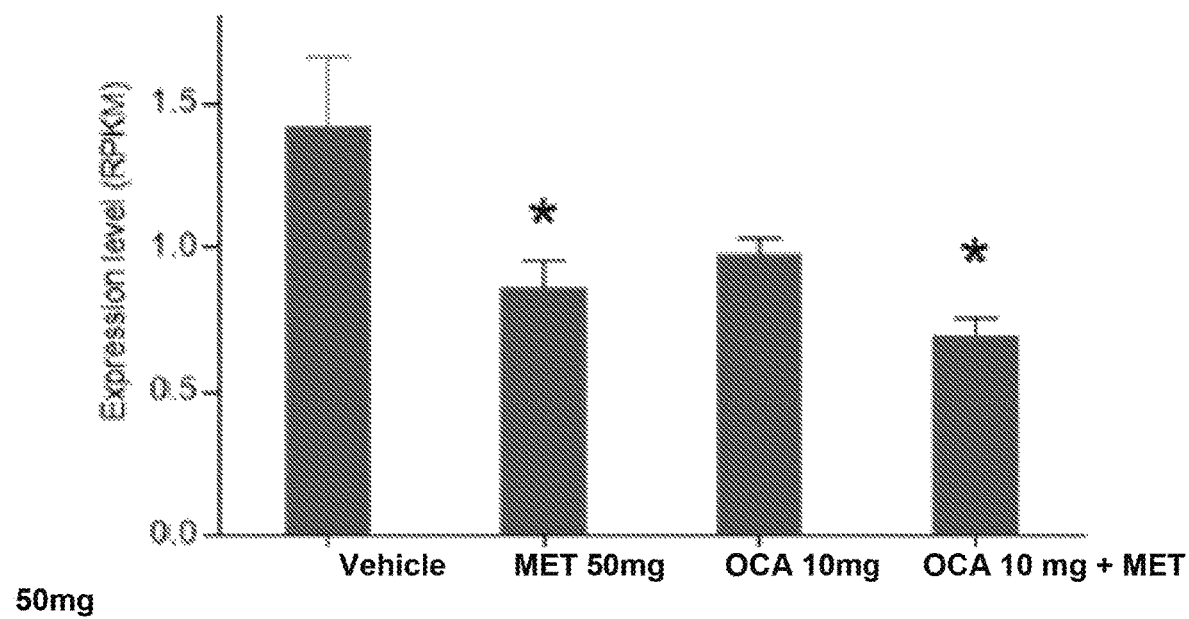
FIG. 13C is a bar graph showing the effect of low dose of OCA and MET, alone and in combination, on mRNA expression of collagen type 5a1.
Figure 14A:
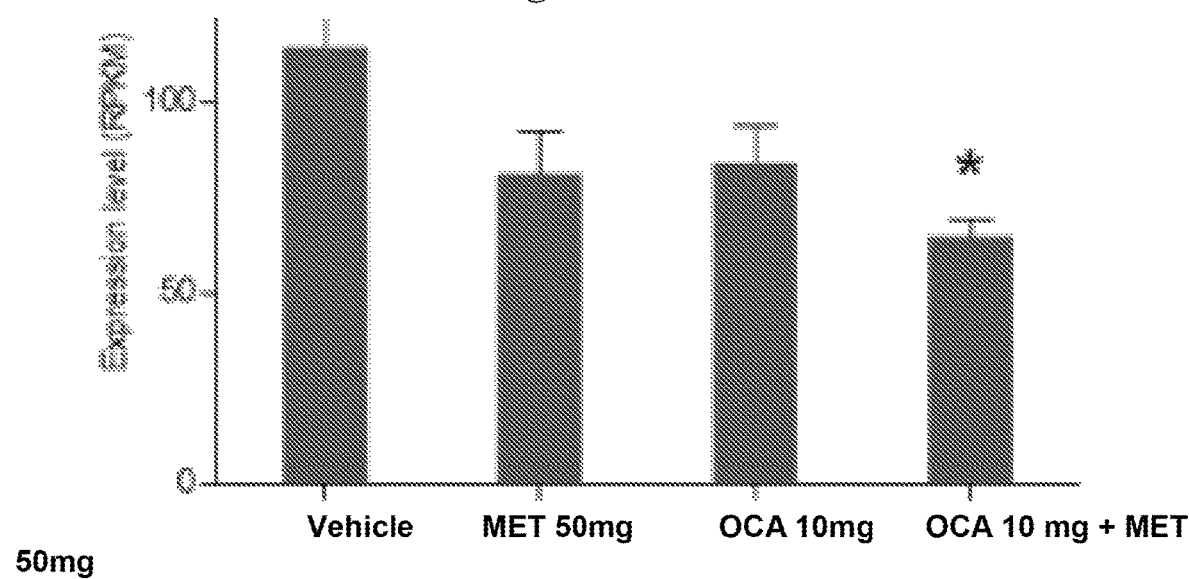
FIGS. 14A-14F describe the effect on the expression level of certain genes uniquely regulated by a low dose OCA and MET, alone and in combination. *p<0.005 vs. vehicle control.
Figure 14B:
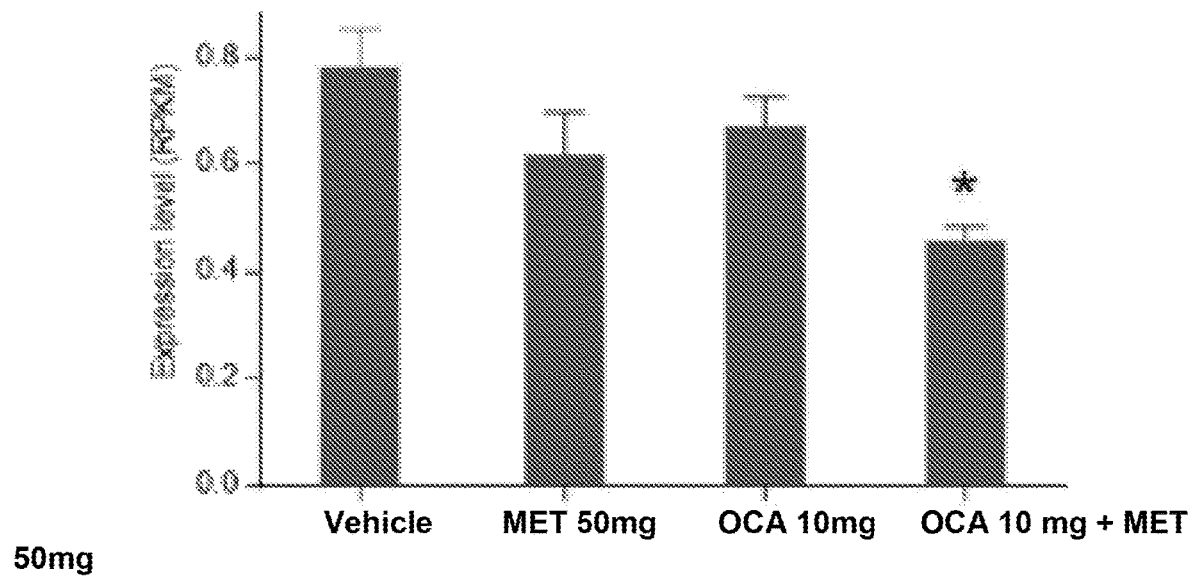
Figure 14C:
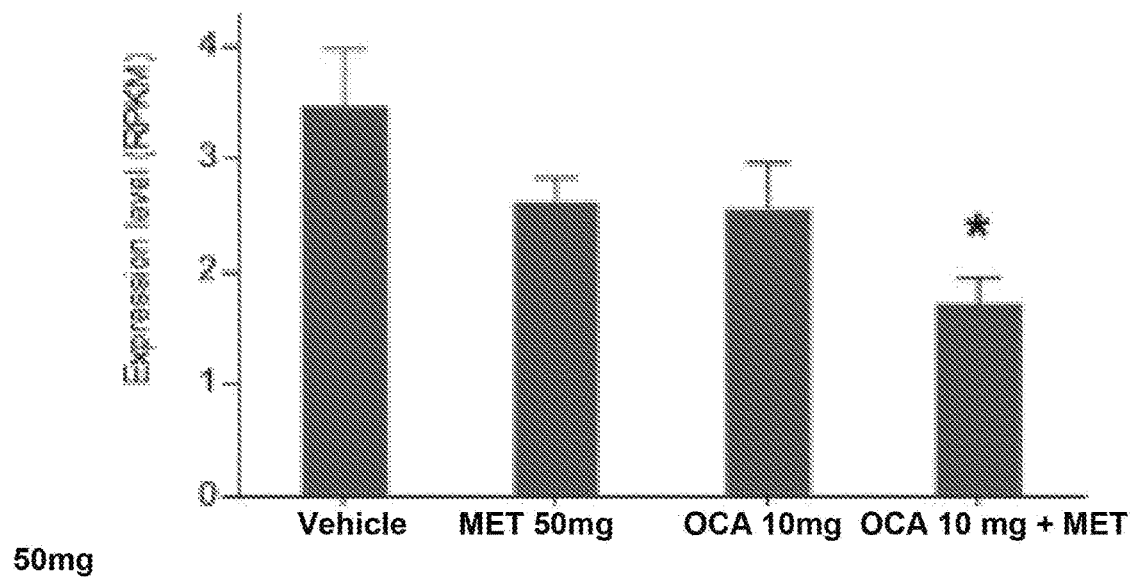
Figure 14D:
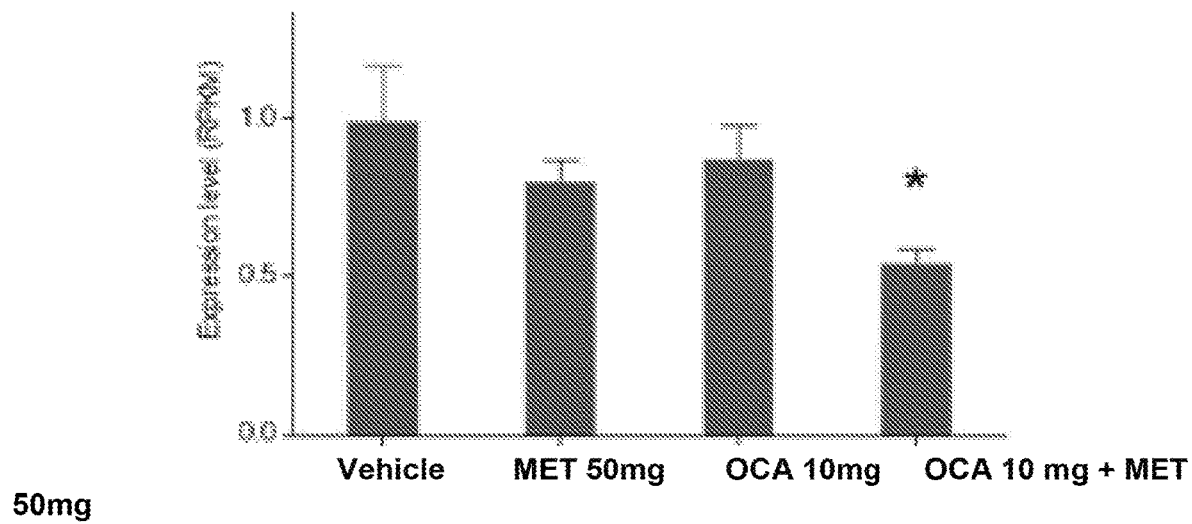
Figure 14E:
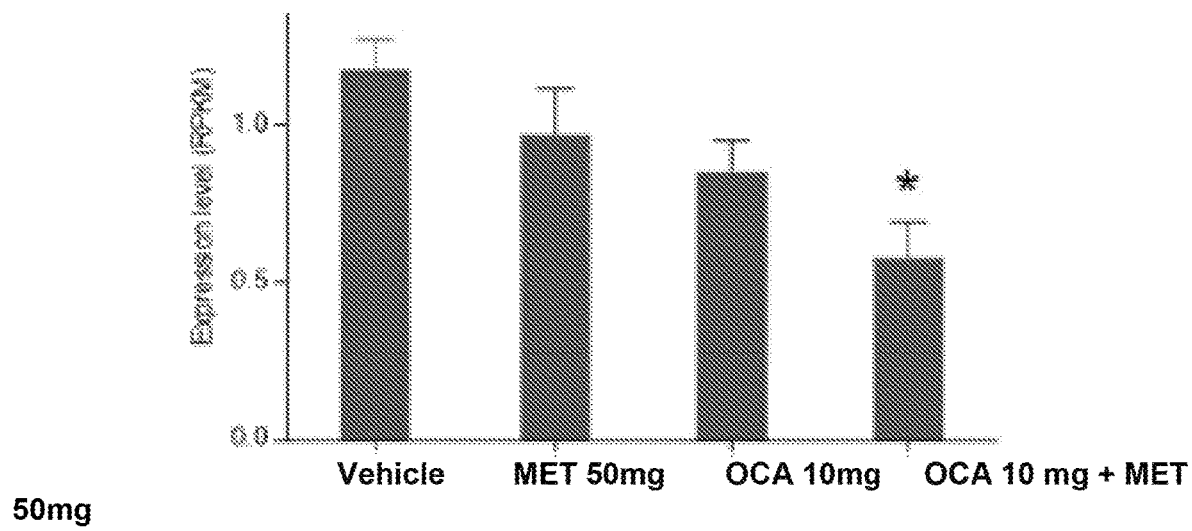
Figure 14F:
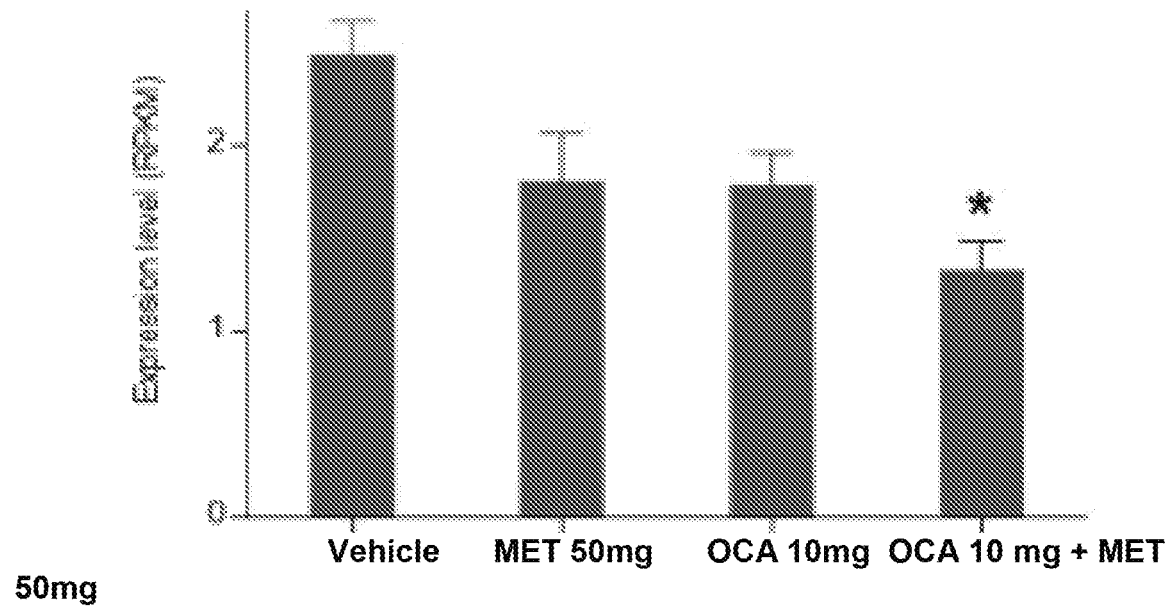

For the low dose combination, the following genes in the collagen receptor family were uniquely regulated: collagen type 14a1, collagen type 6a1, and collagen type 6a2. See FIGS. 13A-13C, respectively. Other genes of interest which were regulated are the decorin receptor, colectin subfamily member 10, transforming growth factor beta receptor III, and transforming growth factor, beta-induced. See FIGS. 14A-14F.

Figure 15A:
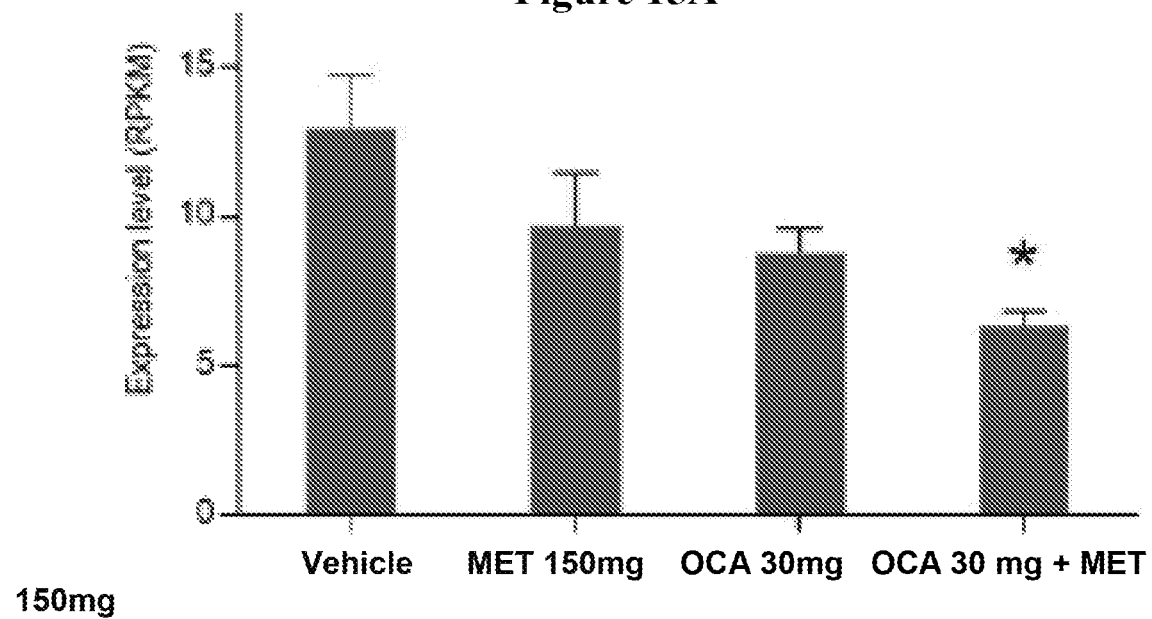
FIGS. 15A-15C describe the effect on the expression level of certain collagens regulated by a high dose OCA and MET, alone and in combination. *p<0.005 vs. vehicle control.
Figure 15B:
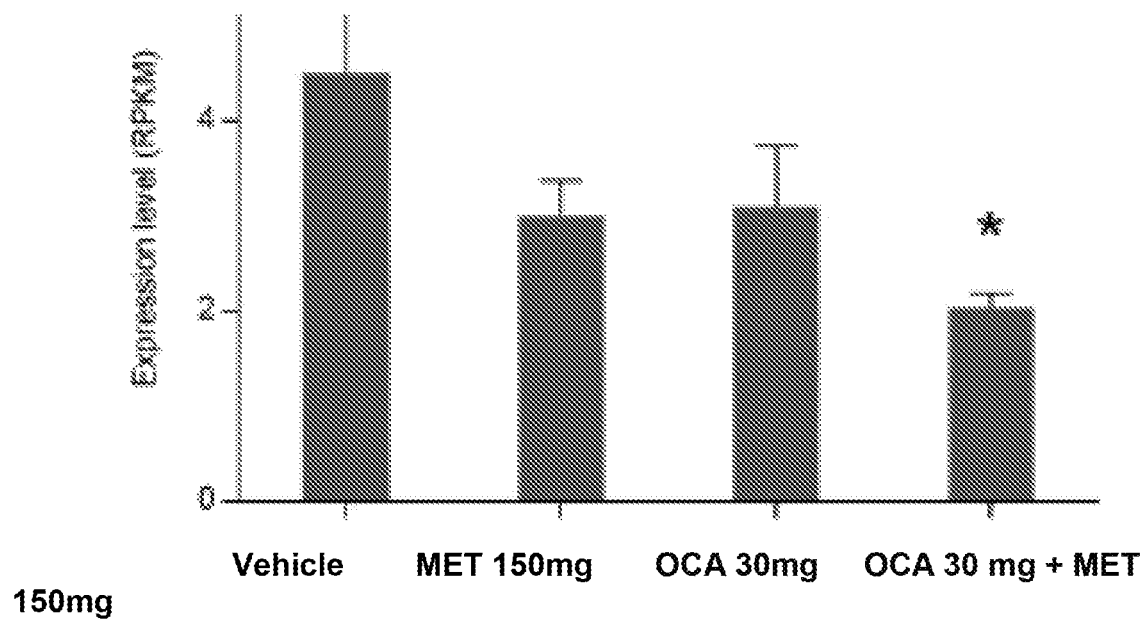
Figure 15C:
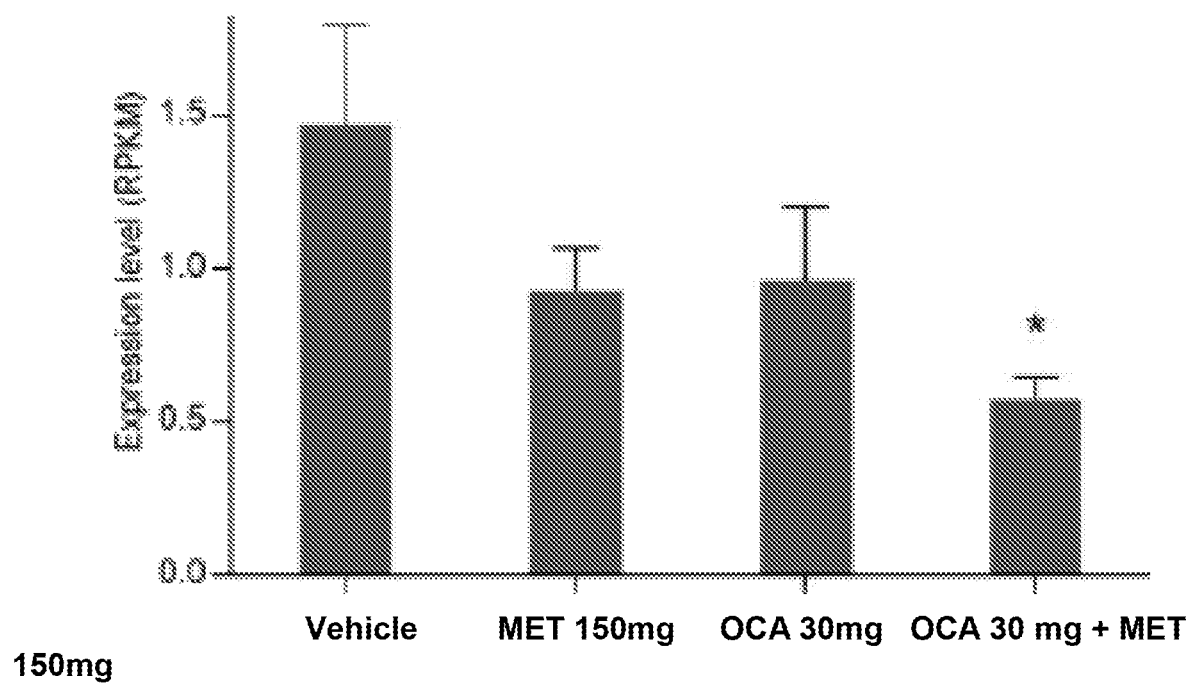
Figure 16A:
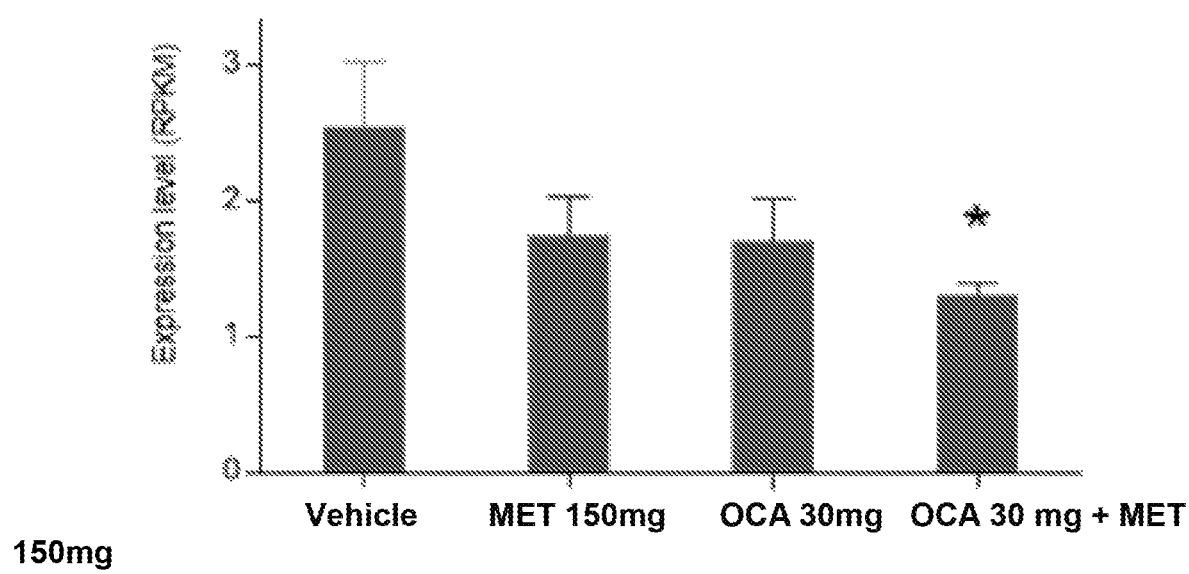
FIGS. 16A-16E describe the effect on the expression level of certain genes uniquely regulated by a high dose OCA and MET, alone and in combination *p<0.005 vs. vehicle control.
Figure 16B:
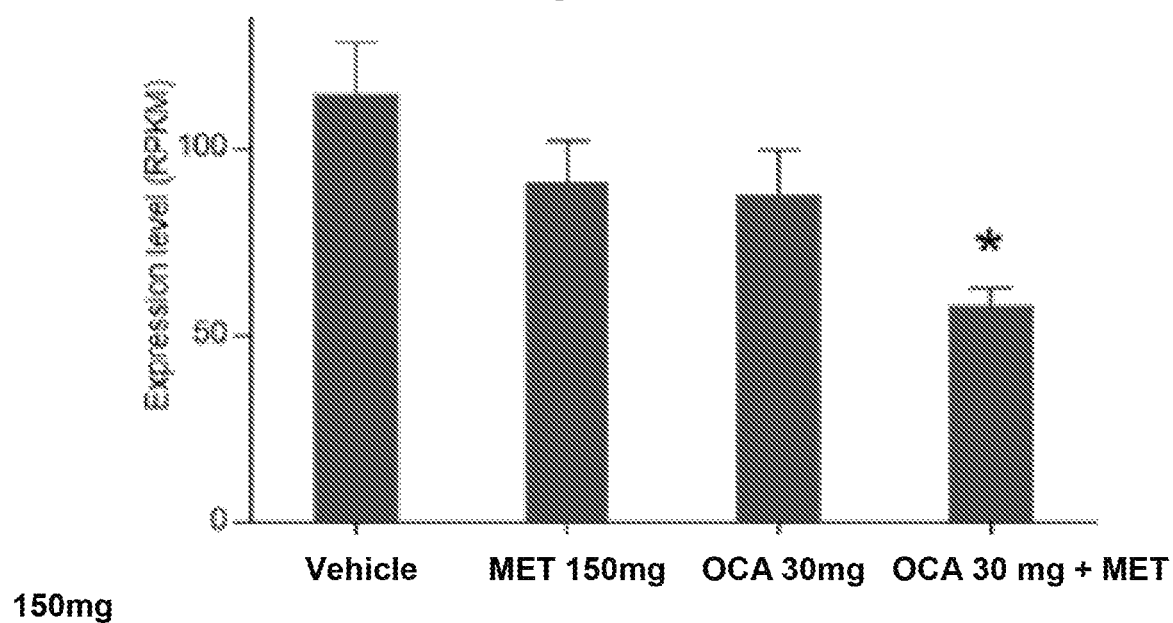
Figure 16C:
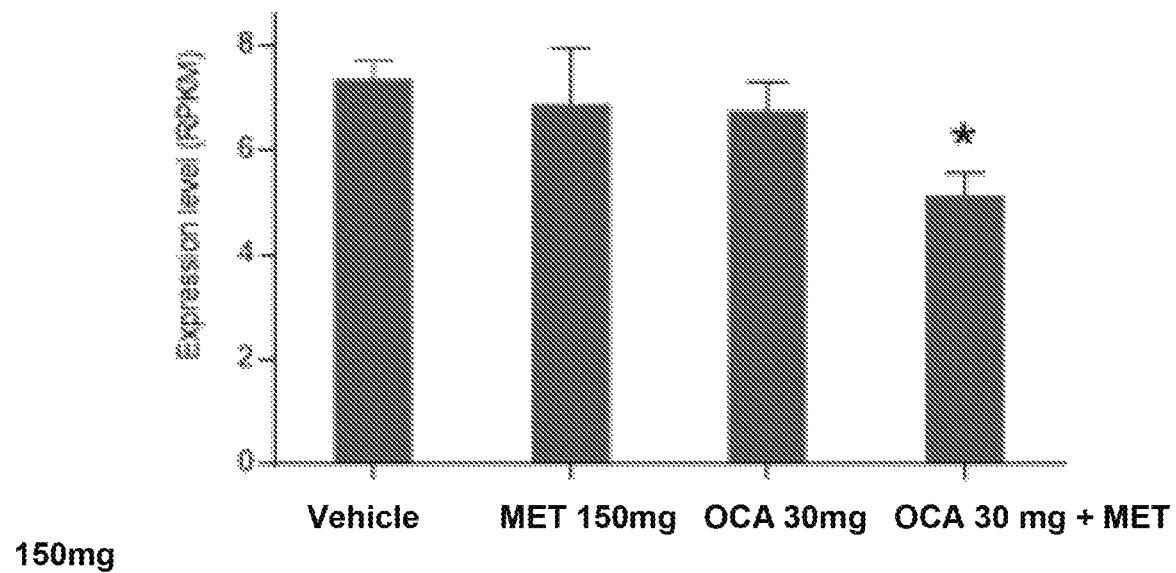
Figure 16D:
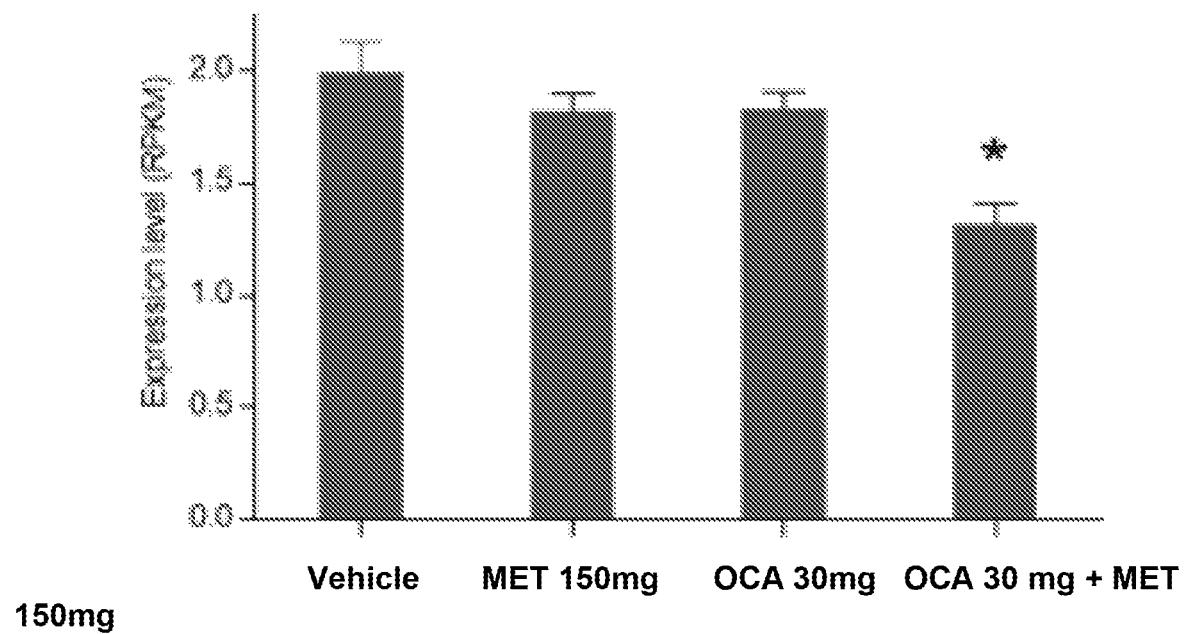
Figure 16E:
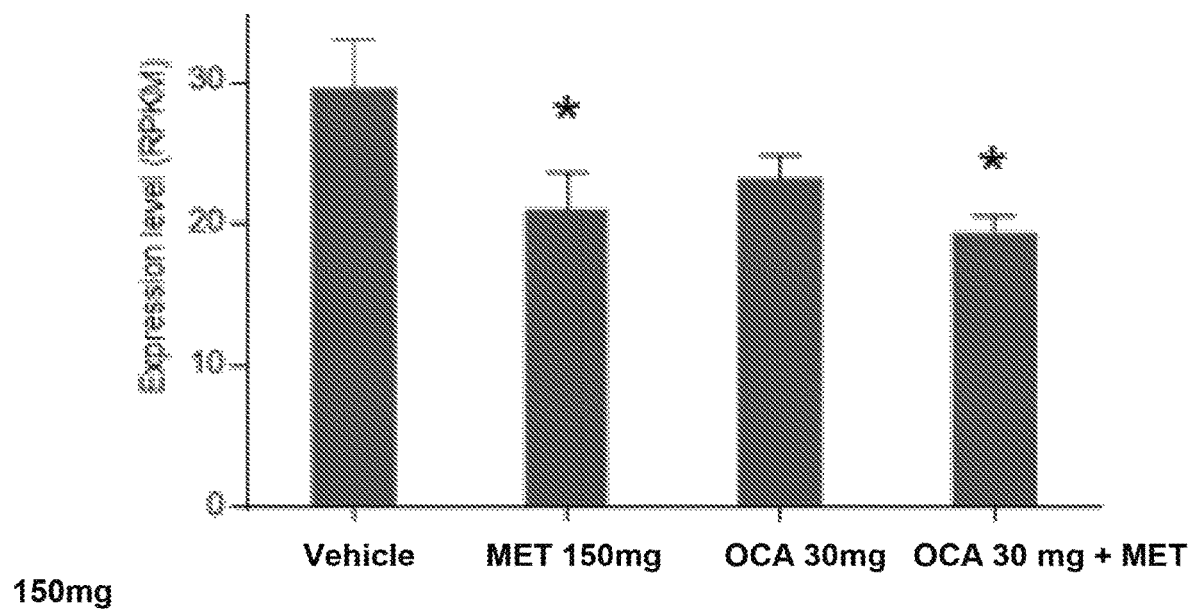

For the high dose combination, genes differentially regulated in the collagen receptor family are collagen type 14a1, collagen type 6a1, and collagen type 6a2. See FIGS. 15A-15C, respectively. Other genes of interest such as platelet-derived growth factor receptor beta, decorin, colectin subfamily member 10, transforming growth factor beta receptor 111, and transforming growth factor, beta-induced (FIGS. 16A-16E) were examined.

With respect to fibrosis factor genes, the collagen receptor family is of particular interest. Collagen occurs in many places throughout the body. Over 90% of the collagen in the human body, however, is type I. There are 29 genetically distinct collagens present in animal tissues. Collagen types I, II, III, V and XI self-assemble into D-periodic cross-

TABLE 4

| | Treatment Group | | | | | | | |
|---|---|---|---|---|---|---|---|---|
| | Group 1 | Group 2 | Group 3 | Group 4 | Group 5 | Group 6 | Group 7 | Group 8 |
| OGTT Blood Glucose AUC, (mmol/L × min) Week 4 | 1762 ± 45 | 1680 ± 71 | 1698 ± 31 | 1778 ± 88 | 1480 ± 53 ** | 1538 ± 43 ** | 1416 ± 33 ** ++ | 1615 ± 61 |

AUC refers to area under the curve;
** $P < 0.01$ vs. Group 1; and
++ $P < 0.01$ vs. Group 6

Differential Gene Expression Analysis

Figure 11:
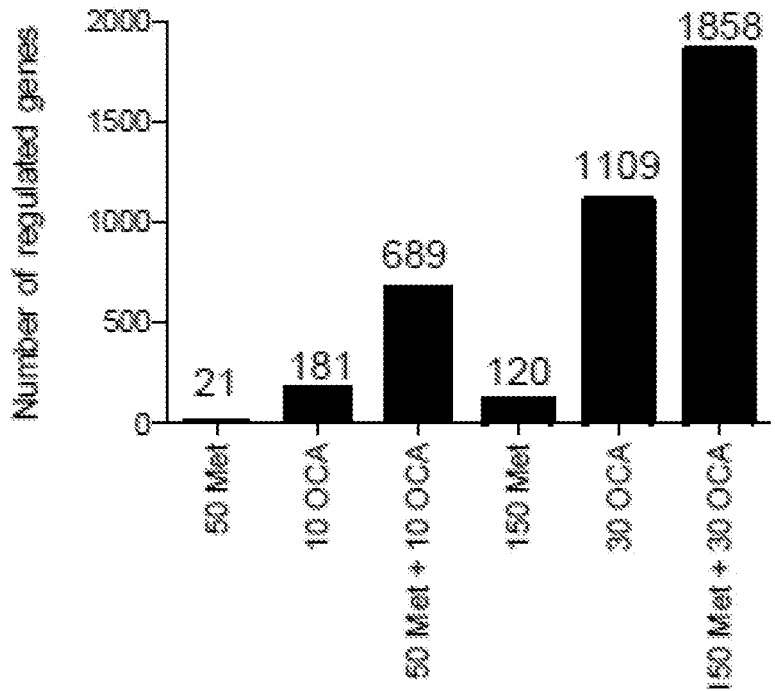
FIG. 11 is a bar graph showing the number of genes regulated by the low and high doses of OCA and MET, alone and in combination.

RNA sequencing was performed on liver mRNA samples from the study mice to gain insight into the underlying mechanisms and pathways on the improvement of the total NAS by the combination therapies. Differential gene expression analysis was conducted on terminal liver samples collected from animals treated with OCA and MET, alone and in combination. The genes differentially regulated between the low dose combination and each respective monotherapy were compared. FIG. 11 and the data on table 5 disclose the number of genes regulated by OCA and MET, alone and in combination. Generally, while the monotherapy striated fibrils. Here the D is approximately 67 nm and there is characteristic axial periodicity of collagen. These form the most abundant collagens in vertebrates.

The laminin 1 receptor is involved in membrane remodelling (achieving a lower laminin level is desirable to treat fibrosis). Collectin encodes a member of the C-lectin family, proteins that possess collagen-like sequences and carbohydrate recognition domains. The other members of this family are secreted proteins and bind to carbohydrate antigens on microorganisms facilitating their recognition and removal. Decorin plays a role in collagen fibril assembly. Binding of this protein to multiple cell surface receptors mediates its role in tumor suppression, including a stimulatory effect on autophagy and inflammation and an inhibitory effect on angiogenesis and tumorigenesis. The tumor necrosis factor receptor superfamily and the transforming growth factors are involved in the inflammatory/fibrotic progression.

Example 4. Diet-Induced Obese NASH in C57BL/6j Mice: Obeticholic Acid (OCA)±Sitagliptin (SIT)

The protocols and analyses for this study are provided in Example 1.
Treatment Groups
Group 1: Vehicle (PO)+Vehicle (PO)
  Mice (n=11) were administered vehicle (0.5% CMC) from week 0 to 8.
Group 2: OCA (PO)+Vehicle (SQ)
  Mice (n=11) were administered OCA at a dose of 10 mg/kg from week 0 to 8.
Group 3: SIT (PO)+Vehicle (PO)
  Mice (n=12) were administered SIT at a dose of 10 mg/kg from week 0 to 8.
Group 4: OCA (PO)+Vehicle (SQ)
  Mice (n=11) were administered OCA at a dose of 30 mg/kg from week 0 to 8.
Group 5: SIT (PO)+Vehicle (PO)
  Mice (n=12) were administered SIT at a dose of 30 mg/kg from week 0 to 8.
Group 6: OCA (PO)+SIT (PO)
  Mice (n=12) were administered OCA at a dose of 10 mg/kg and SIT at a dose of 10 mg/kg from week 0 to 8.
Group 7: OCA (PO)+SIT (PO)
  Mice (n=10) were administered OCA at a dose of 30 mg/kg and SIT at a dose of 30 mg/kg from week 0 to 8.
Group 8: Lean Chow control group
  Mice (n=10) were feed lean chow from week 0 to 8.
Compounds and Dosing
  All mice received PO dosing once daily. Day 0 was the first day of dosing while day 55 was the last day. Hence, mice were dosed once daily from day 0 up to and including day 55. The mice received 56 doses in total. Animals were subjected to treatment between 2:00-4:00 PM. OCA was dissolved in final stock concentrations of 1 mg/ml and 3 mg/ml for final dose concentrations of 10 mg/kg and 30 mg/kg, respectively. The dosing volume was 10 mL/kg. SIT was prepared in final stock concentrations of 5 mg/ml and 15 mg/ml for final dose concentrations of 10 mg/kg and 30 mg/kg, respectively. The dosing volume was 10 mL/kg. Vehicle used for OCA and SIT was 0.5% carboxymethyl-cellulose sodium (CMC).
Results
DPP-IV Activity
  The effects of OCA (10 and 30 mg/kg, PO) were examined alone and in combination with SIT (10 and 30 mg/kg, PO) on plasma DPP-IV activity of the DIO-NASH mice at week 2 of treatment. A low dose combination refers to OCA (10 mg/kg)/SIT (10 mg/kg) while the high dose combination refers to OCA (30 mg/kg)/SIT (30 mg/kg). The low dose combination of OCA and SIT reduced DPP-IV activity in a statistically significant matter ($p<0.01$ vs. DIO-NASH vehicle). Further, the high dose combination of OCA and SIT reduced DPP-IV activity in a statistically significant matter ($p<0.01$ vs. DIO-NASH vehicle). The pharmacological results demonstrate that the therapeutic agents produced the expected effects, i.e. DPP-IV inhibition.

Example 5. Obeticholic Acid (OCA)±Empagliflozin (EMP)

Treatment Groups
Group 1: Vehicle (PO)
  Mice are administered vehicle (0.5% CMC) from week 0 to 8.
Group 2: OCA (PO)+Vehicle (PO)
  Mice are administered OCA at a dose of 10 mg/kg from week 0 to 8.
Group 3: EMP (PO)+Vehicle (PO)
  Mice are administered EMP at a dose of 3 mg/kg from week 0 to 8.
Group 4: OCA (PO)+Vehicle (PO)
  Mice are administered OCA at a dose of 30 mg/kg from week 0 to 8.
Group 5: EMP (PO)+Vehicle (PO)
  Mice are administered EMP at a dose of 10 mg/kg from week 0 to 8.
Group 6: OCA (PO)+EMP (PO)
  Mice are administered OCA at a dose of 10 mg/kg and EMP at a dose of 3 mg/kg from week 0 to 8.
Group 7: OCA (PO)+EMP (PO)
  Mice are administered OCA at a dose of 30 mg/kg and EMP at a dose of 10 mg/kg from week 0 to 8.
Group 8: Lean Chow control group
  Mice (n=10) are feed lean chow from week 0 to 8.
Compounds and Dosing
  All mice are to receive PO dosing once daily. Day 0 is the first day of dosing while day 55 was the last day. Hence, mice are dosed once daily from day 0 up to and including day 55. The mice will receive 56 doses in total. Animals are subjected to treatment between 2:00-4:00 PM. OCA is dissolved in final stock concentrations of 1 mg/ml and 3 mg/ml for final dose concentrations of 10 mg/kg and 30 mg/kg, respectively. The dosing volume is 10 mL/kg. EMP was prepared in final stock concentrations of 5 mg/ml and 15 mg/ml for final dose concentrations of 3 mg/kg and 10 mg/kg, respectively. The dosing volume was 10 mL/kg. Vehicle used for OCA and EMP was 0.5% carboxymethyl-cellulose sodium (CMC).
  Honda, et al, "The Selective SGLT2 Inhibitor Ipragliflozin Has a Therapeutic Effect on Nonalcoholic Steatohepatitis in Mice", PloS, 2016, describe that sodium glucose cotransporter 2 inhibitors (such as empagliflozin) have been investigated for their effect in DIO-NASH mice.

Example 6: Sandwich Culture of Hepatocytes

Reagents and Solutions
  Suitable cell culture medium includes Waymouth's MB-752/1, Ham's F12, RPMI 1640, Dulbecco's modified Eagle's medium, Williams' medium E, Leibovitz's L15 and modified Chee's medium. Type IV collagenase, type I collagen, Percoll, culture medium and supplements are added to the culture medium (e.g., serum, antibiotics, amino acids, hormones such as DEX, insulin, and growth factors), perfusion buffer, and other solutions were commercially available or made from commercially available materials. Other types of collagen (types II-IV), laminin, fibronectin, and heparin sulfate proteoglycans can be used in the sandwich hepatocyte culture. However, it has been shown that type I and IV collagen were superior to fibronectin and laminin in culturing of the cells.

Isolation of Hepatocytes

A two-step in situ collagenase perfusion method is utilized to isolate hepatocytes. Briefly, hepatocytes are isolated from female Lewis rats. Animals are anesthetized. The liver is first perfused through the portal vein in situ with a perfusion buffer. The perfusate is equilibrated before entering the liver. The liver is subsequently perfused with collagenase in the perfusion buffer. The liver is dissected and transferred to ice-cold perfusion buffer. The liver capsule is teased apart, and the resulting cell suspension is filtered. The cell pellet is collected by centrifugation and resuspended. Percoll is added to the suspension, and hepatocytes separated using a Percoll density centrifugation technique. The mixture is centrifuged, and the cell pellet washed twice with medium. Hepatocyte viability is determined by Trypan blue exclusion. Alternatively, cryopreserved hepatocytes are used instead of freshly isolated hepatocytes.

Sandwich Culture of Hepatocytes

Isolated hepatocytes are cultured on collagen-coated tissue culture plates and maintained in culture medium supplemented with serum, penicillin, streptomycin, epidermal growth factor, insulin, glucagon and hydrocortisone. A collagen gelling solution is prepared by mixing Type I collagen solution and culture medium. Tissue culture plates are coated with the gelling solution and incubated at 37° C. to promote gel formation. Hepatocytes are seeded at a proper density and maintained at 37° C. The culture medium is replaced every 24 hours.

For the sandwich system, an additional collagen gel solution are distributed over the cells after 1 day of culture. The culture medium is carefully removed to ensure that the second layer of collagen gel is evenly spread over the entire plate. The culture plates are incubated at 37° C. to allow gelation and attachment of the second gel layer before the medium is replaced. The culture medium is changed daily. Medium samples are stored at −20° C. for further analysis.

Hepatocytes cultured between layers of gelled collagen maintain a three-dimensional cuboidal shape and distribution of cytoskeletal proteins similar to that observed in vivo.

Optimization of Bile Canalicular Network Formation

To optimize taurocholate accumulation and biliary excretion, particular culture medium, such as Williams' medium E and Dulbecco's modified Eagle's medium can be used in the sandwich hepatocyte culture.

Test Articles

The FXR agonist intended for study is obeticholic acid, also known as "OCA" and 6-ethyl chenodeoxycholic acid (6-ECDCA).

Example 7: Evaluate Effects of Test Articles on Glucose Release from Liver Cells Hepatocyte Isolation Livers are obtained from 6-month-old female pigs after 12 h of fasting. The tissues are harvested from the animals. Hepatocytes are isolated by a modification of the two-step in situ collagenase perfusion method based on the procedure described by Seglen (Seglen, *Methods in Cell Biol.* 13, 29 (1976)). Within 15 min of the animal being killed, the right lobe of the liver is removed and then perfused with liver perfusion medium at 37° C. for 15-20 min, followed by liver digestion medium for 20-30 min. Hepatocytes are isolated by gentle disruption of the digested liver in suspension medium [26.5 mM $NaHCO_3$, 8.99 mM Na-HEPES, 0.2% (wt/vol) BSA fraction V, 2.22 mM D-fructose, in DMEM with 5.5 mM glucose and 1 mM Na pyruvate] and filtered through a 200-μm mesh. The resulting cell suspension is centrifuged at 500 rpm, the supernatant is discarded, and the cell pellet resuspended in prewarmed (37° C.) suspension medium. Cell viability is assessed using the Trypan blue exclusion method (Life Technologies, Grand Island, N.Y.) and is consistently higher than 85%. Cell counts are performed in triplicate, and the mean value is obtained.

Suspension Cultures

Immediately after the isolation, hepatocytes are washed three times with serum-free DMEM without glucose or pyruvate and then resuspended in 600 μl of the same medium at a cell density of $30 \times 10^6$/ml in 50-ml conical tubes. The tubes are incubated at 37° C. for 10, 20, and 40 min with continuous shaking, alone or with increasing concentrations of a compound of the present application (e.g., OCA), together with at least one additional therapeutic agent (e.g., those described herein). In each experiment, glucose output after stimulation with 100 nM glucagon is used as positive control.

After the incubation period, glucose released into the medium is determined with the glucose-oxidase method using a Trinder assay kit (Sigma), and the results of all replicates are normalized for protein content, which are determined using the Bio-Rad protein assay kit.

Example 8: Evaluate Effects of Test Articles on Glucose Metabolism in Liver Cells Cell Culture Hepatocytes from male Sprague-Dawley rats (200-250 g) are isolated by collagenase perfusion of the liver, as described previously (Brown et al., *Biochem. J.* 262, 425 (1989)). Viability, as assessed by trypan blue exclusion, is routinely in excess of 90%. Six-well collagen-coated plates are loaded with $10^6$ live cells per well with 2 mL of Dulbecco modified Eagle medium containing 10% (vol/vol) fetal calf serum. After 1 hour, during which time only the live cells became attached to the plate, the medium is aspirated (along with unattached dead cells) and replaced with fresh medium. Cells are maintained for up to 48 hours (with at least one change of medium at 24 hours). Animal procedures are in accordance with the humane care criteria of the National Academy of Sciences.

Glucose Metabolism

Parameters of hepatocyte glucose metabolism are measured after 18-hour incubation in the absence or presence of a compound of the present application (e.g., OCA), together with at least one additional therapeutic agent (e.g., those described herein). Glucose utilization is determined as the production of tritiated water (as for fatty acid oxidation experiments) after incubation of hepatocytes for 2 hours in the presence of [5-$^3$H]-glucose (6.5 μCi/mL). Uptake of 2-[$^3$H]-deoxyglucose (DOG; 10 mol/L, 0.5 μCi/mL) is determined over 5 minutes after 30 minutes of preincubation with or without 100 nmol/L insulin during each period (Perdomo et al., *J. Biol. Chem.* 279, 27177 (2004)). Incorporation of D-[$^{14}$C]-glucose (2 μCi/mL) into glycogen is measured in the absence or presence of insulin over 1 hour (Perdomo et al. 2004).

Example 9: Evaluate Effects of Test Articles on Glucose Metabolism in Liver Cells and Mice Cell Culture and Transient Transfection Human hepatoblastoma cells (HepG2) are seeded into 6-well plates $1 \times 10^6$ cells/well) and grown in complete culture medium [high-glucose Dulbecco's modified Eagle's medium (with L-glutamine) supplied with 10% (vol/vol)

inactivated fetal calf serum and 1% (vol/vol) antibiotics-antimycotics] as described (Wang et al., *Mol. Endocrinol.* 22, 1622 (2008)). The following day, cells are treated with a compound of the present application (e.g., OCA), together with at least one additional therapeutic agent (e.g., those described herein). Eighteen hours after treatment, the cells are treated with TPA (50 nM), LPS (1 µg/mL), or TNF-α (10 ng/mL) and then collected for RNA isolation after a 6-hour incubation.

Transient transfection of HepG2 cells is performed using Lipofectamine 2000 (Invitrogen, Carlsbad, Calif.). Cells are pretreated with a compound of the present application (e.g., OCA), together with at least one additional therapeutic agent (e.g., those described herein) for 18 hours, unless stated otherwise. Cells are treated with or without LPS or TPA. Following a 6-hour incubation, cells are harvested and the luciferase activity is determined using a dual-luciferase reporter assay system in accordance with the manufacturer's instructions (Promega, Madison, Wi). Luciferase activities are normalized via cotransfection of the control thymidine kinase driven *Renilla* luciferase plasmid, phRL-TK. Data are expressed as relative fold activation to that of nonstimulated sets.

Primary Mouse Hepatocyte Culture

Primary hepatocytes from 8-week-old mice are prepared as described (Huang et al., *Mol. Endocrinol.* 18, 2402 (2004), Huang et al., *J. Clin. Invest.* 113, 137 (2004), Qiao et al., *Mol. Biol. Cell* 12, 2629 (2001)). Cells are treated with a compound of the present application (e.g., OCA), together with at least one additional therapeutic agent (e.g., those described herein). Eighteen hours after treatment, cells are treated with LPS (20 µg/mL), TPA (150 nM), or TNF-α (10 ng/mL) and then collected for RNA isolation after a 6-hour incubation.

RKA Isolation and Quantitative Real-Time Polymerase Chain Reaction

Total INA isolation from HepG2 cells, primary mouse hepatocytes, and mouse livers and quantitative real-time polymerase chain reaction (PCR) are performed as described (Yang et al., *Cancer Res.* 67, 863 (2007)). Amplification of β-actin is used as an internal reference.

Animals

Eight-week-old mice, unless stated otherwise, are be used. The wild-type and FXR-mice are maintained in a pathogen-free animal facility under a standard 12:12-hour light/dark cycle. Mice are fed standard rodent chow and water ad libitum. Eight-week-old female wild-type and FXR$^{-/-}$ mice are fasted overnight and then injected intraperitoneally with a single dose of LPS (20 mg/kg) or phosphate-buffered saline (PBS), or a compound of the present application (e.g., OCA), together with at least one additional therapeutic agent (e.g., those described herein), followed by feeding water ad libitum. Six hours after the injection, mice are killed, and blood and livers are removed for further analysis. All procedures follow National Institutes of Health guidelines for the care and use of laboratory animals.

Example 10: Evaluate Effects of Test Articles in Animal Model

Insulin resistance is the putative key underlying mechanism linking adipose tissue (AT) dysfunction with liver inflammation and steatosis in metabolic syndrome (MetS). It has been demonstrated that OCA ameliorates insulin resistance and the metabolic profile with a marked reduction in the amount of visceral AT (VAT) in a high-fat diet (HFD)-induced rabbit model of MetS. Analysis of VAT and liver through immunohistochemistry, Western blot, and RT-PCR has shown that in vivo OCA dosing normalizes adipocyte size, hypoxia, and the expression of perilipin and cytosolic insulin-regulated glucose transporter GLUT4 (SLC2A4) which are significantly increased in VAT isolated from the HFD rabbits as compared to rabbits on a control diet. In vivo OCA dosing also normalizes the expression of steatosis and inflammation markers in HFD rabbits.

MetS Rabbit Model

The HFD-induced rabbit model of MetS is obtained as described previously (Filippi et al., *J. Sexual Med.* 6, 3274 (2009)). Male New Zealand White rabbits, weighing about 3 kg, are randomly numbered and assigned to two different groups: untreated group, fed a control diet (CON), or treated group, fed a HFD (0.5% cholesterol and 4% peanut oil), for 12 weeks. A subgroup of HFD rabbits are treated with a compound of the present application (e.g., OCA), together with at least one additional therapeutic agent (e.g., those described herein). The dose of OCA used may be selected based on the efficacy and pharmacokinetic analysis carried out in rodents (Pellicciari et al., *J. Med. Chem.* 45, 3569 (2002)). The doses of the additional therapeutic agent, such as those described herein, may also be selected based on the efficacy and pharmacokinetic analysis in animals (e.g., mice, rats, rabbits, pigs) as published in the literature.

Blood samples are obtained from marginal ear vein at baseline and at week 12 in all the groups. Mean arterial pressure measurements and oral glucose tolerance test is carried out before killing, as described previously (Filippi et al. 2009). After 12 weeks of treatment, the rabbits are killed using a lethal dose of pentobarbital (100 mg/kg), and the specimens of the liver, VAT (accumulated between the intestinal loops and mesentery), and gallbladder are carefully excised, weighed, collected, and processed for the subsequent analyses. VAT samples from all the rabbit groups are processed for the isolation of preadipocytes. Biochemical and hormonal serum analyses are performed as described previously (Filippi et a. 2009, Morelli et al., *J. Steroid Biochem. Mol. Biol.* 132, 80 (2012), Vignozzi et al., *J. Endocrinology* 212, 71 (2012)).

To evaluate the effects of MetS, an algorithm taking into account the presence, as a dummy variable, of one or more of the following factors: hyperglycemia, high triglyceride levels, high cholesterol levels, increased blood pressure, and visceral fat accumulation, are designed. Cut-offs for each factor is derived by the mean±2 S.D. of the analyzed parameter, as measured in the CON rabbits. Positivity for three or more factors indicates MetS.

Sample Size

Assuming a probability of the occurrence of MetS of 2.5% in the CON group and a probability of 60% in the HFD group (Filippi et al. 2009, Vignozzi et al, *J. Sexual Med.* 8, 57 (2011), Vignozzi et al. 2012, Maneschi et al., *J. Endocrinology* 215, 347 (2012), Morelli et al. 2012, Morelli et al., *Prostate* 73, 428 (2013)), the use of 74 rabbits with an allocation ratio of 1:1 between the groups will allow a power close to 100% in distinguishing a difference in the rate of development of MetS between the two treatment groups. Assuming a probability of the occurrence of MetS equal to 60% in the group fed the HFD and a probability of 10% in the group fed the HFD and a compound of the present application (e.g., OCA), together with at least one additional therapeutic agent (e.g., those described herein) (Vignozzi et al. 2011, Morelli et al. 2012), the use of 54 rabbits with an allocation ratio of 2:1 will allow a power of about 95% in distinguishing a difference in the rate of development of MetS between the two treatment groups.

Histomorphometric Analysis of VAT

VAT specimens are analyzed by hematoxylin and eosin staining to measure adipocyte diameter, as described previously (Maneschi et al. 2012), using the Nikon Microphot-FXA microscope (Nikon, Tokyo, Japan) equipped with the free software program ImageJ (NIH, Bethesda, Md., USA), considering adipocytes to be regularly spherical.

Hypoxia Detection and Immunohistochemistry

VAT oxygenation are analyzed using the bio-reductive drug pimonidazole hydrochloride (hypoxyprobe-1, 60 mg/kg), injected i.p. 1 h before killing, as described previously (Maneschi et al. 2012, Morelli et al. 2012, 2013, Vignozzi et al. 2012).

Preparation of Total and Membrane/Cytosolic Fractions for Western Blot Analysis

For protein extraction from the VAT samples, the frozen tissues are ground in liquid nitrogen and divided into two aliquots: one for total protein extraction and the other for membrane/cytosolic preparations. Membrane and cytosolic fractions are prepared using the ProteoExtract subcellular proteome extraction kit (Calbiochem-Merck KGaA, Darmstadt, Germany), according to the manufacturer's instructions. Protein extracts are quantified with the BCA reagent (Pierce, Rockford, Ill., USA), and 15 mg of each sample is resolved by 10% SDS-PAGE. Western blot analysis with an anti-glucose transporter type 4 (GLUT4) antibody (Upstate Biotechnology, Lake Placid, N.Y., USA) and anti-perilipin antibody (Santa Cruz Biotechnology, Inc.) are performed as described previously (Maneschi et al. 2012). Equal protein loading are verified by reprobing the membrane with an anti-actin antibody (Santa Cruz Biotechnology, Inc.). Densitometry analysis of band intensity is performed using the Adobe Photoshop Software.

Liver Histology

Liver steatosis is assessed by Oil Red O staining of the liver sections. Frozen sections are cut in a cryostat and fixed in 4% paraformaldehyde for 20 min at room temperature (RT). Then, the sections are treated for 2-5 min with isopropanol and stained with Oil Red O for 20 min. Oil Red O are prepared by diluting a stock solution (0.3 g of Oil Red O in 100 ml of isopropanol) with water (3:2) followed by filtration. After Oil Red O staining, the sections are washed several times in water and stained with hematoxylin and eosin to highlight the hepatocyte nuclei. Finally, the sections are photographed, and computer-assisted quantification of Oil Red O positivity are done after background subtraction using the Adobe Photoshop Software.

Immunohistochemistry for Inflammatory Markers in the Liver Sections

Liver sections are incubated overnight at 48° C. with primary antibodies against various inflammatory markers (e.g., TNFα, Cd68, Il-6, Il-1b, and Il-12). The sections are rinsed in PBS and incubated with a biotinylated secondary antibody and then with a streptavidin-biotin-peroxidase complex (Ultravision large volume detection system antipolyvalent, Lab Vision, Fremont, Calif., USA). The reaction product is developed with 3',3'-diaminobenzidine tetrahydrochloride as the chromogen (Sigma-Aldrich). Control experiments are performed by omitting the primary antibody. The slides are evaluated and photographed using a Nikon Microphot-FXA microscope. Computer-assisted quantification of the staining against inflammatory markers are done after background subtraction using the Adobe Photoshop Software.

Isolation, Characterization, and Differentiation of Rabbit Visceral Fat Preadipocytes The isolation of rabbit preadipocytes (rPADs) from VAT is carried out as described previously (Maneschi et al. 2012). Briefly, VAT samples are digested with 1 mg/ml collagenase type 2 (Sigma-Aldrich) for 1 h, treated with red blood cell lysis buffer (155 mM $NH_4Cl$, 10 mM $KHCO_3$, and 0.1 mM EDTA; 10 min at RT), then centrifuged at 2000 g for 10 min at RT, resuspended in a complete medium (DMEM containing 10% fetal bovine serum (FBS), 100 mg/ml streptomycin, 100 U/ml penicillin, 2 mM L-glutamine, and 1 mg/ml amphotericin-B; Sigma-Aldrich), and filtered through a 150 mm mesh filter to remove debris. Finally, the cells are cultured in a complete culture medium at 37° C. in a humidified atmosphere of 95% air-5% C02. A subconfluent (90% of the cell culture dish) and homogeneous fibroblast-like cell population at passage 0 (P0) is obtained after 4-5 days of culture. The subconfluent cells are trypsinized and plated in cell culture dishes (P1). For all the experiments, only P1 cultures are used, and the experiments are repeated using at least three different rPAD preparations for each experimental group. rPADs are characterized by flow cytometry with the following conjugated monoclonal antibodies: CD34-PE, CD45-FITC, CD31-FITC, CD14-PE, CD90-PE, CD106-FITC (BD Pharmingen, San Diego, Calif., USA), and CD105-PE (Ancell, Bayport, Minn., USA), as described previously (Maneschi et al. 2012). The differentiation of rPADs, 2 days after confluence (time 0), is induced by exposing them to a differentiation mixture (DIM) containing 5 mg/ml insulin, 1 mM dexamethasone, and 0.5 mM 3-isobutyl-1-methylxanthine (IBMX) in 5% stripped FBS-supplemented DMEM for 8 days. The culture medium is replaced every 48 h, and then the cells are shifted into a medium containing 5 mg/ml insulin for 48 h.

Glucose Uptake

Glucose uptake by rPADs is measured as described previously (Maneschi et al. 2012). DIM-exposed rPADs is cultured for 24 h in a serum-free medium, followed by incubation in increasing concentrations of insulin (1, 5, 10, and 50 nM) diluted in glucose-free Krebs phosphate buffer (2.5 mmol $Ca_2C$ and 1 mg/ml BSA), to evaluate insulin-dependent stimulation. At the end of the incubation period, rPADs is further incubated with 3H-2-deoxy-D-glucose (16 mM (1 mCi/ml); ICN Pharmaceuticals, Costa Mesa, Calif., USA) for 5 min. The cells are washed with PBS and lysed with NaOH 0.5 M, and the incorporated radioactivity is measured by scintillation spectrometry using a β-counter (Perkin-Elmer). Data are normalized on protein content.

Statistical Analysis

Results are expressed as means±S.E.M. for n experiments as specified. The statistical analysis is performed with a one-way ANOVA test followed by the Tukey-Kramer post hoc analysis in order to evaluate differences between the groups, and P<0.05 is considered significant. Correlations are assessed using Spearman's method, and the statistical analysis is performed with the Statistical Package for the Social Sciences (SPSS, Inc.) for Windows 15.0. Stepwise multiple linear regressions are applied for the multivariate analysis, whenever appropriate. Half-maximal response effective concentration ($EC_{50}$) values and maximal effect ($E_{max}$) values are calculated using the computer program ALLFIT.

Example 11: Evaluate Effects of Test Articles in Animal Model

Experimental Animals and Diets

Animals are housed individually in standard cages at 22° C. in a 12:12-h light-dark cycle. Male C57BL6 (B6) or $Lep^{ob}/Lep^{ob}$ mice aged ~7 wk are purchased from The Jackson Laboratory (Bar Harbour, Me.). Test diets are sourced from Research Diets (New Brunswick, N.J.). To induce NASH, a diet comprised of high fat (40% kcal) and high fructose (22% by wt), are tested, where the source of fat is trans-fat (Primex partially hydrogenated vegetable oil shortening, cat. no. D09100301). A low-fat diet (10% kcal/fat) with no fructose or cholesterol is used as a control diet (cat. no. D09100304). The HTF diet is deemed to be superior at inducing NASH and is utilized in subsequent studies.

Studies and Drug Administration

To characterize the development of NASH on these diets $Lep^{ob}/Lep^{ob}$ or B6 mice either a low-fat diet (LFD), the high trans-fat, high fructose, high cholesterol (HTF) diet, or the high lard fat, high fructose, high cholesterol diet (HLF) diet are maintained for 8 or 12 weeks, respectively. Mice are implanted subcutaneously with a single osmotic minipump (model 2004; Alzet, Cupertino, Calif.) delivering either vehicle (50% DMSO in sterile water) or a compound of the present application (e.g., OCA), together with at least one additional therapeutic agent (e.g., those described herein). In addition or alternatively, mice may have either vehicle or a pharmaceutical composition of the present application administered once daily via oral gavage. Body weight is measured weekly. Body composition is measured at baseline (the day before pump implant) and at termination by NMR (Echo Medical Systems, Houston, Tex.).

To assess the impact of body weight loss on hepatic endpoints the initial study in $Lep^{ob}/Lep^{ob}$ mice exposed to LFD or HTF diet as described above is repeated. After 8 weeks on LFD or HTF diet, all mice are orally administered a compound of the present application (e.g., OCA), together with at least one additional therapeutic agent (e.g., those described herein) for 8 or 12 weeks.

At termination, liver tissue is excised and fixed in 10% neutral-buffered formalin (at least 7 days at room temperature). Liver tissue will then be paraffin-embedded, sectioned, and mounted and stained with hematoxylin and eosin. To visualize fibrosis, another set of sections are stained with Sirius Red (Sigma-Aldrich, St Louis, Mo.). Sections are first stained with Weigert's iron hematoxylin, followed by Biebrich scarlet, phosphotungstic/phosphomolybdic acid, and aniline blue treatment. A second set of sections are immunostained using an antibody targeted to the macrophage marker Mac-2 (Cedarlane Laboratories, Burlington, N.C.), according to standard protocols. All histological analyses are conducted by a pathologist blinded to the treatment conditions.

Total liver lipid is extracted from the liver using a protocol adapted from Folch et al. (J. Biol. Chem. 226, 497 (1957)). Approximately 0.5 g frozen liver tissue is homogenized in 10 ml of 2:1 chloroform/methanol solution. The homogenate is filtered using fat-free paper and funneled into a pre-weighed 15-ml glass centrifuge tube. Next, an additional 5 ml 2:1 chloroform/methanol solution is added followed by 2.5 ml 0.9% NaCl. The filtered extract is subsequently mixed and centrifuged at 2,000 rpm, 10° C. for 5 min. The aqueous layer is discarded, and the tube flushed with nitrogen until the lipid pellet is dry. The tube containing the lipid pellet is reweighed, and total lipid extracted per gram of starting liver is calculated.

For Western blot analysis, excised liver tissue is weighed, then snap-frozen in liquid nitrogen and stored at −80° C. until processed. Protein is isolated from a fragment of each liver as follows. The frozen liver tissue is crushed on dry ice and then homogenized in lysis buffer with protease inhibitors (cat. no. 05892791001; Roche Complete Tablets; and 0.6 mM PMSF). Protein concentration of the cleared supernatant is measured with a BCA protein assay kit (Pierce, Rockford, Ill.). Liver tissue lysates (50 g) are separated on reduced Nupage gels and transferred to PVDF membranes, following manufacturer's protocols (Invitrogen, Carlsbad, Calif.). Membranes are cut between the 50- and 60-kDa markers and blocked with 5% Blotto; the upper half is probed with anti-collagen, type 1 (1:350; cat. no. NBP-30054; Novus Biologicals, Littleton, Colo.), and for normalization, the lower half, with anti-GAPDH (1:10,000; horseradish peroxidase conjugated; cat. no. 3683; Cell Signaling Technologies, Danvers, Mass.). Following incubation with horseradish peroxidase anti-rabbit antibody, protein expression is detected with enhanced chemiluminescence (Pierce), and densitometry performed using a FluorChem System (Cell Biosciences, Santa Clara, Calif.).

Tissue Gene Expression

Livers are excised at termination, weighed, snap-frozen in liquid nitrogen, and stored (−80° C.). Total RNA is extracted using TRI-reagent (Ambion, Austin, Tex.) with RNeasy columns (Qiagen, Chatsworth, Calif.), and cDNA are generated using the RETROscript RT-PCR reverse transcription system (Ambion). Quantitative real-time PCR (ABI PRISM 7900 Sequence Detection System; Applied Biosystems; Foster City, Calif.) for genes involved in NASH pathology (e.g., genes involved in steatosis, inflammation and fibrosis). Assay can be performed using Taqman gene expression assays-on-demand and Universal PCR master mix (Applied Biosystems).

Plasma Hormone and Metabolite Analyses

Plasma glucose, triglyceride, total cholesterol, ALT, and aspartate aminotransferase (AST) levels are measured using an Olympus AU400e Bioanalyzer (Olympus America Diagnostics, Center Valley, Pa.). Plasma samples are diluted 1:10 with PBS for detection of ALT and AST within the range of the standard curve. Total plasma adiponectin is measured using a commercially available ELISA according to manufacturer's instructions (Millipore, Billerica, Mass.

The invention claimed is:

1. A pharmaceutical composition comprising an FXR agonist, at least one additional therapeutic agent, and optionally one or more pharmaceutically acceptable carriers, wherein the FXR agonist is a compound of formula I:

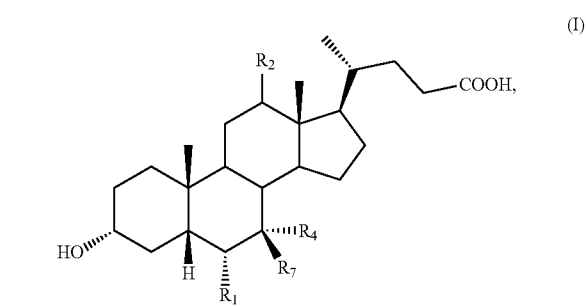

or a pharmaceutically acceptable salt or amino acid conjugate thereof, wherein:
  $R_1$ is hydrogen or unsubstituted $C_1$-$C_6$ alkyl;
  $R_2$ is hydrogen or α-hydroxyl;
  $R_4$ is hydroxyl or hydrogen; and
  $R_7$ is hydroxyl or hydrogen,
wherein the at least one additional therapeutic agent is a GLP-1 receptor agonist selected from exenatide/exendin-4, liraglutide, taspoglutide, lixisenatide, albiglutide, dulaglutide, semaglutide, BRX-0585 (Pfizer/Biorexis), and CJC-1134-PC (exendin-4 conjugated to human albumin), wherein the pharmaceutical composition is in a form for oral administration.

2. The pharmaceutical composition of claim 1, wherein the GLP-1 receptor agonist is liraglutide.

3. The pharmaceutical composition of claim 1, wherein the GLP-1 receptor agonist is selected from exenatide/exendin-4, liraglutide, taspoglutide, lixisenatide, albiglutide, dulaglutide, and semaglutide.

4. The pharmaceutical composition of claim 1, wherein the FXR agonist is Compound 1:

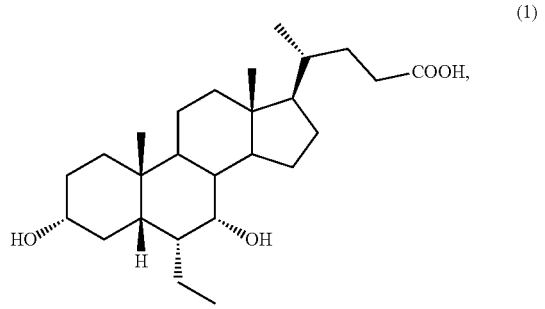 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

(1)

or a pharmaceutically acceptable salt or amino acid conjugate thereof.

5. A method of treating or preventing non-alcoholic fatty liver disease (NAFLD) or non-alcoholic steatohepatitis (NASH), comprising administering the pharmaceutical composition of claim 1 to a subject in need thereof.

6. A method of treating or preventing a disease or condition related to an elevated level of glucose in the blood, decreased secretion of insulin, and/or decreased insulin sensitivity, comprising administering the pharmaceutical composition of claim 1 to a subject in need thereof.

7. The method of claim 6, wherein the disease or condition is selected from NAFLD, NASH, hyperglycemia, diabetes, obesity, and insulin resistance.

8. A method of lowering the glucose level in the blood, stimulating insulin secretion, and/or increasing insulin sensitivity, comprising administering a therapeutically effective amount of the pharmaceutical composition of claim 1 to a subject in need thereof.

* * * * *